US007834237B2

(12) United States Patent
Wischik et al.

(10) Patent No.: US 7,834,237 B2
(45) Date of Patent: Nov. 16, 2010

(54) MATERIALS AND METHODS RELATING TO PROTEIN AGGREGATION IN NEURODEGENERATIVE DISEASE

(75) Inventors: Claude Michel Wischik, Aberdeen (GB); Janet Elizabeth Rickard, Aberdeen (GB); David Horsley, Aberdeen (GB); Charles Robert Harrington, Aberdeen (GB); Franz Theuring, Berlin (DE); Karsten Stamer, Berlin (DE); Claudia Zabke, Aberdeen (GB)

(73) Assignee: WisTa Laboratories Ltd., Singapore (SG)

( * ) Notice: Subject to any disclaimer, the term of this patent is extended or adjusted under 35 U.S.C. 154(b) by 621 days.

(21) Appl. No.: 10/451,367

(22) PCT Filed: Jan. 2, 2002

(86) PCT No.: PCT/GB02/00005

§ 371 (c)(1),
(2), (4) Date: Nov. 5, 2003

(87) PCT Pub. No.: WO02/059150

PCT Pub. Date: Aug. 1, 2002

(65) Prior Publication Data

US 2004/0078835 A1 Apr. 22, 2004

(30) Foreign Application Priority Data

Jan. 3, 2001 (GB) ................................. 0100119.7

(51) Int. Cl.
*G01N 33/00* (2006.01)
*A01K 67/00* (2006.01)
*A01K 67/033* (2006.01)
*A01K 67/027* (2006.01)
*C12N 15/00* (2006.01)

(52) U.S. Cl. ............................... 800/18; 800/3; 800/12; 800/14; 800/25

(58) Field of Classification Search ................... 800/12, 800/14, 18, 3, 25
See application file for complete search history.

(56) References Cited

U.S. PATENT DOCUMENTS

| 2,928,767 | A | 3/1960 | Gulesich et al. |
| 5,827,644 | A | 10/1998 | Floyd et al. |
| 5,898,094 | A | 4/1999 | Duff et al. |
| 5,912,410 | A | 6/1999 | Cordell et al. |
| 6,953,794 | B2 | 10/2005 | Wischik et al. |
| 2003/0217370 | A1 | 11/2003 | Giasson et al. |
| 2006/0014216 | A1 | 1/2006 | Wischik et al. |

FOREIGN PATENT DOCUMENTS

| CA | 2 370 212 A1 | 5/2000 |
| EP | 0 457 295 | 11/1991 |
| EP | 0 618 968 B1 | 10/1994 |
| EP | 0 737 671 A2 | 10/1996 |
| EP | 0 909 814 A2 | 4/1999 |
| EP | 0 911 390 A2 | 4/1999 |
| EP | 0 911 398 A2 | 4/1999 |
| JP | 2001-352860 | 6/2000 |
| WO | WO 89 03993 | 5/1989 |
| WO | WO 93 01348 | 2/1993 |
| WO | WO 93 03369 | 2/1993 |
| WO | WO 93 11231 | 6/1993 |
| WO | WO 95 05466 | 2/1995 |
| WO | WO 95/05601 | 2/1995 |
| WO | WO 96 03177 | 2/1996 |
| WO | WO 96 04915 | 2/1996 |
| WO | WO 96 05837 | 2/1996 |
| WO | WO 96 30766 | 10/1996 |
| WO | WO 99 62548 | 12/1999 |
| WO | WO 01 53340 | 7/2001 |
| WO | WO 01 95709 | 12/2001 |
| WO | WO 02/055720 A2 | 7/2002 |
| WO | WO 02/075318 A2 | 9/2002 |
| WO | WO 03/007933 A1 | 1/2003 |
| WO | WO 2005/030676 A1 | 4/2005 |
| WO | WO 2006/032879 A2 | 3/2006 |

OTHER PUBLICATIONS

Nacharaju, Parimala, et al., Accelerated filament formation from tau protein with specific FTDP-17 missense mutations, FEBS Letters 447 (1999)195-199, Jacksonville, FL.

Spillantini, Maria Grazia, et al., "Mutation in the tau gene in familial multiple system tauopathy with presenile dementia," *Proc. Natl. Acad. Sci. USA*, vol. 95, Jun. 1998, pp. 7737-7741.

Yoshida, Hirotaka, et al., "Functional effects of *tau* gene mutations Δand N296H," *J. of Neurochemistry*, 2002, 80, 548-551, Cambridge, UK.

R. Lai, "The role of abnormal phosphorylation of tau protein in the development of neurofibrillary pathology in Alzheimer's disease", Christ's College, 1994, pp. 1-243.

C. Wischik, "Molecular neuropathology of Alzheimer's disease", 1989, pp. 44-70.

E. Montejo de Garcini, et al., "Self assembly of microtubule associated protein Tau into filaments resembling those found in Alzheimer disease", Biochemical and Biophysical Research Communications, 1986, pp. 790-797.

E. Montejo de Garcini, et al., "In vitro conditions for the self-polymerization of the microtubule-associated protein", J. Biochem., 1987, vol. 102, No. 6, pp. 1415-1421.

(Continued)

*Primary Examiner*—Valarie Bertoglio
(74) *Attorney, Agent, or Firm*—Foley & Lardner LLP

(57) ABSTRACT

Disclosed is a method of inducing or modeling a disease associated with pathological tau protein aggregation. The method can be carried out in vitro and animal models, and may be used to screen for therapeutic, prognostic or diagnostic agents.

30 Claims, 32 Drawing Sheets

OTHER PUBLICATIONS

Figure 1C:
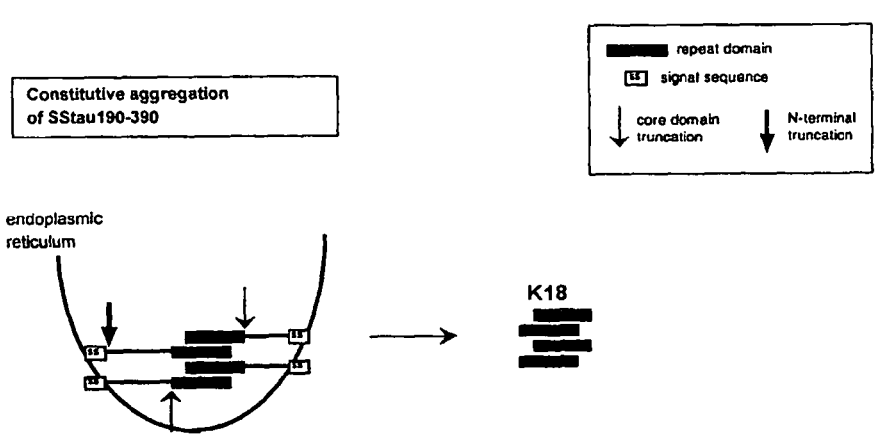

E. Montejo de Garcini, et al., "Tau factor polymers are similar to paired helical filaments of Alzheimer's disease", Elsevier Science Publishers B.V., 1988, pp. 150-154.

H. Ksiezak-Reding and S.H. Yen, "Structural stability of paired helical filaments requires microtubule-binding domains of tau: A model for self-association", Neuron, 1991, vol. 6, pp. 717-728.

U.S. Appl. No. 11/391,675, filed Mar. 29, 2006, C. M. Wischik, et al.

H. Wille, "Alzheimer-like paired helical filaments and antiparallel dimers formed from microtubule-associated protein tau in vitro", J. Cell Biol., 118, 1992, pp. 573-584.

H. Ksiezak-Reding.and J.S. Wall, "Mass and physical dimensions of two distinct populations of paired helical filaments", Neurobiology of Aging, 1994, vol. 15, No. 1, pp. 11-18.

C.M. Wischik, et al., "Isolation of a fragment of tau derived from the core of the paired helical filament of Alzheimer disease", Proc. Natl. Acad. Sci. USA, 1988, vol. 85, pp. 4506-4510.

C.M. Wischik, et al., "Structural characterization of the core of the paired helical filament of Alzheimer disease", Proc. Natl. Acad. Sci. USA, 1988, vol. 85, pp. 4884-4888.

C.M. Wischik, et al., "Selective inhibition of Alzheimer disease-like tau aggregation by phenothiazines", Proc. Natl. Acad. Scie. USA, 1996, vol. 93, pp. 11213-11218.

H. Ksiezak-Reding, "Assembled tau filaments differ from native paired helical filaments as determined by scanning transmission electron microscopy", STEM, 1998, pp. 86-98.

R. Mena, et al., "A progressive deposition of paired helical filaments (PHF) in the brain characterizes the evolution of dementia in Alzheimer's disease", Journal of Neuropathology and Experimental Neurology, 1991, pp. 474-490.

R. Mena, et al., "Monitoring pathological assembly of tau and β-amyloid proteins in Alzheimer's diesease", Acta Neuropathol, 1994, pp. 50-56.

R. Mena, et al., "Staging and pathological assembly of truncated tau protein into paired helical filaments in Alzheimer's disease", Acta Neuropathol, 1995, pp. 633-641.

C.M. Wischik, et al., "Quantitative analysis of tau protein in paired helical filament preparations" Implications for the role of tau protein phosphorylation in PHF assembly in Alzheimer's disease, Neurobiology of Aging, 1995, vol. 16, No. 3, pp. 409-431.

C.M. Wischik, et al., "Author's response to commentaries", Neurobiology of Aging, 1995, vol. 16, No. 3, pp. 423-431.

C.M. Wischik, et al., "Structure, biochemistry and molecular pathogenesis of paired helical filaments in Alzheimer's disease", Pathbiology of Alzheimer's Disease, 1995, pp. 10-39.

V.M.-Y. Lee et al., "A68: A major subunit of paired helical filaments and derivatized forms of normal tau", Science, 1991, vol. 251, pp. 675-678.

M. Goedert, et al., "Tau proteins of Alzheimer paired helical filaments: Abnormal phosphorylation of all six brain isoforms", Neuron, Jan. 1992, vol. 8, pp. 159-168.

R. Jakes, et al. "Identification of 3- and 4-repeat tau isoforms within the PHF is Alzheimer's disease", The EMBO Journal, 1991, vol. 10, No. 10, pp. 2725-2729.

M. Novak, et al., Molecular characterization of the minimal protease resistant tau unit of the Alzheimer's disease paired helical filament:, The EMBO Journal, 1993, vol. 12, No. 1, pp. 365-370.

S.-H. Yens, et al., "Alzheimer's neurofibrillary tangles contain unique epitopes in common with the heat-stable microtubule-associated proteins tau and MAP2", American Journal of Pathology, 1987, vol. 126, pp. 81-91.

J.-P. Brion, et al., "Characterization of a partial cDNA specific for the high molecular weight microtubule-associated protein MAP2 that encodes epitopes shared with pared helical filaments of Alzheimer's disease", Dementia, 1990, vol. 1, pp. 304-315.

M.W. Klymkowsky, "Weaving a tangled web: the interconnected cytoskeleton", Nature Cell Biology, 1999, vo. 1, No. 5, p. E121.

R. Brandt, "Cytoskeletal mechanisms of axon outgrowth and pathfinding", Cell Tissue Res., 1998, vol. 292, 181-189.

D. van Rossum, et al., "Cytoskeletal dynamics in dendritic spines: direct modulation by glutamate receptors", Trends Neurosci., 1992, vol. 22, pp. 290-295.

R. Sato-Harada, et al., "Microtubule-associated Proteins Regulate Microtubule Function as the Track for Intracellular Membrane Organelle Transports", Cell Structure Function 21, 1996, pp. 283-295.

A. Grover, et al., "5' splice site mutations in tau associated with the inherited dementia FTDP-17 affect a stem-loop structure that regulates alternative splicing of Exon 10*", The Journal of Biological Chemistry, 1999, May 21 issue, vol. 274, No. 21, pp. 15134-15143.

M. Hutton, et al. "Association of missense and 5'-splice-site mutations in tau with the inherited dementia FTDP-17", Nature, Jun. 18, 1998, vol. 393, pp. 702-705.

T. Ishihara, et al., "Age-dependent emergence and progression of a tauopathy in transgenic mice overexpressing the shortest human tau isoforms", Neuron, Nov. 1999, vol. 24, pp. 751-762.

A. Harada, et al., "Altered microtubule organization in small-calibre axons of mice lacking tau protein", Letters to nature, Jun. 9, 1994, vol. 369, pp. 488-491.

R.Y.K. Lai, et al., "Examination of phosphorylated tau protein as a PHF-precursor at early state Alzheimer's diseases", Neurobiology of Aging, 1995, vol. 16, No. 3, pp. 433-445.

B.H. Anderton, et al., "Dendritic changes in Alzheimer's disease and factors that may underlie these changes", Prog. Neurobiol., Augu. 1998, 55(6), pp. 595-609.

P. Friedhoff, et al., "Rapid Assembly of Alzheimer-like paired helical filaments from microtubule-associated protein tai monitored by fluorescence in solution", Biochemistry, 1998, vol. 37, pp. 10223-10230.

P. Friedhoff, et al., "A nucleated assembly mechanism of Alzheimer paired helical filaments", Proc. Natl. Acad. Sci., USA, Dec. 1998, vol. 95, pp. 15712-15717.

B. Pedrotti, et al., "Interactions of microtubule-associated protein MAP2 with unpolymerized and polymerized tubulin and actin using a 96-well microtiter plate solid-phase immunoassay", Biochemistry, 1994, vol. 33, pp. 8798-8806.

J. Garcia de Ancos, et al., "Differences in microtubule binding and self-association abilities of bovine brain tau isoforms", The Journal of Biological Chemistry, 1993, vol. 268, No. 11, pp. 7976-7982.

C. Smith, et al., "The molecular pathology of Alzheimer's disease: are we any closer to understanding the neurodegenerative process?", Neuropathology and Applied Neurobiology, 1994, vol. 20, pp. 322-338.

C.R. Harrington, et al., "Measurement of distinct immunochemical presentations of tau protein in Alzheimer's disease", Proc. Natl. Acad. Sci., Jul. 1991, vol. 88, pp. 5842-5846.

C.R. Harrington, et al., "Competitive ELISA for the measurement of tau protein in Alzheimer's disease", Journal of Immunological Methods, 1990, vol. 134, pp. 261-271.

C.M. Wischik, Thesis "The structure and biochemistry of paired helical filaments in Alzheimer's disease", Part I and II, pp. 1-455, 1989.

C.M. Wischik, et al., "Subunit structure of paired helical filaments in Alzheimer's disease". The Journal of Cell Biology, 1985, vol. 100, pp. 1905-1912.

J.L. Martinez, et al., "Methylene blue alters retention of inhibitory avoidance responses", Physiol. Psychol., 1978, vol. 6(3), pp. 387-390.

M. von Bergen, et al. "Assembly of tau protein into Alzheimer's paired helical filaments depends on a local sequence motif forming beta structure", Proceedings of the National Academy of Sciences of USA, National Academy of Science, May 9, 2000, vol. 97, No. 10, pp. 5129-5134.

O. Condamines, et al., "New immunoassay for the mapping of neurofibrillary degeneration in Alzheimer's disease using two monoclonal antibodies against human paired helical filament tau proteins", Neuroscience Letters, Jun. 9, 1995, vol. 192, No. 2, pp. 81-84.

Luisa Fasulo, et al., "Overexpression of Alzheimer's PHF core tau fragments: implications for the tau truncation hypothesis", Alzheimer's Research 2, 1996, pp. 195-200.

V.M.-Y Lee, et al., "Tau proteins and their significance in the pathology of Alzheimer's disease", Pathobiology of Alzheimer's Disease, pp. 41-58, 1995.

C.M. Wischik, et al., "The role of tau protein in the neurodegenerative dementias", Dementia 2nd edition, pp. 461-492, J (EDT)/Ames D (EDT)/Burns, A (EDT)/Levy, R/Publisher: Hodder Arnold Published 2001/02.

C.M. Wischik, et al., "Modelling prion-like processing of tau protein in Alzheimer's disease for pharmaceutical development", 1997, Harwood Acad. Publishers, pp. 185-241.

J. Gotz, et al., "Tau filaments formation in transgenic mice expressing P301L tau", J. Biol. Chem., Jan. 5, 2001, vol. 276(1), pp. 529-534.

M. Thunecke, et al., "Motor deficits in transgenic mice expressing human tau cDNA constructs", 1996.

K.A. Partridge, et al. "Competition between the signal sequence and a 3'UTR localisation signal during redirection of beta-globin mRNA to the endoplasmic reticulum: implications for biotechnology", Cytotechnology, 1999, vol. 30, pp. 37-47.

J. Lewis, et al., "Neurofibrillary tangles, amyotrophy and progressive motor disturbance in mice expressing mutant (P301L) tau protein", Nature Genetics, vol. 25, No. 4, pp. 402-405, 2000.

T. Arendt, et al., "Paired helical filament-like phosphorylation of tau, deposition of β/A4-amyloid and memory impairment in rat induced by chronic inhibition of phosphatase 1 and 2a", Neuroscience, 1995, vol. 69, No. 3, pp. 691-698.

K. Duff, et al., "Characterization of pathology in transgenic mice overexpressing human genomic and cDNA tau transgenes", Neurobiology of Disease 7, 2000, pp. 87-98.

C. Janus, et al., "Transgenic mouse models of Alzheimer's disease", Elsevier Science, 2000, pp. 63-75.

C. Sturchler-Pierrat, et al., "Two amyloid precursor protein transgenic mouse models with Alzheimer disease-like pathology", Proc. Natl. Acad. Sci. USA, Nov. 1997, vol. 94, pp. 13287-13292.

J.P. Brion, et al., "Transgenic expression of the shortest human tau affects its compartmentalization and its phosphorylation as in the pretangle stage of Alzheimer's disease", American Journal of Pathology, vol. 154, No. 1, Jan. 1999, pp. 255-269.

K. Spittaels, et al., "Prominent axonopathy in the brain and spinal cord of transgenic mice overexpressing four-repeat human tau protein", American Journal of Pathology, vol. 155, No. 6, Dec. 1999, pp. 2153-2165.

S. Ikegami, et al., "Muscle weakness, hyperactivity, and impairment in fear conditioning in tau-deficient mice", Elsevier Science, 2000, vol. 279, pp. 129-132.

C. Geula, et al., "Aging renders the brain vulnerable to amyloid β-protein neurotoxicity", Nature Medicine, Jul. 1998, vol. 4, No. 7, pp. 827-834.

C. Schultz, et al., "Filamentous tau pathology in nerve cells, astrocytes, and oligodendrocytes of aged baboons", Journal of Neuropathology and Experimental Neurology, Jan. 2000, vol. 59, No. 1,, pp. 39-52.

L.C. Cork, et al., "Neurofibrillary tangles and senile plaques in aged bears", Journal of Neuropathology and Experimental Neurology, Nov. 1988, vol. 47, No. 6, pp. 629-641.

K.E. Roertgen, et al., "Aβ-associated cerebral angiopathy and senile plaques with neurofibrillary tangles and cerebral hemorrhage in an aged wolverine (Gulo gulo)", Neurobiology of Aging, 1996, vol. 17, No. 2, pp. 243-247.

E.B. Mukaetova-Ladinska, et al., "α-Synuclein Inclusions in Alzheimer and Lewy body disease", Journal of Neuropathology and Experimental Neurology, May 2000, vol. 59, No. 5, pp. 408-417.

L.A. Cudd, et al., "Pharmacokinetics and toxicity of tolonium chloride in sheep", Vet Human Toxicol, Oct. 1996, vol. 38, No. 5, pp. 329-334.

M. Kiese, et al., "Comparative studies on the effects of toluidine blue and methylene blue on the reduction of ferrihaemoglobin in man and dog", Europ. J. Clin. Pharmacol., 1972, vol. 4, pp. 115-118.

W.L. Rumbolz, et al., "Use of protamine sulfate and toluidine blue for abnormal uterine bleeding", Am. J. Obst. & Gynec., May 1952, vol. 63, No. 5, pp. 1029-1037.

J.E. Holoubek, et al., "Toluidine blue in bleeding associated with thrombopenia", J.A.M.A., Jan. 22, 1949, vol. 139, No. 4, pp. 214-216.

J.G. Allen, et al., "Further clinical experience with toluidine blue and protamine sulfate", Abnormal Bleeding II, pp. 692-703.

A. Mashberg, "Tolonium (Toluidine blue) rinse—a screening method for recognition of squanous carcinoma—continuing study of oral-caneer 4", Jama-Journal of the American Medical Association, vol. 245, No. 23, pp. 2408-2410, 1981.

J. Perez-Tur, et al., "Neurodegenerative disease of Guam: Analysis of Tau", American Academy of Neurology, 1999, vol. 53, pp. 411-412.

C.M. Wischik, "Cell biology of the Alzheimer tangle", Current Opinion in Cell Biology, 1989, vol. 1, pp. 115-122.

T. Muller, "Light-microscopic demonstration of methylene blue accumulation sites in mouse brain after supravital staining", Acta Anat., 1992, vol. 144, pp. 39-44.

C. Bancher, et al., "Accumulation of abnormally phosphorylated τ precedes the formation of neurofibrillary tangles in Alzheimer's disease", Brain Research, 1989, vol. 477, pp. 90-99.

K. Ishiguro, et al., "A serine/threonine proline kinase activity is included in the tau protein kinase fraction forming a paired helical filament epitope", Neuroscience Letters, 1991, vol. 128, pp. 195-198.

K. Ishiguro, et al.. "Tau protein kinase I converts normal tau protein into A68-like component of paired helical filaments", Journal of Biological Chemistry, 1992, vol. 267, pp. 10897-10901.

H. Aizawa, et al., "Microtubule-binding domain of tau proteins", Journal of Biological Chemistry, 1988, vol. 263, pp. 7703-7707.

M.D. Ledesma, et al., "Implication of brain cdc2 and MAP2 kinases in the phosphorylation of tau protein in Alzheimer's disease", FEBS, 1992, vol. 308, No. 2, pp. 218-224.

M. Goedert, et al., "Cloning and sequencing of the cDNA encoding a core protein of the paired helical filament of Alzheimer disease: Identification as the microtubule-associated protein tau", Proc. Natl. Acad. Sci. USA, Jun. 1988, vol. 85, pp. 4051-4055.

B. Lichtenberg-Kraag, et al., "Phosphorylation-dependent epitopes of neurofilament antibodies on tau protein and relationship with Alzheimer tau", Proc. Natl. Acad. Sci. USA, 1992, vol. 89, pp. 5384-5388.

J. Biernat, et al., "The switch of tau protein to an Alzheimer-like state includes the phosphorylation of two serine-proline motifs upstream of the microtubule binding region", EMBO Journal 11, 1992, pp. 1593-1597.

B. Lichtenberg-Kraag, et al., "Alzheimer-type phosphorylation of microtubule-associated protein tau in vitro", 1991/92, abstract only.

K. Ishiguro, et al., "A novel tubulin-dependent protein kinase forming a paired helical filament epitope on tau", J. Biochem, 1988, vol. 104, pp. 319-321.

K. Ishiguro, et al., "Phosphorylation sites on tau by tau protein kinase I, a bovine derived kinase generating an epitope of paired helical filaments", Neuroscience Letters, 1992, vol. 148, pp. 202-206.

T. Hagestedt, et al., "Tau protein becomes long and stiff upon phosphorylation: correlation between paracrystalline structure and degree of phosphorylation", The Journal of cell biology, 1989, vol. 109, pp. 1643-1651.

S.A. Lewis, et al., "Microtubule-associated protein MAP2 shares a microtubule binding motif with tau protein", Science, 1988, vol. 242, pp. 936-939.

A. Schneider, et al., "Phosphorylation that detaches tau protein from microtubules (Ser262, Ser214) also protects it against aggregation into Alzheimer paired helical filaments", Biochemistry, 1999, vol. 38, pp. 3549-3558.

C.B. Caputo, et al., "The amyloid proteins of Alzheimer's disease as potential targets for drug therapy", Neurobiology of Aging, vol. 10, pp. 451-461, 1989.

C.B. Caputo, et al., "Amyloid-like properties of a synthetic peptide corresponding to the carboxy terminus of β-amyloid protein precursor", Archives of Biochemistry and Biophysics, 1992, vol. 292, pp. 199-205.

D.A. Lomas, et al., "The mechanism of Z α1-antitrypsin accumulation in the liver", Nature, 1992, vol. 357, pp. 605-607.

S. Janciauskiene, et al., "In vitro amyloid fibril formulation from α1-antitrypsin", Bio Chem, 1995, vol. 375, pp. 103-109.

L. Poulter, et al., "Locations and immunoreactivities of phosphorylation sites on bovine and porcine tau proteins and a PHF-tau fragment", The Journal of Biological Chemistry, 1993, vol. 268, No. 13, pp. 9636-9644.

I. Grundke-Iqbal, et al.. "Abnormal phosphorylation of microtubule-associated protein T (tau) in Alzheimer cytoskeletal pathology", Proc. Natl. Acad. Sci. USA, 1986, vol. 83, pp. 4913-4917.

M. Perez, et al., "In vitro assembly of tau protein: Mapping the regions involved in filament formation", Biochemistry, 2001, vol. 40, 5983-5991.

A.M. Giannetti, et al., "Fibers of tau fragments, but not full length tau, exhibit a cross β-structure: implications for the formation of paired helical filaments", Protain Science, 2000, vol. 9, pp. 2427-2435.

M.A. DeTure, L. DiNoto, and D.L. Purich, "In vitro assembly of Alzheimer-like filaments. How a small cluster of charged residues in tau and MAP2 controls filament morphology", Journal of Biological Chemistry, 2002, vol. 277, pp. 34755-34759.

L. Varani, et al., "Structure of tau exon 10 splicing regulatory element RNA and destabilization by mutations of frontotemporal dementia and parkinsonism linked to chromosome 17", Proc. Natl. Acad. Sci. USA, 1999, vol. 96, pp. 8229-8234.

N.L. Callaway, et al., "Methylene blue restores spatial memory retention impaired by an inhibitor of cytochrome oxidase in rats", Neuroscience Letters, 2002, vol. 332, pp. 83-86.

A. Ito, et al., "Enhancing effect of ascorbate on toluidine blue-photosensitization of yeast cells", Photochemistry and Photobiology, 1982, vol. 35, pp. 501-505.

J.B. Epstein, et al., "The utility of toluidine blue application as a diagnostic aid in patients previously treated for upper oropharyngeal carcinoma", Oral medicine, 1997, vol. 83, No. 5, pp. 537-547.

A.M. Shojania, et al., "The effect of toluidine blue and methylene blue in immunochemical reactions in vitro", Clinical Immunology and Immunopathology, 1987, vol. 43, pp. 223-228.

C.M. Wischik, F. Theuring and C.R. Harrington, "The molecular basis of tau protein pathology in Alzheimer's disease and related neurodegenerative dementias", In Neurobiology of Alzheimer's Disease (Eds. D. Dawbarn & S.J. Allen) Oxford University Press, Oxford, pp. 103-206, 2001.

C. Wischik, "Molecular neuropathology of Alzheimer's disease", John Libbey & Co., 1991, pp. 239-250.

(a)
Seeding by SStau190-441 Induces Two Stage Degradation of T40 By Aggregation Through the PHF Core Domain. Production of 25 kd fragment
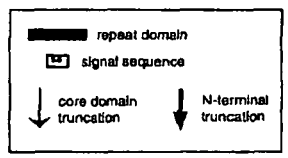
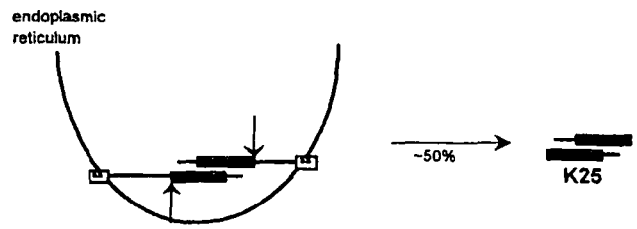
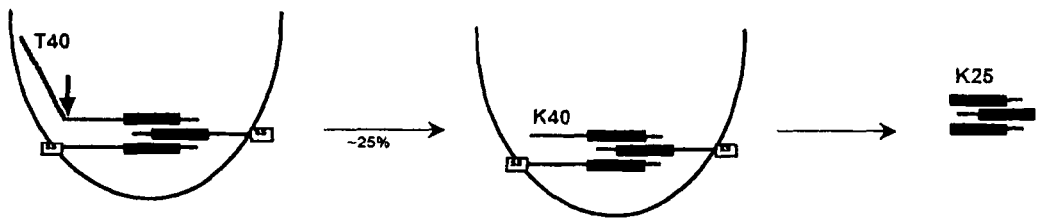
(b)
Aggregation of SStau190-441 Produces 30 kd, 18 kd and 12/14kd Fragments
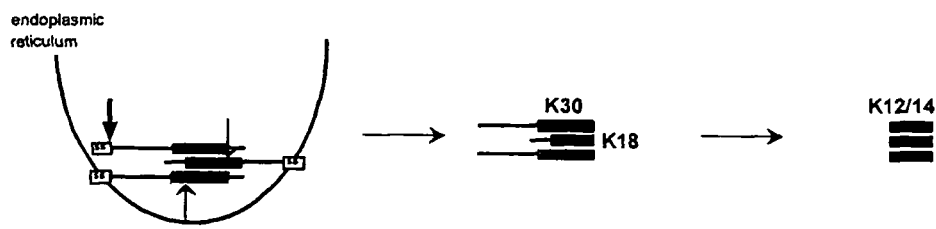
Figure 1A and 1B (c)

Aggregation of SStau190-390 Produces an 18 kd Fragment (d)

Aggregation of SStau296-390: Interaction with T40 Produces Two Possible 18 kd Fragments, and a 12/14 kd Fragment Activities of compounds in the
↑T40 + 40 kD ⇒ ↑25 kD cell assay
Results shown as relative production of 25 kD band

Thionine : memb-Tau model
↑T40 + 40 kD ⇒ ↑25 kD cell assay

Cellular activity predicted via standard inhibition model:

acitivity = [ tau ] / ([ tau ] + Kd * ( 1 + [ thionine ] / KI ))

| | | |
|---|---|---|
| Observed vs predicted activity | r = 0.999 | |
| Intracellular tau concentration | 415 | nM |
| Tau-tau binding affinity | 500 | nM |
| Thionine KI | 33 | nm |

Nucleotide Sequence (SEQ ID NO:1) and
Amino Acid Sequence (SEQ ID NO:2) of Human Tau Protein Isoform

```
ATG GCT GAG CCC CGC CAG GAG TTC GAA GTG ATG GAA GAT CAC GCT GGG ACG TAC GGG TTG
Met ala glu pro arg gln glu phe glu val met glu asp his ala gly thr tyr gly leu
1               5                   10                  15                  20
GGG GAC AGG AAA GAT CAG GGG GGC TAC ACC ATG CAC CAA GAC CAA GAG GGT GAC ACG GAC
gly asp arg lys asp gln gly gly tyr thr met his gln asp gln glu gly asp thr asp
                25                  30                  35                  40
GCT GGC CTG AAA GAA TCT CCC CTG CAG ACC CCC ACT GAG GAC GGA TCT GAG GAA CCG GGC
ala gly leu lys glu ser pro leu gln thr pro thr glu asp gly ser glu glu pro gly
                45                  50                  55                  60
TCT GAA ACC TCT GAT GCT AAG AGC ACT CCA ACA GCG GAA GAT GTG ACA GCA CCC TTA GTG
ser glu thr ser asp ala lys ser thr pro thr ala glu asp val thr ala pro leu val
                65                  70                  75                  80
GAT GAG GGA GCT CCC GGC AAG CAG GCT GCC GCG CAG CCC CAC ACG GAG ATC CCA GAA GGA
asp glu gly ala pro gly lys gln ala ala ala gln pro his thr glu ile pro glu gly
                85                  90                  95                  100
ACC ACA GCT GAA GAA GCA GGC ATT GGA GAC ACC CCC AGC CTG GAA GAC GAA GCT GCT GGT
thr thr ala glu glu ala gly ile gly asp thr pro ser leu glu asp glu ala ala gly
                105                 110                 115                 120
CAC GTG ACC CAA GCT CGC ATG GTC AGT AAA AGC AAA GAC GGG ACT GGA AGC GAT GAC AAA
his val thr gln ala arg met val ser lys ser lys asp gly thr gly ser asp asp lys
                125                 130                 135                 140
AAA GCC AAG GGG GCT GAT GGT AAA ACG AAG ATC GCC ACA CCG CGG GGA GCA GCC CCT CCA
lys ala lys gly ala asp gly lys thr lys ile ala thr pro arg gly ala ala pro pro
                145                 150                 155                 160
GGC CAG AAG GGC CAG GCC AAC GCC ACC AGG ATT CCA GCA AAA ACC CCG CCC GCT CCA AAG
gly gln lys gly gln ala asn ala thr arg ile pro ala lys thr pro pro ala pro lys
                165                 170                 175                 180
ACA CCA CCC AGC TCT GGT GAA CCT CCA AAA TCA GGG GAT CGC AGC GGC TAC AGC AGC CCC
thr pro pro ser ser gly glu pro pro lys ser gly asp arg ser gly tyr ser ser pro
                185                 190                 195                 200
GGC TCC CCA GGC ACT CCC GGC AGC CGC TCC CGC ACC CCG TCC CTT CCA ACC CCA CCC ACC
gly ser pro gly thr pro gly ser arg ser arg thr pro ser leu pro thr pro pro thr
                205                 210                 215                 220
CGG GAG CCC AAG AAG GTG GCA GTG GTC CGT ACT CCA CCC AAG TCG CCG TCT TCC GCC AAG
arg glu pro lys lys val ala val val arg thr pro pro lys ser pro ser ser ala lys
                225                 230                 235                 240
AGC CGC CTG CAG ACA GCC CCC GTG CCC ATG CCA GAC CTG AAG AAT GTC AAG TCC AAG ATC
ser arg leu gln thr ala pro val pro met pro asp leu lys asn val lys ser lys ile
                245                 250                 255                 260
GGC TCC ACT GAG AAC CTG AAG CAC CAG CCG GGA GGC GGG AAG GTG CAG ATA ATT AAT AAG
gly ser thr glu asn leu lys his gln pro gly gly gly lys val gln ile ile asn lys
                265                 270                 275                 280
AAG CTG GAT CTT AGC AAC GTC CAG TCC AAG TGT GGC TCA AAG GAT AAT ATC AAA CAC GTC
lys leu asp leu ser asn val gln ser lys cys gly ser lys asp asn ile lys his val
                285                 290                 295                 300
CCG GGA GGC GGC AGT GTG CAA ATA GTC TAC AAA CCA GTT GAC CTG AGC AAG GTG ACC TCC
pro gly gly gly ser val gln ile val tyr lys pro val asp leu ser lys val thr ser
                305                 310                 315                 320
AAG TGT GGC TCA TTA GGC AAC ATC CAT CAT AAA CCA GGA GGT GGC CAG GTG GAA GTA AAA
lys cys gly ser leu gly asn ile his his lys pro gly gly gly gln val glu val lys
                325                 330                 335                 340
TCT GAG AAG CTT GAC TTC AAG GAC AGA GTC CAG TCG AAG ATT GGG TCC CTG GAC AAT ATC
ser glu lys leu asp phe lys asp arg val gln ser lys ile gly ser leu asp asn ile
                345                 350                 355                 360
ACC CAC GTC CCT GGC GGA GGA AAT AAA AAG ATT GAA ACC CAC AAG CTG ACC TTC CGC GAG
thr his val pro gly gly gly asn lys lys ile glu thr his lys leu thr phe arg glu
```

Figure 5A

```
                365                 370                 375                 380
AAC GCC AAA GCC AAG ACA GAC CAC GGG GCG GAG ATC GTG TAC AAG TCG CCA GTG GTG TCT
asn ala lys ala lys thr asp his gly ala glu ile val tyr lys ser pro val val ser
                385                 390                 395                 400
GGG GAC ACG TCT CCA CGG CAT CTC AGC AAT GTC TCC TCC ACC GGC AGC ATC GAC ATG GTA
gly asp thr ser pro arg his leu ser asn val ser ser thr gly ser ile asp met val
                405                 410                 415                 420
GAC TCG CCC CAG CTC GCC ACG CTA GCT GAC GAG GTG TCT GCC TCC CTG GCC AAG CAG GGT
asp ser pro gln leu ala thr leu ala asp glu val ser ala ser leu ala lys gln gly
                425                 430                 435                 440
TTG TGA
leu ***
```

Figure 5A Continued square brackets     indicates signal sequence
bold     indicates tubulin-binding segments SStau186-441 (SEQ ID NO: 3)

[MKWVTFLLLLFISGSAFSPV]KSGDRSGYSSPGSPGTPGSRSRTPSLPTPP
TREPKKVAVVRTPPKSPSSAKSRLQTAPVPMPDLKNVKSKIGSTENLKHQP
GGGKVQIINKKLDLSNVQSKCGSKDNIKHVPGGGSVQIVYKPVDLSKVTSK
CGSLGNIHHKPGGGQVEVKSEKLDFKDRVQSKIGSLDNITHVPGGGNKKIE
THKLTFRENAKAKTDHGAEIVYKSPVVSGDTSPRHLSNVSSTGSIDMVDSP
QLATLADEVSASLAKQGL

SStau186-390 (SEQ ID NO: 4)

[MKWVTFLLLLFISGSAFSPV]KSGDRSGYSSPGSPGTPGSRSRTPSLPTPP
TREPKKVAVVRTPPKSPSSAKSRLQTAPVPMPDLKNVKSKIGSTENLKHQP
GGGKVQIINKKLDLSNVQSKCGSKDNIKHVPGGGSVQIVYKPVDLSKVTSK
CGSLGNIHHKPGGGQVEVKSEKLDFKDRVQSKIGSLDNITHVPGGGNKKIE
THKLTFRENAKAKTDHGA

SStau296-390 (SEQ ID NO: 5)

[MKWVTFLLLLFISGSAFSPV]NIKHVPGGGSVQIVYKPVDLSKVTSKCGSLG
NIHHKPGGGQVEVKSEKLDFKDRVQSKIGSLDNITHVPGGGNKKIETHKLTF
RENAKAKTDHGA

Figure 5B

Sequence Differences in the Tandem Repeat Region of
Human Tau (SEQ ID NO:6) and Human MAP2 (SEQ ID NO:7)

Figure 8 full-length tau
(tau40)
SStau296-390
SStau190-441
SStau190-390
tau186-441
tau186-391
 PHF core domain
 signal sequence
Figure 10

S1 fraction from three different mice of line 1 show 18kD

*In vitro* aggregation of bacterially expressed dGAE (a)
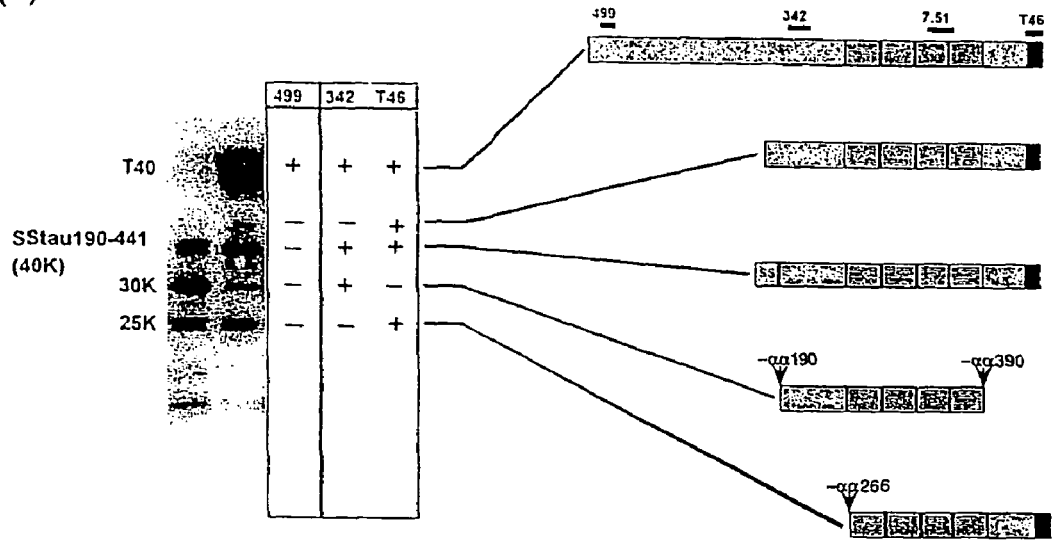
(b)
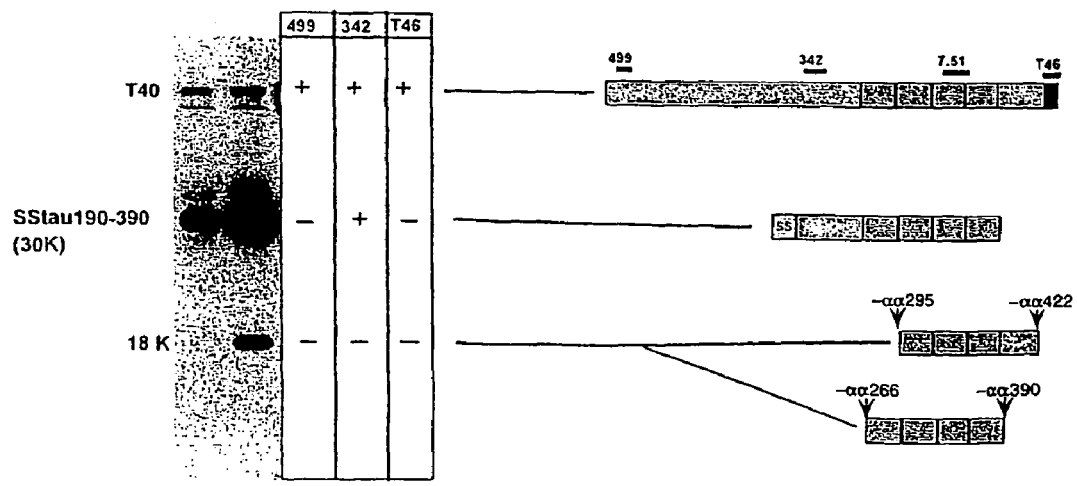
Figure 17

Diseases of protein aggregation

| Protein | Disease | Aggregating domain and/or mutations | Fibril subunit size (kDa) | Reference |
|---|---|---|---|---|
| *Neurodegenerative disorders* | | | | |
| Prion protein | Prion diseases (CJD, nvCJD, Fatal familial insomnia, Gerstmann-Straussler-Scheinker syndrome, Kuru) | *Inherited and sporadic forms* PrP-27-30; many mutations Fibrilogenic domains: 113-120, 178-191, 202-218 | 27 | Prusiner (1998) Gasset et al. (1992) |
| Tau protein | Alzheimer's disease, Down's syndrome, FTDP-17, CBD, post-encephalitic parkinsonism, Pick's disease, parkinsonism with dementia complex of Guam | *Inherited and sporadic forms* Truncated tau (tubulin-binding domain) 297-391 Mutations in tau in FTDP-17 Many mutations in presenilin proteins | 10-12 | Wischik et al. (1988) Hutton et al. (1998) Czech et al. (2000) |
| Amyloid β-protein | Alzheimer's disease, Down's syndrome | *Inherited and sporadic forms* Amyloid β-protein; 1-42(3); 11 mutations in APP in rare families | 4 | Glenner & Wong, (1984) Goate et al. (1991) |
| Huntingtin Ataxins (1, 2, 3, 7) Atrophin Androgen receptor | Huntington's disease Spinocerebellar ataxias (SCA1, 2, 3, 7) Dentarubropallidoluysian atrophy (DRPLA) Spinal and bulbar muscular atrophy | N-termini of protein with expanded glutamine repeats Proteins with expanded glutamine repeats Proteins with expanded glutamine repeats Proteins with expanded glutamine repeats | 40 | DiFiglia et al. (1997) Paulson et al. (2000) Paulson et al. (2000) Paulson et al. (2000) |
| Neuroserpin | Familial encephalopathy with neuronal inclusion bodies (FENIB) | Neuroserpin; S49P, S52R | 57 | Davis et al. (1999) |
| α-Synuclein | Parkinson's disease, dementia with Lewy bodies, multiple system atrophy | *Inherited and sporadic forms* A53T, A30P in rare autosomal-dominant PD families | 19 | Spillantini et al. (1998) Polymeropoulos et al. (1997) |
| Cystatin C | Hereditary cerebral angiopathy (Icelandic) | Cystatin C less 10 residues; L68Q | 12-13 | Abrahamson et al. (1992) |
| Superoxide dismutase 1 | Amyotrophic lateral sclerosis | SOD1 mutations | | Shibata et al. (1996) |
| *Non-neurodegenerative disorders* | | | | |
| Haemoglobin | Sickle cell anaemia Inclusion body haemolysis | Haemoglobin beta chain (S) Many mutations | | Carrell & Gooptu (1998) |
| Serpins | α1-Antitrypsin deficiency (emphysema, cirrhosis) Antithrombin deficiency (thromboembolic disease) C1-inhibitor deficiency (angioedema) | Mutations Mutations Mutations | | Lomas et al. (1992) Carrell & Gooptu (1998) Carrell & Gooptu (1998) |
| Immunoglobulin light chain | Plasma cell dyscrasias (primary systemic AL amyloidosis) | light chain or fragments | 0.5-25 | Westermark et al. (1985) |
| Serum amyloid A | Reactive, secondary systemic AA amyloidosis Chronic inflammatory disease | Variable N-terminal fragments of SAA | 4.5-10 | Westermark et al. (1985) |

(continued..........)

Figure 20

(............continued)

| | | | |
|---|---|---|---|
| Transthyretin | Familial amyloid polyneuropathy (systemic; FAP I) | Tetramer dissociated to conformational monomer variant. Many mutations (some not associated with amyloid; several different types of disease) | 10-14 | Gustavsson et al. (1991) |
| | Senile cardiac amyloidosis | Normal transthyretin | 10-14 | Gustavsson et al. (1991) |
| Gelsolin | Familial amyloidosis - Finnish type (FAP IV) | D187Q leads to truncated 173-225/243 (critical residues 182-192) | 9.5 | Maury & Baumann (1990) |
| β2-Microglobulin | Haemodialysis amyloidosis Prostatic amyloid | β2-Microglobulin | 12-25 | Gorevic et al. (1985) |
| Apolipoprotein AI | Familial amyloid polyneuropathy (systemic; FAP III) | N-terminal 83-93 residues; G26R, W50R, L60R | 9 | Booth et al. (1995) |
| Lysozyme | Familial visceral amyloidosis | Lysozyme or fragments (with or without I56T, D67H) | 14 | Pepys et al. (1993) |
| Amylin (Islet amyloid polypeptide) | Type II diabetes (NIDDM) | Fragments (critical core of 20-29); no mutations | 3.9 | Westermark (1990) |
| Fibrinogen α-chain | Hereditary renal amyloidosis | Fibrinogen fragments | 7-10 | Uemichi et al. (1994) |
| Procalcitonin | Medullary carcinoma of thyroid | Calcitonin fragments | 3.4 | Sletten et al. (1976) |
| Atrial natriuretic factor | Cardiac amyloidosis | ANF, no mutants | 3.5 | Johansson et al. (1987) |
| Insulin | Injection localised amyloidosis | Insulin | | Dische et al. (1988) |
| Other proteins forming amyloid | (in vitro) | Other proteins | | Chiti et al. (1999) |

Figure 20 cont ...

| Gel Mobility (kD) | Yield (µg) | Proteins Identified | 1 | 2 | 3 | 4 | 5 | 6 | 7 | 8 | 9 | 10 | 11 | 12 | 13 | 14 | 15 | 16 | 17 | 18 | 19 | 20 | |
|---|---|---|---|---|---|---|---|---|---|---|---|---|---|---|---|---|---|---|---|---|---|---|---|
| 46/44 | 2.3 | PHF-tau ubiquitin | Q²⁶⁹ | P | G | G | G | K | V | Q | I | V | Y | P²⁸¹ | | | | | | | | | Q²⁶⁹ to Y is SEQ ID NO: 20 |
| | | | | | F² | V | | T | L⁷ | | | | | | | | | | | | | | |
| 34/32 | 7.2 | PHF-tau ubiquitin porin " " " " | Q²⁶⁹ A¹ D²⁹ N¹³³ | P V L F | G P K E | G T T | G Y K | K D E¹⁹ | V L | V G¹⁰ | I | V | Y | P²⁸¹ | | | | | | | | | Q²⁶⁹ to V is SEQ ID NO: 21  D²⁹ to K is SEQ ID NO: 22 |
| | | | | | F² | V | | T | L⁷ | | | | | | | | | | | | | | |
| 26/24 | 7.9 | PHF-tau ubiquitin core-2 | Q²⁶⁹ G¹⁶ | P A | G P | G P | G Q | K D | V L | Q E | I F | V T | Y K | K L | P²⁸¹ P | A¹⁶ | | V¹⁷ G²¹ | | | | | | Q²⁶⁹ to P²⁸¹ is SEQ ID NO: 23  G¹⁶ to P is SEQ ID NO: 24 |
| 20/18 | 1.7 | subunit 9 | D¹ | I | D | A | K | | I | | A | | | | | | | | | | | | | |
| 14/12 | 4.0 | PHF-tau | H²⁶⁸ | Q/V | P | G | G | G | K/S | V | Q | I | V/I | Y | K | P | V | D | L | S | K | V²⁸⁷ | H²⁶⁸ to V²⁸⁷ is SEQ ID NO: 25 |
| 5 | | Aβ " " " subunit-9 | R¹ H⁶ Y¹⁰ I² | H D E E T | D S V V A | S G H A A | G Y H | Y E Q L K | E V L F¹⁹ F¹⁹ | V H | H Q I | H L | Q K G | K L A | L V | V F | F F | F A | A²¹ | G¹⁷ | | | | D V²⁴ | R⁵ to A is SEQ ID NO: 26  H⁶ to V is SEQ ID NO: 27  Y¹⁰ to H is SEQ ID NO: 28  F to A is SEQ ID NO: 29 |
| Pellet | 2.6 | PHF-tau ubiquitin subunit 9 | P²⁷⁰ I² | F² D | V T | A | A | K | F | I | G | A | G | A | A | T | V¹⁶ | D³¹³ | | | | | | V to D²⁸³ is SEQ ID NO: 30  I² to V¹⁶ is SEQ ID NO: 31 |
| TOTAL | 25.7 | | | | | | | | | | | | | | | | | | | | | | | |

Figure 21

MATERIALS AND METHODS RELATING TO PROTEIN AGGREGATION IN NEURODEGENERATIVE DISEASE

This application is the National Phase Application of International Application PCT/GB02/00005 filed on Jan. 2, 2002.

TECHNICAL FIELD

The present invention concerns models, materials and methods relating to the aggregation of proteins associated with neurodegenerative disease.

BACKGROUND ART

Conditions of dementia such as Alzheimer's disease (AD) are frequently characterised by a progressive accumulation of intracellular and/or extracellular deposits of proteinaceous structures such as β-amyloid plaques and neurofibrillary tangles in the brains of affected patients. The appearance of these lesions largely correlates with pathological neurofibrillary degeneration and brain atrophy, as well as with cognitive impairment (Mukaetova-Ladinska, E. B. et al. (2000) Am. J. Pathol. Vol. 157, No. 2, 623-636).

Both neuritic plaques and neurofibrillary tangles contain paired helical filaments (PHFs), of which a major constituent is the microtubule-associated protein tau (Wischik et al. (1988) PNAS USA 85, 4506). Plaques also contain extracellular β-amyloid fibrils derived from the abnormal processing of amyloid precursor protein (APP; Kang et al. (1987) Nature 325, 733). An article by Wischik et al. (in "Neurobiology of Alzheimer's Disease", 2nd Edition (2000) Eds. Dawbarn, D. and Allen, S. J., The Molecular and Cellular Neurobiology Series, Bios Scientific Publishers, Oxford) discusses in detail the putative role of tau protein in the pathogenesis of neurodegenerative dementias.

Studies of Alzheimer's disease indicate that the loss of the normal form of tau (Mukaetova-Ladinska et al. (1993) Am. J. Pathol., 143, 565; Wischik et al. (1995a) Neurobiol. Ageing, 16: 409; Lai et al. (1995b) Neurobiol. Ageing, 16: 433), accumulation of pathological PHFs (Mukaetova-Ladinska et al. (1993), loc. cit.; Harrington et al. (1994a) Dementia, 5, 215; Harrington et al. (1994b) Am. J. Pathol., 145, 1472; Wischik et al., (1995a), loc. cit.) and loss of synapses in the mid-frontal cortex (Terry et al. (1991) Ann. Neurol., 30, 572) correlate with associated cognitive impairment. Furthermore, loss of synapses (Terry et al., loc. cit.) and loss of pyramidal cells (Bondareff et al. (1993) Arch. Gen. Psychiatry, 50: 350) both correlate with morphometric measures of tau-reactive neurofibrillary pathology, which parallels, at a molecular level, an almost total redistribution of the tau protein pool from a soluble to a polymerised form (PHFs) in Alzheimer's disease (Mukaetova-Ladinska et al. (1993), loc. cit.; Lai et al. (1995), loc. cit.).

Tau exists in alternatively-spliced isoforms, which contain three or four copies of a repeat sequence corresponding to the microtubule-binding domain (Goedert, M., et al. (1989) EMBO J. 8, 393-399; Goedert, M., et al. (1989) Neuron 3, 519-526). Tau in PHFs is proteolytically processed to a core domain (Wischik, C. M., et al. (1988) Proc. Natl. Acad. Sci. USA 85, 4884-4888; Wischik et al. PNAS USA 1988, 85:4506-4510); Novak, M., et al. (1993) EMBO J. 12, 365-370) which is composed of a phase-shifted version of the repeat domain; only three repeats are involved in the stable tau-tau interaction (Jakes, R., et al. (1991) EMBO J. 10, 2725-2729). Once formed, PHF-like tau aggregates act as seeds for the further capture and provide a template for proteolytic processing of full-length tau protein (Wischik et al. 1996 Proc Natl Acad Sci USA 93, 11213-11218).

Figure 4A:
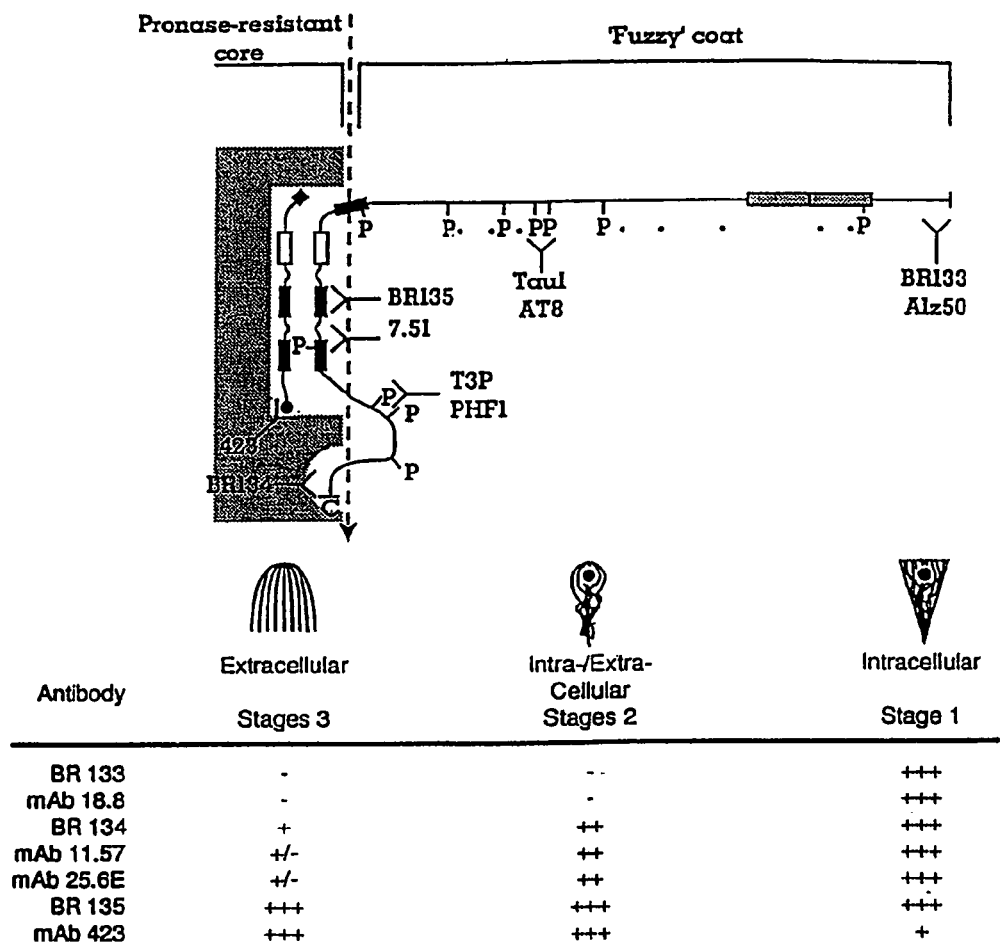

In the course of their formation and accumulation, paired helical filaments (PHFs) first assemble to form amorphous aggregates within the cytoplasm, probably from early tau oligomers which become truncated prior to, or in the course of, PHF assembly (Mena, R., et al. (1995) Acta Neuropathol. 89, 50-56; Mena, R., et al. (1996) Acta Neuropathol. 91, 633-641). These filaments then go on to form classical intracellular neurofibrillary tangles. In this state, the PHFs consist of a core of truncated tau and a fuzzy outer coat containing full-length tau (Wischik, C. M., et al. (1996b) in "Microtubule-associated proteins: modifications in disease", eds. Avila, J., Brandt, R. and Kosik, K. S. (Harwood Academic Publishers, Amsterdam) pp.185-241)). The assembly process is exponential, consuming the cellular pool of normal functional tau and inducing new tau synthesis to make up the deficit (Lai, R. Y. K., et al., (1995), Neurobiology of Ageing, Vol. 16, No. 3, 433-445). Eventually, functional impairment of the neurone progresses to the point of cell death, leaving behind an extracellular tangle. Cell death is highly correlated with the number of extracellular tangles (Wischik et al. 2000, loc.cit). As tangles are extruded into the extracellular space, there is progressive loss of the fuzzy outer coat of the neurone with corresponding loss of N-terminal tau immunoreactivity, but preservation of tau immunoreactivity associated with the PHF core (FIG. 4a; also Bondareff, W. et al., (1994) J. Neuropath. Exper. Neurol., Vol. 53, No. 2, 158-164).

The phase shift which is observed in the repeat domain of tau incorporated into PHFs suggests that the repeat domain undergoes an induced conformational change during incorporation into the filament. During the onset of Alzheimer's disease, it is envisaged that this conformational change could be initiated by the binding of tau to a pathological substrate, such as damaged or mutated membrane proteins (see FIG. 19a—also Wischik, C. M., et al. (1997) in "Microtubule-associated proteins: modifications in disease", eds. Avila, J., Brandt, R. and Kosik, K. S. (Harwood Academic Publishers, Amsterdam) pp.185-241).

In the case of Alzheimer's disease, current pharmaceutical therapies are focused on symptomatic treatment of the loss of cholinergic transmission which results from neurodegeneration (Mayeux, R., et al. (1999) New Eng. J. Med. 341, 1670-1679). However, although the available treatments delay progression of the disease for up to six to eight months, they do not prevent it. The discovery of drugs that could prevent the aggregation of tau which leads to neurodegeneration would provide a more effective strategy for prophylaxis or for inhibiting the progression of the disease, which would not require an immediate knowledge of the diverse upstream events that initiate the aggregation (FIG. 19b)

Protein Aggregation Assays

Based on the putative model described above, WO 96/30766 describes an in vitro assay for tau aggregation in which a fragment of tau corresponding to the core repeat domain, which has been adsorbed to a solid phase substrate, is able to capture soluble full-length tau and bind tau with high affinity. This association confers stability against proteolytic digestion of the aggregated tau molecules. The process is self-propagating, and can be blocked selectively by prototype pharmaceutical agents (Wischik, C. M., et al. (1996), loc. cit).

Although the in vitro assay described in WO 96/30766 enables the identification of inhibitors or modulators of tau-tau association, the present inventors have also recognized that cell-based models of Alzheimer's disease-like protein aggregation would be useful. Such cellular models could be used both in the primary screening of candidate modulators of tau-tau aggregation, and in the secondary screening of compounds already identified in the in vitro assay of WO 96/30766. Furthermore, the demonstration of tau aggregation in cells could also aid in the identification of normal cellular substrates which are involved in the initiation of pathological tau aggregation, which substrates could themselves be targets for pharmaceutical intervention.

However, numerous papers reporting the expression of various tau constructs in tissue culture models have failed to demonstrate aggregation (see e.g. Baum, L. et al., (1995) Mol. Brain Res. 34:1-17).

These problems can be understood when it is considered that aggregation of soluble tau in vitro has so far only been achieved under non-physiological conditions and at high concentrations (reviewed in Wischik (2000), loc. cit).

Wo 96/30766 also describes two approaches for studying tau aggregation in a cellular environment. In the first approach, full-length tau or fragments of tau were stably expressed in cells. In the second approach, aggregated tau was transiently transfected into cells by use of lipofectin.

Although both of these approaches are useful for the study of tau-tau aggregation, they have some limitations. Transfection of aggregated tau into cells using lipofection is of variable efficiency, as is the production of aggregated tau itself. Moreover, the core tau fragment, which is the most efficient seed for tau aggregation, is found to be toxic when stably expressed in cells, leading to low expression levels. Thus, constitutive expression of the truncated tau fragment of the PHF core in eukaryotic cells is difficult to achieve. Transient expression systems permit the optimization of expression of tau, but the inherent toxicity of the fragments renders even these systems unreliable. Longer fragments of tau are less toxic, but these do not reliably aggregate when expressed in cells.

Thus it would be desirable for an alternative model system to be developed, in which the interaction between e.g. tau molecules and the like could be investigated under physiological conditions, in a stable and controllable cell line, and which could be used to screen for potential diagnostic, prognostic or therapeutic agents of conditions such as Alzheimer's disease.

Animal Models

Although in vitro and cell-based assays can be useful tools, animal models of Alzheimer's disease and related conditions can help to understand the relationship between the biochemical and pathological changes in the brain and impairment of memory and behavior. Furthermore, they enable the pathogenesis of the disease process to be examined in vivo and provide a model in which therapeutic strategies can be tested.

Specifically, animal models put cell-based systems in a pharmacokinetic context where, for example, potential therapeutics can be assessed not just in terms of particular biochemical activities against protein aggregation, but also in terms of toxicity, delivery and half-life at the site of action e.g. through the blood brain barrier.

Notwithstanding this, existing models fail to display the combination of tangles, plaques and cognitive impairment characteristic of AD. Aged dogs and non-human primates develop β-amyloidosis, but tau pathology is not a feature in these animals (Walker, 1997). Similarly, transgenic mice modeling amyloidosis have been created, but these fail to exhibit abnormal deposition of tau (Janus, Chishti, & Westaway, 2000). Conversely animal models of tau pathology fail to demonstrate amyloid pathology. The tangles that accumulate in the brains of rodents treated with aluminium differ in their ultrastructure from those found in AD (see above). Filamentous cytoskeletal changes associated with abnormally phosphorylated tau have been observed in aged baboons, bears, sheep and goats (Braak, Braak, & Strothjohann, 1994; Cork et al., 1988; Nelson, Greenberg, & Saper, 1994; Nelson & Saper, 1995; Roertgen et al., 1996; Schultz et al., 2000).

Some experiments have implicated links between tau and amyloid in animal models. Hyperphosphorylated tau accumulates in the somatodendritic compartment of neurons in rat brains following chronic intraventricular infusion of okadaic acid, an inhibitor of protein phosphatase 2A (Arendt, Holzer, Fruth, Brijckner, & Gartner, 1995). Furthermore, the okadaic acid treatment also led to the formation of extracellular deposits of Aβ and memory impairment. Two other studies have implicated Aβ in the accumulation of tau in animal models. Microinjections of fibrillar Aβ in the cortex of aged rhesus monkeys caused the focal accumulations of intracellular phosphorylated tau (Geula et al., 1998). This was dependent upon both age and species; the same result was not observed for rats or young rhesus monkeys. Secondly, focal deposits of tau have been observed in mice that were transgenic for APP carrying AD associated mutations (Sturchler-Pierrat et al., 1997).

The brains of tau-deficient mice appear immunohistochemically normal and axonal elongation was not affected in cultured neurons (Harada et al., 1994). However, microtubule stability was decreased and its organization altered in some small-calibre axons. Furthermore, an increase in microtubule-associated protein 1A (MAP 1A), which might compensate for a functional loss of tau in large-calibre axons, was found. Thus, tau seems to be crucial in the stabilization and organization of axonal microtubules in certain axons. Subsequent studies have demonstrated that tau-deficient mice exhibit signs similar to certain symptoms characteristic of frontotemporal dementia patients, i.e. personality changes (disinhibition/aggression) and deterioration of memory and executive function. The mice showed muscle weakness and impaired balance control, hyperactivity in a novel environment, and impairment in contextual fear conditioning (Ikegami, Harada, & Hirokawa, 2000). Spatial learning tasks, however, were unaffected in the mice as is the memory function in FTDP-17 patients.

Although neurofibrillary tangles and phenotypic alterations were not reported in animals transgenic for 3- or 4-repeat tau isoforms (Brion, Tremp, & Octave, 1999; Gotz et al., 1995), these findings may reflect low levels of protein expression.

Impaired motor function, in the presence or absence of tauopathy, has been observed in mice expressing higher levels of human tau protein (Ishihara et al., 1999; Spittaels et al., 1999). In these animals the filamentous inclusions did not exhibit the ultrastructural features of AD PHFs.

A recent transgenic mouse model expressing human tau with the P301L mutation develops neurofibrillary tangles, neuronal loss and motor dysfunction (Lewis et at., 2000). The tau inclusions in these mice show both straight and twisted ribbon filaments similar to those found in human patients. Attempts to combine this model with amyloidosis are underway by crossing these mice with those transgenic for APP. Other transgenic mouse models are discussed in U.S. Pat. Nos. 5,912,410 and 5,898,094

Thus it can be seen that existing animal models fail to demonstrate any pathological evidence that the transgene leads to the accumulation of truncated tau protein encompassing the PHF domain. Although filaments are observed in tau carrying the P301L mutation, this corresponds to a form of tau that causes FTDP-17 and not AD. To date, no mutation in the tau gene has been identified which causes AD, and therefore approaches based purely on mutated protein for effect may be of limited relevance.

More particularly, there has been no clear disclosure of unmutated tau aggregating in these models, as evidenced by proteolytic processing to a truncated core fragment corresponding to that found in the actual AD PHF core. A system in which such proteolytic processing occurred in a pharmacokinetic context would thus provide a contribution to the art.

DISCLOSURE OF THE INVENTION

As discussed above, a conformational change of tau, rather than a chemical modification, is responsible for the progressive aggregation of tau molecules and their subsequent polymerization to form PHFs.

Surprisingly, the present inventors have now found that it is possible to reproduce this conformational change in a model system by causing the synthesis of a membrane-localised form of the protein of interest, e.g. tau, or fragments thereof containing the core aggregation domain.

It has been found, unexpectedly, that the association of e.g. tau or tau fragments with a cellular or organellar membrane, e.g. the plasma membrane of a cell or the membrane of the endoplasmic reticulum, can also seed the aggregation of further molecules of tau or tau fragments, thus propagating the formation of tau-tau aggregates in a manner somewhat analogous to that observed in the solid-phase assay system of WO 96/30766. This technique appears to have wide applicability to proteins involved in protein-aggregation type diseases.

Although not wishing to be limited by any particular mechanism, it is proposed by the inventors that the membrane-localised synthesis of the protein causes the high-affinity capture site of this protein to become exposed, by physically inducing the conformational change of tau that occurs upon its binding to a suitable substrate. The effect of this conformational change may be to create a sufficiently high local concentration of tau in its seeding conformation that further aggregation of the protein is promoted. These observations may have implications for all diseases in which protein aggregation plays a role.

In various aspects, the present invention provides, methods of modeling disease-like intracellular aggregation of an appropriate protein, or a core fragment thereof, the method being characterised by the step of synthesising a membrane-localised form of a protein which can initiate such aggregation. Such methods can be used, for instance, to identify modulators of the aggregation.

In general the membrane-targeted protein will either be one which actually undergoes the aggregation, although in some cases it will be one which triggers the aggregation of a second protein type.

Thus, in aspects of the invention there are provided fusion polypeptides comprising: (i) an aggregating portion, which is derived from a protein associated with a disease in which the protein aggregates or initiates aggregation of protein through an induced conformational polymerisation interaction, (ii) a heterologous membrane-localising portion.

In this way, a protein such as tau, or a core fragment of tau, or a corresponding protein as discussed below, can be synthesised in the form of a membrane-localized protein, where it can act as a seed for the intracellular aggregation and proteolytic processing of the fusion at an appropriate level for modeling aggregation of the actual protein from which it was derived. It may also seed aggregation with or between further molecules (e.g. full-length tau molecules), thus propagating the formation of protein aggregates.

Cells which express such membrane-associated protein aggregates can be used as models of disease-related protein aggregation, such as that observed in the cells of Alzheimer's-like diseases in vivo. This model system can be used in further studies, such as in screening assays for potential therapeutic, prognostic or diagnostic agents, as described in detail below.

Thus one aspect of the present invention there is disclosed a method of inducing, modeling or controlling aggregation of a protein associated with a disease in which the protein undergoes an induced conformational interaction, the method comprising the steps of:

(a) introducing to a membrane, a fusion polypeptide comprising: (i) an aggregation portion, which is derived from a first protein associated with a disease in which the protein undergoes an induced conformational polymerisation interaction, (ii) a heterologous membrane-localising portion, (b) causing or permitting an induced conformational polymerisation interaction between the fusion polypeptide and a further polypeptide, such as to cause aggregation of the said further polypeptide. Optionally the extent of aggregation may be monitored.

In this and other embodiments, the further polypeptide may, for example, be a further fusion protein, or may result from proteolytic degradation of the fusion polypeptide such as to yield a second protein capable of undergoing an induced conformational polymerisation interaction with said first protein, or may be a quite different polypeptide.

Thus in a further preferred aspect of the present invention there is disclosed a method of inducing, modeling or controlling aggregation of a (second) protein associated with a disease in which the protein undergoes an induced conformational interaction, the method comprising the steps of:

(a) introducing to a membrane, a fusion polypeptide comprising: (i) an aggregation portion, which is derived from a first protein associated with a disease in which the protein undergoes or initiates an induced conformational polymerisation interaction, (ii) a heterologous membrane-localising portion, (b) contacting the fusion polypeptide with a second protein capable of undergoing an induced conformational polymerisation interaction with said first protein, whereby interaction of the second protein with the membrane localized fusion protein causes aggregation of the second protein. Optionally the extent of aggregation may be monitored.

Examples are disclosed below of preferred first and second proteins, which may be derived from the same or different protein associated with a disease. In particular, the first protein will be one which (as a result of an induced conformational change) initiates and\or participates in the aggregation of further protein which is the same or different, and the second will be one which actually aggregates in the relevant disease.

In preferred embodiments there are disclosed cell-based method of inducing intracellular aggregation of a protein associated with a disease in which the protein undergoes an induced conformational interaction e.g. comprising the steps of: (a) introducing into a cell, such that it becomes localised at a membrane in the cell, a fusion polypeptide comprising: (i) an aggregation portion, which is derived from a first protein associated with a disease in which the protein undergoes or initiates an induced conformational polymerisation interaction, (ii) a heterologous membrane-localising portion, (b)

introducing into the cell, a second protein capable of undergoing an induced conformational polymerisation interaction with said first protein, whereby interaction with of the second protein with the localized fusion protein causes intracellular aggregation and optionally proteolytic processing of either.

Again, optionally the extent of aggregation and\or proteolytic processing of the second protein may be monitored. This may be in the presence of one or more agents suspected of being capable of modulating (e.g. inhibiting or reversing) the aggregation.

Generally, speaking the method will be carried out by use of a nucleic acid encoding the fusion protein and\or the second protein.

Some preferred aspects and embodiments of the present invention will now be described in more detail.

Diseases and Proteins

As stated above, the invention may employ any protein which is associated with a disease in which the protein undergoes an induced conformational polymerisation interaction i.e one in which a conformational change of the protein seeds the binding and aggregation of further protein molecules in a self-propagating manner. Once nucleation is initiated, an aggregation cascade may ensue which involves the induced conformational polymerisation of further protein molecules, which conformational change may render the aggregates more resistant to further proteolysis. The protein aggregates thus formed are thought to be a proximal cause of neurodegeneration, clinical dementia, and other pathological symptoms of this group of diseases. Purely for brevity, this group of conditions may be referred to herein as "Alzheimer's disease-like" conditions.

Preferred embodiments of the invention are based on tau protein. Where used herein, the term "tau protein" refers generally to any protein of the tau protein family. Tau proteins are characterised as being one among a larger number of protein families which co-purify with microtubules during repeated cycles of assembly and disassembly (Shelanski et al. (1973) Proc. Natl. Acad. Sci. USA, 70., 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail. The term is thus exemplified by, but not limited to, tau molecules which form PHFs (and, ultimately, neurofibrillary tangles) in Alzheimer's disease brains. Indeed, PHFs accumulate in the somatodendritic compartment, where the predominant microtubule-associated protein is MAP2 (Matus, A., in "Microtubules" [Hyams and Lloyd, eds.] pp 155-166, John Wiley and Sons, NY). MAP2 isoforms are almost identical to tau protein in the tandem repeat region, but differ substantially both in the sequence and extent of the N-terminal domain (FIGS. 7 and 8; Kindler and Garner (1994) Mol. Brain Res. 26, 218-224). Nevertheless, aggregation in the tandem-repeat region is not selective for the specific tau core amino acid sequence. Thus it will be appreciated that any discussion herein in relation to tau-tau aggregation should be taken as relating also to tau-MAP2 aggregation and MAP2-MAP2 aggregation.

FIG. 20 shows a Table listing various other disease-associated aggregating proteins which may be used in the present invention. In each case the disease or diseases in which the initiation of aggregation and\or mutation of the protein(s) may play a role is also listed. The domain or mutation responsible for the disease activity is listed, and at least all or part of this minimal portion of the protein would preferably be encompassed by the protein used in the invention as the membrane-targeted 'capture' or 'seeding' protein.

As can be seen from the table, example diseases which are characterised by pathological protein aggregation include motor neurone disease and Lewy body disease. Furthermore, the pathogenesis of neurodegenerative disorders such as Pick's disease and Progressive Supranuclear Palsy appears to correlate with an accumulation of pathological truncated tau aggregates in the dentate gyrus and stellate pyramidal cells of the neocortex, respectively (Wischik et al. 2000, loc. cit).

In certain preferred embodiments, the invention employs proteins which may be involved in the initiation stages of diseases of the type discussed herein. For example, in Wischik, C. M., et al. (1997) [supra] a variety of membrane proteins which may be involved in the initiation of tau capture and amyloid protein precursor in AD are discussed. These include presenilins and mitochondrial proteins such as core protein 2 of the $bc_1$ enzyme complex (CP2), ATP-synthase subunit 9 (ATP S-9) and porin. Thus preferred embodiments of the invention may utilize membrane-targeted proteins including those regions of these molecules shown in the Table in FIG. 21.

Thus it will be appreciated, in the light of the above discussion, (and except where context requires otherwise) where the embodiments of the invention are described with respect to tau protein or tau-like proteins (e.g. MAP2) the description should be taken as applying equally to the other proteins discussed above (e.g. β-amyloid, synuclein, prion, appropriate mitochondrial protein etc.) or other proteins which may initiate or undergo a similar pathological aggregation by virtue of conformational change in a domain critical for propagation of the aggregation, or which imparts proteolytic stability to the aggregate this formed (article by Wischik et al. (in "Neurobiology of Alzheimer's Disease", 2nd Edition (2000) Eds. Dawbarn, D. and Allen, S. J., The Molecular and Cellular Neurobiology Series, Bios Scientific Publishers, Oxford). All such proteins may be referred to herein as "aggregating disease proteins."

Likewise, where mention is made herein of "tau-tau aggregation", or the like, this may also be taken to be applicable to other "aggregating-protein aggregation", such as β-amyloid aggregation, prion aggregation and synuclein aggregation etc. Likewise "tau proteolytic degradation" and so on.

Proteins for use in the methods described above may, where appropriate (e.g. in the study of tau-tau binding) be isolated from brain tissues by methods known to those skilled in the art, for instance as described in the respective references. Soluble tau can be isolated either from human brain tissues, or from animal brain tissues, with a postmortem delay of less than 24 hours (see Wischik et al. (1988); (1995a), loc. cit.). Microtubule proteins can be obtained by three cycles of temperature-dependent assembly-disassembly according to Shelanski et al. (1973, loc. cit.). Lipofection of the proteins may be carried out analogously to the methods described in WO96/30766. More preferably the production of e.g. tau proteins and fragments thereof will be achieved by conventional recombinant DNA technology as described below.

Fragments, Derivatives and Controls

There is no requirement that the invention employ full-length protein; indeed this may be undesirable in certain contexts. Equally, the protein used may include an extended N- or C-terminus.

As shown in the Examples hereinafter, the nature of the aggregating portion of the fusion may be such that appropriate levels of aggregation (and possible proteolytic processing) are achieved even in the absence of further molecules.

Alternatively or additionally, further molecules (e.g. full length disease protein molecules) may be provided which participate in the aggregation.

In preferred embodiments of the present invention, the fusion polypeptide, as synthesized in either the cell-based method or the in vitro method described herein, comprises or consists essentially of a truncated fragment. Such a fragment will generally be a "core fragment" which term refers to that part of the protein that is able to bind to further protein (which may be same or different) to initiate or propagate aggregation. In the case of disease proteins which aggregate, such core fragments are also likely to be those which contribute to the proteolytic stability of the aggregate.

Thus, for example, a "tau core fragment" is a tau fragment comprising a truncated tau protein sequence derived from the tandem repeat region ("core tandem repeat domain") and, which, in the appropriate conditions, is capable of binding to the tandem repeat region of a further tau protein or a MAP2 protein with high affinity.

Where the fusion polypeptide is derived from tau, the truncated fragment may preferably comprise a fragment from about 186-296 extending to about 390-441 of the full-length protein, more preferably any of the following portions: 186 to 390 or 391 or 441; 296 to 390 or 391 or 441 (see FIGS. 5 and 10). In the Examples hereinafter, the ligation of the tau fragment to the signal sequence destroyed amino acids 186-189, so that the starting amino acid was equivalent to 190.

In the case of APP (amyloid precursor protein), for instance, expression of a fragment of the APP that encompasses the Aβ domain of 1-40 or 1-42 amino acids as a fusion protein, may be preferred.

Other core fragments may be based e.g. on the domains discussed with reference to FIGS. 20 and 21.

The total length of the fusion polypeptide may be any which is appropriate to the assay and aggregation disease protein core fragment being used, but will generally be greater than 30, 40, 50, 60, 70, 80, 90, 100, 200, or 500 amino acids in length.

In all instances herein where a named protein (e.g. core fragment) or a recited nucleic acid sequence is discussed, a derivative or other variant of the corresponding reference protein (or nucleic acid) may be used as appropriate, provided that it retains appropriate characteristics of the reference sequence. Such derivatives will also share sequence identity with the reference sequence.

In principle, a derivative may be a chemical derivative which may be prepared from the functional groups occurring as side chains on the residues or the NB or C-terminal groups, by means known in the art. These derivatives may include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl- or threonyl residues) formed with acyl moieties.

More commonly the derivative will be one by way of amino acid insertion, deletion, or addition of the reference sequence. For example, a tau protein, or tau core fragment, derivative will comprise at least a partial amino acid sequence resembling the tandem repeat region of the tau proteins, but in which one or more of the amino acids of the natural tau or its fragments have been replaced or deleted, or into which other amino acids have been inserted.

Such changes may be made to enhance or ablate binding activity (the latter case being useful for control experiments). Controls may contain deletions of sequences or domains to see what effect on aggregation these may have.

Preferred derivatives may be those which incorporate mutations corresponding to those known or suspected to be associated with the disease state. These may include changes corresponding to P301S within the tau sequence (see FIG. 5). Other mutations include G272V, G389R, P301L, N279K, S305N, V337M, G272V, K280Δ, R406W (see also Wischik et al, 2000, supra).

Other preferred derivatives may include tandem repeats of the core-fragments discussed above, or binding domains within those fragments.

Yet further derivatives may be based on chimeric products based on multiple, related, disease proteins in which their sequences are mixed or combined. For example restriction enzyme fragments of tau could be ligated together with fragments of MAP2 or even of an unrelated gene to generate recombinant derivatives. An alternative strategy for modifying the core fragments would employ PCR as described by Ho et al., 1989, Gene 77, 51-59 or DNA shuffling (Crameri et al., 1998 Nature 391).

Membrane Localizing Sequence

The heterologous membrane-localising or targeting portion of the fusion may be any appropriate signal sequence from any suitable protein e.g. a signal sequence deriving from rat albumin. Alternatively it may be a modified sequence derived from a native localizing portion. However, in each case it will be a sequence which does not occur 'naturally' with the aggregation portion. The presence of a signal sequence on a protein will direct the nascent polypeptide\ribosome complex to the ER membrane where it may be inserted into it. Translocation across the membrane of the ER, and into the ER lumen, may then occur depending on the hydrophobicity of the protein.

The signal sequence may, depending on the chosen host cell for expression of a membrane-localized form of the protein, be a prokaryotic signal sequence e.g. an alkaline phosphatase, penicillinase, lpp, or heat-stable enterotoxin II leader. For yeast expression the signal sequence may be, e.g., the yeast invertase leader, alpha factor leader (including Saccharomyces and Kluyveromyces α-factor leaders, the latter being described in U.S. Pat. No. 5,010,182), or acid phosphatase leader, the C. albicans glucoamylase leader (EP 362, 179), or the signal described in WO 90/13646. In mammalian cell expression, a mammalian signal sequence such as that from rat albumin may be used, or alternatively a viral leader sequence may be employed.

This membrane localising portion may also include a membrane anchor sequence and/or a stop-transfer sequence. Generally this may be preferred for proteins, the intrinsic (hydrophobic) properties of which, may otherwise lead them to be secreted or located extra-cellularly, when fused with a signal peptide. A membrane anchor domain can be incorporated to prevent the entire protein from being translocated into the lumen of the ER and ultimately secreted. In general the protein must be oriented on the cytosolic surface of any protein with which it is associated such that it can interact with exogenous protein in the cytoplasm.

Other Binding Partners

In one aspect of the invention, the membrane-localized expression of a protein such as tau or a core fragment of tau can be used to screen for specific binding partners of that protein or fragment, e.g. proteins other than tau or the core fragment of tau which can bind to the membrane-localised form of tau or a fragment thereof.

Thus, the present invention also relates to methods of screening for specific binding partners of the protein (e.g. tau) of interest, comprising causing or allowing the membrane-localized expression of the protein, contacting that protein with one or more potential binding partners, and determining whether or not the potential binding partner has bound to the membrane-localized protein.

The detection of binding between the protein of interest and a potential binding partner may be carried out using any suitable method, as described in detail above.

The method may include the further step of recovering the specific binding partner thus identified.

In this way, the present invention enables the identification of specific binding partners of proteins such as tau, which may represent further pathological binding partners of such proteins in Alzheimer's disease-like aggregates.

Use of Nucleic Acid Constructs

In one preferred embodiment the (bound) fusion polypeptide (of step (a)) above is introduced into the cell by expression therein under the transcriptional control of a constitutive promoter, while the second ('free') protein (of step (b)) is introduced by expression therein under the transcriptional control of an inducible promoter, in the presence of the appropriate inducing agent. Alternatively, in the reverse, the (a) and (b) proteins may be expressed inducibly and constitutively respectively.

This system can be used to control the level or timing of aggregation in the cell.

Particularly preferred is the following configuration for a cell-based tau-tau binding assay: A tau fragment corresponding to the truncated tau unit of the core PHF is constitutively expressed in a membrane-localised form in a host cell, so as to expose the high affinity tau-tau binding site within the tandem repeat region, and at a level which does not kill the cells—i.e. in a stable cell line. The tau fragment is preferably longer than the core repeat domain fragment (suitably amino acid residues 186-390 or 186-441 of full-length tau), which is able to achieve a balance between aggregation and toxicity.

Nucleic acids of, or for use in, the present invention may be provided isolated and/or purified from their natural environment, in substantially pure or homogeneous form, or free or substantially free of other nucleic acids of the species of origin. Where used herein, the term "isolated" encompasses all of these possibilities.

A nucleic acid acid encoding the fusion polypeptide will be at least partially synthetic in that it will comprise nucleic acid sequences which are not found together in nature (do not run contiguously) but which have been ligated or otherwise combined artificially.

Nucleic acid according to the present invention may be in the form of, or derived from, cDNA, RNA, genomic DNA and modified nucleic acids or nucleic acid analogs. Where a DNA sequence is specified, e.g. with reference to a figure, unless context requires otherwise the RNA equivalent, with U substituted for T where it occurs, is encompassed.

In particular, nucleic acids may comprise, consist or consist essentially of any of the sequences disclosed herein (which may be a gene, a genomic clone or other sequence, a cDNA, or an ORF or exon of any of these etc.) Where a nucleic acid (or nucleotide sequence) of the invention is referred to herein, the complement of that nucleic acid (or nucleotide sequence) will also be embraced by the invention. The 'complement' in each case is the same length as the reference, but is 100% complementary thereto whereby by each nucleotide is base paired to its counterpart i.e. G to C, and A to T or U.

Thus the invention also relates, in a further aspect, to a nucleic acid molecule which comprises a nucleotide sequence encoding a fusion protein discussed above e.g. a aggregating disease protein or its core tandem repeat domain (i.e. a protein or fragment thereof that is implicated in a neurodegenerative disorder such as Alzheimer's disease) linked to a signal sequence and, if necessary, a sequence encoding a membrane anchor domain or a stop-transfer sequence, whereby the encoded polypeptide will become inserted into the ER membrane.

The nucleic acid molecule encoding the protein of interest linked to the signal sequence may optionally also include an exogenous 3'UTR sequence, e.g. a sequence derived from rat globin. The nature of the 3'UTR appears to influence the efficiency of targeting of a protein to the ER in cells, and the 3'UTR sequence can thus be selected accordingly (Partridge, K. A., et al. (1999) *Cytotechnology* 30, 37-47).

As described above, the nucleic acids may encode derivatives or other variants sharing homology with the reference sequences in question. Preferably, the nucleic acid and/or amino acid sequence in question would share about 50%, or 60%, or 70%, or 80% identity, most preferably at least about 90%, 95%, 96%, 97%, 98% or 99% of the sequence upon which the variant is based. Similarity or homology may be as defined and determined by the TBLASTN program, of Altschul et al. (1990) *J. Mol. Biol.* 215: 403-10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711) using the default parameters. One common formula for calculating the stringency conditions required to achieve hybridization between nucleic acid molecules of a specified sequence homology is: $T_m$=81.5° C.+16.6Log [Na+]+0.41 (% G+C)−0.63 (% formamide)−600/#bp in duplex.

Nucleic acid sequences which encode a polypeptide or peptide linked to a signal sequence in accordance with the present invention can be readily prepared by the skilled person using the information and references contained herein and techniques known in the art (for example, see Sambrook, Fritsch and Maniatis, "Molecular Cloning, A Laboratory Manual", Cold Spring Harbor Laboratory Press, 1989, and Ausubel et al., Short Protocols in Molecular Biology, John Wiley and Sons, 1992). These techniques include (i) the use of the polymerase chain reaction (PCR) to amplify samples of the relevant nucleic acid, e.g. from genomic sources, (ii) chemical synthesis, or (iii) preparation of cDNA sequences. The nucleic acid thus prepared can then be linked to a sequence encoding a suitable signal peptide, or can be inserted into a vector construct which includes such a signal peptide-encoding sequence. Other methods suitable for adaptation to the synthesis of the membrane-localized protein in recombinant vertebrate cell culture are described in Gething et al., Nature, 293:620-695 (1981); Mantei et al., Nature, 281:40-46 (1979); EP 117,060; and EP 117,058.

DNA encoding e.g. tau core fragments may be generated and used in any suitable way known to those of skilled in the art, including by taking encoding DNA, identifying suitable restriction enzyme recognition sites either side of the portion to be expressed, and cutting out said portion from the DNA. Modifications to the protein (e.g. tau)-encoding sequences can be made, e.g. using site directed mutagenesis.

Constructs

In the cell-based assay embodiments of the present invention, the construction of a membrane-localized form of the protein of interest, e.g. tau or a fragment of tau, can be achieved by causing or allowing the expression in a cell of an expression construct or vector, which comprises nucleic acid encoding the given protein linked to a signal sequence and, where required, an anchor or stop-transfer sequence, and which optionally also includes an exogenous 3'UTR sequence.

In general, nucleic acid encoding the signal sequence to which the nascent protein molecule is linked may be a component of the vector itself, or it may be a part of the exogenous protein-encoding DNA that is inserted into the vector.

The construct may include any other regulatory sequences or structural elements as would commonly be included in such a system, and as is described below. As well as the signal sequence, the vector components will usually include, but are not limited to, one or more of an origin of replication, one or more marker genes, an enhancer element, a promoter, and a transcription termination sequence. Construction of suitable vectors containing one or more of these components employs standard ligation techniques which are known to the skilled artisan.

Nucleic acid sequences which enable a vector to replicate in one or more selected host cells are well known for a variety of bacteria, yeast, and viruses. For Example, various viral origins (SV40, polyoma, adenovirus, VSV or BPV) are useful for cloning vectors in mammalian cells.

Particularly preferred is an expression vector comprising a nucleic acid as described herein. The vector may, for example, be in the form of a plasmid, cosmid, viral particle, phage, or any other suitable vector or construct which can be taken up by a cell and used to express a membrane-localised form of the aggregating disease protein, e.g. tau or tau core fragment.

Expression vectors usually contain a promoter which is operably linked to the protein-encoding nucleic acid sequence of interest, so as to direct mRNA synthesis. Promoters recognized by a variety of potential host cells are well known. "Operably linked" means joined as part of the same nucleic acid molecule, suitably positioned and oriented for transcription to be initiated from the promoter. DNA operably linked to a promoter is "under transcriptional control" of the promoter. Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g. the actin promoter or an immunoglobulin promoter, and from heat-shock promoters, provided such promoters are compatible with the host cell systems.

Expression vectors used in eukaryotic host cells (yeast, fungi, insect, plant, animal, human, or nucleated cells from other multicellular organisms) will also contain sequences necessary for the termination of transcription and for stabilizing the mRNA.

The promoter may be "inducible"—which is to say, as is well understood by those skilled in the art, expression is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. In experiments below, a Lac inducible promoter has been used.

Expression vectors of the invention may also contain one or more selection genes. Typical selection genes encode proteins that (a) confer resistance to antibiotics or other toxins e.g. ampicillin, neomycin, methotrexate, or tetracycline, (b) complement auxotrophic deficiencies, or (c) supply critical nutrients not available from complex media, e.g., the gene encoding D-alanine racemase for *Bacilli*. An example of suitable selectable markers for mammalian cells are those that enable the identification of cells competent to take up the given membrane-targeted protein-encoding nucleic acid, such as DHFR or thymidine kinase. An appropriate host cell, when wild-type DHFR is employed, is the CHO cell line deficient in DHFR activity, prepared and propagated as described by Urlaub et al., *Proc. Natl. Acad Sci USA* 77:4216 (1980). A suitable selection gene for use in yeast is the trpl gene present in the yeast plasmid Rp7 [Stinchcomb et al., Nature, 282:39 (1979); Kingsman et al., Gene, 7:141 (1979); Tschemper et al., Gene, 10:157 (1980)]. The trpl gene provides a selection marker for a mutant strain of yeast which lacks the ability to grow in tryptophan, for example, ATCC: No. 44076 or PEP4-1 [Jones, Genetics, 85:12 (1977)].

Transformation

The method referred to above may therefore further include introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus.

The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23:315 (1983) and WO 89/05859 published 29 Jun. 1989.

For mammalian cells without such cell walls, the calcium phosphate precipitation method of Graham and van der Eb, Virology 52:456-457 (1978) can be employed. General aspects of mammalian cell host system transformations have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g, polybrene, polyornithine, may also be used. For various techniques for transforming mammalian cells, see Keown et al., Methods in Enzymology, 185:527 537 (1990) and Mansour et al., Nature 336:348-352 (1988).

Host Cells

Suitable host cells for use in the invention may include bacteria, eukaryotic cells such as mammalian and yeast cells, and baculovirus systems.

Mammalian cell lines available in the art for expression of a heterologous polypeptide include fibroblast 3T6 cells, HeLa cells, baby hamster kidney cells, COS cells, monkey kidney CV1 line transformed by SV40 (COS-7, ATCC CRL 1651), Chinese hamster ovary cells/-DHFR(CHO, Urlaub and Chasin, *Proc. Natl. Acad. Sci. USA* 77:4216 (1980)); mouse sertoli cells (TM4, Mather, Biol. Reprod. 23:243-251 (1980)); human lung cells (W138, ATCC CCL 75); human liver cells (Hep G2, HB 8065); mouse mammary tumour cells (MMT 060562, ATCC CCL51); and many others. Preferred may be any of the range of well known neuroblastomal cell lines e.g. N2A, N1E, SY5Y.

Suitable prokaryotic hosts include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Eukaryotic microbes such as filamentous fungi or yeast are also suitable cloning or expression hosts for vectors. *Saccharomyces cerevisiae* is a commonly used lower eukaryotic host microorganism. The selection of the appropriate host cell is deemed to be within the skill in the art.

In a further aspect, the present invention provides a host cell containing heterologous nucleic acid of the invention as described above. The nucleic acid of the invention may be integrated into the genome (e.g. chromosome) of the host cell. Integration may be promoted by inclusion of sequences which promote recombination with the genome, in accordance with standard techniques. Alternatively, the nucleic acid may be on an extrachromosomal vector within the cell, or otherwise identifiably heterologous or foreign to the cell. Generally the cell line will be capable of expressing a membrane-localised form of a protein such as tau or derivative thereof, the cell line being transformed with nucleic acid encoding the protein or derivative thereof. Preferred cell-lines may be based on the fibroblast cell line, e.g. 3T6.

Expression Products

Host cells transfected or transformed with expression or cloning vectors described herein for the production of the membrane-localized protein may be cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in "Mammalian Cell Biotechnology: a Practical Approach", M. Butler, ed. JRL Press, (1991) and Sambrook et al, supra.

Gene expression can be confirmed in a sample directly, for example, by conventional Southern blotting, Northern blotting to quantitate the transcription of mRNA [Thomas, Proc. Natl Acad Sci. USA, 77:5201-5205 (1980)], dot blotting (DNA analysis), or in situ hybridization, using an appropriately labeled probe, based on the sequence of the aggregating disease protein. Alternatively, antibodies may be employed that can recognize specific duplexes, including DNA duplexes, RNA duplexes, and DNA-RNA hybrid duplexes or DNA-protein duplexes.

Gene expression, alternatively, may be measured by immunological methods such as immunohistochemical staining of cells or tissue sections, and assay of cell culture, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of the aggregating disease polypeptide.

Thus one aspect of the present invention entails causing or allowing expression from the nucleic acids discussed herein, e.g. by culturing host cells (which may include cells actually transformed, although more likely the cells will be descendants of the transformed cells) under conditions for expression of the gene, so that the encoded polypeptide (or peptide) is produced.

The present invention also encompasses a method of making a membrane-localized polypeptide or peptide of the preceding aspect, the method including expression from nucleic acid as described above. As an alternative to growing in a culture a host cell which contains such a vector, under appropriate conditions which cause or allow expression of the polypeptide, the polypeptides and peptides may be expressed in an in vitro system, such as a reticulocyte lysate system, as described herein.

Generally, following production by expression, the encoded fusion polypeptide will be utilised in the environment of the cells in which it is expressed, i.e. without isolating it from the membranes in which it is localised. In this way, as discussed above, it has surprisingly been found by the present inventors, the membrane-localized form of the protein can be used to seed the aggregation of further protein molecules in a manner which mimics Alzheimer's disease-like protein aggregation. Thus, cells displaying membrane-localised Alzheimer's disease-like protein aggregates in their membranes (e.g. ER membranes) can be used in further screening assays (for a discussion of which, see below).

Nevertheless, polypeptides of the invention may be isolated and/or purified from the host cell and/or culture medium, either in the form of a membrane fraction, or isolated from the membranes themselves, as the case may be. Proteins may be purified to essential homogeneity by known methods such as, for example, by centrifugation at different velocities, by precipitation with ammonium sulphate, by dialysis (at normal pressure or at reduced pressure), by preparative isoelectric focusing, by preparative gel electrophoresis or by various chromatographic methods such as gel filtration, high performance liquid chromatography (HPLC), ion exchange chromatography, reverse phase chromatography and affinity chromatography (e.g. on Sepharose™ Blue CL-6B or on carrier-bound monoclonal antibodies).

Thus the invention relates, in a further aspect, to a polypeptide encoded by a nucleic acid as provided in a preceding aspect e.g. a polypeptide or fragment thereof, (for instance based on tau or a core fragment of tau) linked to a signal peptide and (if necessary) an anchor and/or stop-transfer sequence. In a preferred embodiment, the polypeptide comprises aggregating disease protein e.g. tau protein, or a derivative thereof. More preferably, the protein comprises a tau core fragment, as described above.

In Vitro Model

The membrane-localised form of the protein of interest described above may be used in in vitro models.

For example it could be used analogously to the tau fragment used in the assay of WO 96/30766 which is incorporated herein by cross reference. As described above, in this assay for tau aggregation and inhibitors thereof a fragment of tau corresponding to the core repeat domain is adsorbed to a solid phase substrate. This is able to capture soluble full-length tau and bind tau with high affinity.

The combination of these two strategies (membrane localisation, in vitro solid phase) may be advantageous in certain contexts.

As a further alternative to the cell-based methods described above, the modeling method can be performed in vitro, by causing the expression in an in vitro protein-expression system of a membrane-localised form of the protein of interest.

For instance, an in vitro medium containing microsomes (which can be easily produced by fragmentation of the endoplasmic reticulum), ribosomes, tRNA molecules, and mRNA encoding the protein or protein fragment of interest linked to a signal sequence, as well as any other soluble factors required for protein synthesis and translocation, could be used to synthesise a membrane-bound form of the protein. Here, in a similar way to the cell-based system described above, ribosomes would become attached to the microsomal membrane (which is equivalent to the ER membrane of the cell-based system) and cause the synthesis of the encoded polypeptide molecule.

In this latter embodiment, however, the construct which encodes the aggregating disease protein, the signal sequence and the anchor and/or stop transfer sequences (if required), are all preferably designed in such a way that the majority of the encoded protein molecule, when inserted into the microsomal membrane, projects from the cytosolic surface of the membrane rather than into the lumen. In this way, the protein molecule will be accessible both to further protein molecules (so allowing Alzheimer's disease-like aggregation to occur at the cytosolic surface of the microsome), and to test agents in a screening assay to screen for potential inhibitors or modulators of such aggregation.

The skilled person will be familiar with the design of suitable constructs in order to achieve desired protein topologies. Further discussion of this point will be given below.

Thus, the common feature linking the cell-based and in vitro model systems provided herein is the synthesis of a membrane-localised form of the aggregating disease protein or protein fragment. This common feature gives rise to a method of generating a seed molecule, which can propagate the aggregation of further protein molecules in a manner which mimics the pathological aggregation of proteins such as tau during the formation of e.g. neurofibrillary tangles.

Detection of Induced Polymerization Interaction

In various embodiments, the progress aggregation (or modulation of aggregation) may be detected directly or indirectly by monitoring the concentration or level any one or more of the following species: an aggregate of the fusion and\or second protein (e.g. based on sedimentation co-efficients), or a proteolytic fragment of either of these (which will generally increase with aggregation); a species corresponding to the non-aggregated fusion polypeptide and\or second protein (which may decrease).

Figure 1D:
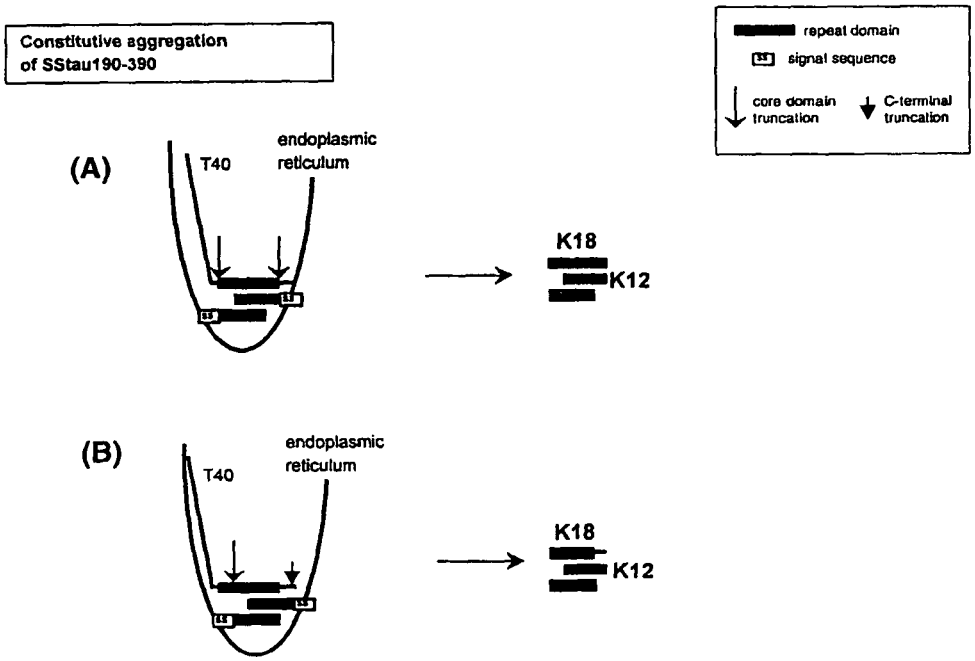

Thus, as exemplified with particular tau fusions and proteins (based on 40 kDa 190-441 fragment and T40), aggregation can be monitored on the basis of increasing levels of a 25 kDa processed species, derived from both the fusion and longer proteins (see FIG. 1).

It may be desirable that the second ('free') protein used in method is labeled, or otherwise distinguishable from the membrane-bound protein, e.g. immunologically distinct, to assist in detecting the degree of aggregation of the protein molecules.

For instance, the free form of the aggregating disease protein may be linked to a reporter molecule. The term "reporter molecule", as used in the present specification, is intended to mean a molecule which, by its chemical nature, provides an analytically-detectable signal that allows the detection of antigen-bound antibody. Detection should preferably be quantifiable, to allow determination of the amount of antigen in the sample; this may be calculated in absolute terms, or may be performed in comparison with a standard (or series of standards) containing a known normal level of antigen. Examples are well known to those skilled in the art e.g. enzymes or fluorophores.

Thus the free form of the protein may be directly modified (e.g. marked with a radioactive or enzymatically-detectable label) or conjugated (e.g. to a fluorophore) in a domain of the molecule, for example the N-terminal segment, which is known not to be involved in the high affinity tau-tau binding site, so that it thereby functions both as the ligand in the tau-tau binding assay, and as the reporter molecule.

Where antibodies or fragments thereof are used in embodiments of the method of the present invention may be produced by conventional techniques. Polyclonal antibodies may raised e.g. by injecting the corresponding tau antigen into an animal, preferably a rabbit, and recovering the antiserum by immunoaffinity purification, in which the polyclonal antibody is passed over a column to which the antigen is bound and is then eluted in a conventional manner. Preferably the invention will use monoclonal antibodies which are selective to tau epitopes may be prepared by the method of Kohler and Milstein. Suitable monoclonal antibodies to tau epitopes can be modified by known methods to provide Fab fragments or (Fab')2 fragments, chimeric, humanised or single chain antibody embodiments. Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Generally speaking, where antibodies are employed for detection, the antibody may carry a reporter molecule. Alternatively, detection of binding may be performed by use of a second antibody capable of binding to a first unlabelled, tau-specific antibody. In this case, the second antibody is linked to a reporter molecule.

Antibodies may be used in any immunoassay system known in the art, including, but not limited to: radioimmunoassays, "sandwich" assays, enzyme-linked immunosorbent assays (ELISA); fluorescent immunoassays, protein A immunoassays, etc. Typically, an immunoblot method is used. Preferably the immunoassay is performed in the solid phase, as would be well known to the skilled person. For instance, an antibody may be adsorbed to e.g. an assay column, and the cellular sample may then be washed through the column under conditions suitable for enabling binding to the solid-phase antibody of any aggregate of the protein of interest, e.g a tau-tau aggregate, which is present in the membrane of the cell. Excess reagent is washed away, and the binding of aggregated protein to the column can then be detected by any suitable means, e.g. as exemplified above and below.

Preferred monoclonal antibodies are as follows:

Those which recognise the N-terminal or C-terminal of the tau epitope permit measuring of binding between truncated and full-length tau species. Especially useful are antibodies recognising human-specific epitopes. One such monoclonal antibody (designated 27/499) recognises a human-specific epitope located in the region between Gly-16 and Gln-26 of tau, and thereby permits measurement of binding between full-length tau species, provided one is derived from a non-human source (Lai (1995); "The role of abnormal phosphorylation of tau protein in the development of neurofibrillary pathology in Alzheimer's disease", PhD Thesis, University of Cambridge).

Those which recognise the core tau fragment truncated at Glu-391. An example is mAb 423 (Novak et al. (1993), loc. cit.). This antibody enables detection of the binding of a truncated core tau fragment terminating at Glu-391 to a similar fragment terminating at Ala-390, which is not recognised by mAb 423. This truncation occurs naturally in the course of PHF assembly in Alzheimer's disease (Mena et al. (1995), (1996), loc. cit.; Novak et al. (1993), loc. cit.; Mena et al. (1991), loc. cit.). Additionally, when tau is bound via the repeat domain in vitro, digestion with a protease (e.g. pronase) generates a fragment detectable by mAb 423 (see Wischik et al, 1996, loc cit). FIG. 17 shows various tau-derived species which may generated in an assay according to the present invention, and the approximate truncation point in each. mAb 423 may thus be used to demonstrate that the molecular conformation of the tau-tau binding interaction generated in a membrane-localised model system as provided herein corresponds to that which occurs pathologically in the brain, and hence that such model systems according to the present invention represent viable models of Alzheimer's disease-like protein aggregation.

Those which recognise a generic tau epitope in the repeat domain. A preferred embodiment utilises an antibody (e.g. MAb 7.51). Where tau-MAP2 or MAP2-MAP2 aggregation is to be detected, an antibody which detects a generic MAP2 epitope could be used. Antibody 7.51 recognises a generic tau epitope located in the antepenultimate repeat of tau (Novak et al. (1991) Proc. Natl. Acad. Sci. USA, 88, 5837-5841), which is occluded when tau is bound in a PHF-like immunochemical configuration but can be exposed after formic acid treatment (Harrington et al. (1990), (1991), loc. cit.; Wischik et al. (1995a), loc. cit.). Normal soluble tau, or tau bound to microtubules, can be detected using mAb 7.51 without formic acid treatment (Harrington et al. (1991), loc. cit.; Wischik et al. (1995a), loc. cit.). Binding of full-length tau in the tau-tau binding assay is associated with partial occlusion of the mAb 7.51 epitope.

Antibody 27/342 recognises a non-species specific generic tau epitope located between Ser-208 and Ser238 which is partially occluded in the course of the tau-tau interaction (Lai, loc. cit.).

The binding sites of some monoclonal antibodies are shown in FIG. 4.

Screening for Modulators and Inhibitors

As described above, the invention is preferably concerned with use of a nucleic acid molecule, polypeptide or derivative thereof, a host cell, or an in vitro protein expression system, as provided herein, in a method of modeling Alzheimer's disease-like protein aggregation. Methods of the invention may include the steps of causing the expression of the nucleic acid molecule in a cell-based or microsome-based expression system, so that the encoded polypeptide becomes localized in a membrane (e.g. the ER membrane) of the cell, or in the microsomal membrane, respectively.

In a preferred aspect, there is disclosed a method of identifying a therapeutic agent for treatment of a disease as discussed herein, which method comprises the step of providing the fusion polypeptide (and preferably, the second protein discussed above) and contacting the membrane-localized protein with test substances which are suspected of being inhibitors or modulators of the disease associated protein aggregation. In particular, the fusion polypeptides as produced by the modeling methods described above can be used to investigate and screen for potential inhibitors or modulators of Alzheimer's disease-like protein aggregation, such as pathological tau-tau association.

Thus the various methods described above may comprise the further steps of (c) contacting the fusion polypeptide and\or the second protein with one or more agents which it is desired to assess for ability to modulate or inhibit the aggregation; (d) monitoring the extent of aggregation, and optionally correlating the extent of aggregation with the modulatory activity of the agent(s).

Thus a method of identifying a modulator of (preferably intracellular) aggregation of a protein associated with a disease in which the protein undergoes an induced conformational interaction, may comprise performing a method for inducing aggregation as described above in the presence of one or more agents suspected of being capable of modulating (e.g. inhibiting or reversing) the aggregation. The degree of aggregation (and optionally proteolytic processing) may be observed in the presence or absence of the agent, and the relative values correlated with its activity as a modulator.

Preferably, where the screening method employs cells which express a membrane-localised form of the protein of interest, such as tau, these may comprise, e.g., cells from a neuronal cell line, e.g. a neuroblastoma cell line, or cells from a fibroblast cell line. In a preferred embodiment, the cells are from a fibroblast 3T6 cell line.

In one embodiment, the present invention relates to a method of screening for agents which are capable of modulating or inhibiting Alzheimer's disease-like protein aggregation, e.g. pathological tau-tau association, the method comprising:

(1) causing or allowing the synthesis of a membrane-localised form of the aggregating disease protein (e.g. tau or MAP2), or a core fragment thereof (e.g. the core tandem repeat domain of tau or MAP2);

(2) contacting said fusion polypeptide or derivative with:

(A) one or more agents suspected of being capable of modulating or inhibiting aggregation of the aggregating disease protein molecules, and (B) a further aggregating disease protein or core fragment thereof, which is capable of binding to the membrane-associated protein of step (1); and (3) detecting the binding, if any, of the protein of step (2) (b) with the fusion polypeptide of step (1).

The tau-like protein used in step (2B) above may, in certain embodiments, be a "free" form of the protein, which term is used herein to distinguish it from the membrane-bound aggregating disease protein of step (1). However, "free" is not intended to exclude the possibility that the aggregating disease protein is complexed with, or otherwise associated with, other molecules or moieties such as carbohydrate moieties or other peptides.

For example, a test substance may be added to a cellular system as described above, and the cells incubated for a period of time sufficient to allow binding and to demonstrate inhibition of binding. The bound tau complex can then be detected, e.g. using a suitably-labeled antibody such as MAb 7.51 in an immunoblot of total cell extract, or any other suitable detection method. If desired, the membrane-bound tau protein can be distinguished from aggregated free tau protein, for example by terminating the sequence of the membrane-bound tau protein at amino aid 390. The aggregated free tau will be proteolytically cleaved at amino acid Gly 391, which can be detected by an antibody specific top that epitope (e.g. MAb 423).

Where a screening method is employed for this purpose, i.e. for the identification of modulatory/inhibitory compounds, a non-competitive or competitive assay may be used. For instance, in a competitive assay of the type well known in the art, the effect of a known inhibitor or modulator on Alzheimer's disease-like aggregation can be compared in the presence or absence of further test substances or agents, to determine the ability of the test substance to compete with the known inhibitor/modulator for binding to the protein of interest.

Choice of Test Compound

Compounds which are tested may be any which it is desired to assess for the relevant activity The methods can serve either as primary screens, in order to identify new inhibitors/modulators, or as secondary screens in order to study known inhibitors/modulators in further detail.

Agents may be natural or synthetic chemical compounds. Antibodies which recognise an Alzheimer's disease-like protein aggregate and/or which modulate Alzheimer's disease-like protein aggregation form one class of putative inhibitory or modulatory compounds with respect to the aggregation process. More usually, relatively small chemical compounds, preferably which are capable of crossing the blood-brain barrier, will be tested.

The skilled person will appreciate that the amount of test substance or compound which is added in a screening assay according to this aspect of the invention will normally be determined by trial and error depending upon the type of compound used. It may be selected to be a level which could realistically be used in therapeutic context i.e. would be non-lethal to a patient.

Specificity of Inhibition

Screening methods according to this aspect of the present invention may be used to screen for compounds which demonstrate the properties of selective competitive inhibition of pathological Alzheimer's disease-like protein aggregation (e.g. tau-tau or tau-MAP2 binding), without interference with the normal binding of e.g. tau or MAP2 to tubulin via the same region of the molecule (see WO 96/30766).

A suitable method for determining any possible interference of the binding of tau, MAP2 or a derivative thereof to tubulin by potential inhibitors/modulators of Alzheimer's disease-like protein aggregation, comprises contacting a preparation of depolymerised tubulin/MAP2 or taxol-stabilised microtubules with an agent suspected of being capable of modulating or inhibiting tau-tau or tau-MAP2 association, along with a protein or derivative thereof as mentioned above in step (2)(b), followed by detection of the tau-tubulin or MAP2-tubulin binding. Tau-tubulin binding could also, for example, be demonstrated by a normal cytoskeletal distribution, as described in e.g. WO 96/30766.

Methods for the preparation of tubulin proteins or fragments thereof, possibly in combination with binding partners, are known in the art and are described e.g. by Slobada et al. (1976, in: Cell Mobility (R. Goldman, T. Pollard and J. Rosenbaum, eds.), Cold Spring Laboratory, Cold Spring Harbor, N.Y., pp 1171-1212).

Cell Viability

Where the method utilizes a cell-based system, it may further include the step of testing the viability of the cells expressing the membrane-localised aggregating disease protein, e.g. by use of a lactate dehydrogenase assay kit (Sigma).

In the case where tau-tau, tau-MAP2 or MAP2-MAP2 aggregation is being investigated (see above, under 'specificity'), this step may also provide an indication of any interference by the test agent of the binding of tau or MAP2 to tubulin, since inhibition or interference of tau-tubulin or MAP2-tubulin binding will correlate to some extent with a decreased ability of the cells to divide, and thus with decreased cell viability.

Therapeutics and Modes of Administration

Performance of a screening assay method according to the various aspects above may be followed by isolation and/or manufacture and/or use of a compound, substance or molecule which tests positive for ability to interfere with or modulate disease related protein aggregation.

The compounds thus identified may be formulated into compositions for use in the diagnosis, prognosis or therapeutic treatment of Alzheimer's disease or the like (indeed any condition in which Alzheimer's disease-like protein aggregation occurs). Thus, the present invention also extends, in further aspects, to pharmaceutical formulations comprising one or more inhibitory or modulatory compound as obtainable by a screening method as provided herein.

Following the identification of a substance or agent which modulates or affects such protein aggregation, the substance or agent may be investigated further. Other candidate inhibitory/modulatory compounds may be based on modelling the 3-dimensional structure of a polypeptide or peptide fragment and using rational drug design to provide potential inhibitor compounds with particular molecular shape, size and charge characteristics. Thus the present invention provides the use of an agent as identified using a screening method provided herein, or a derivative, active portion, analogue, variant or mimetic thereof which is able to inhibit or modulate Alzheimer's disease-like protein aggregation, in screening for, or designing, further inhibitors/modulators of Alzheimer's disease-like aggregation.

A compound which has been identified as described above, may be manufactured and/or may be used in the preparation, i.e. the manufacture or formulation, of a composition such as a medicament, pharmaceutical composition or drug. These may be administered to individuals.

Generally, an inhibitor or modulator according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologically-acceptable excipients. As noted below, a composition according to the present invention may include in addition to an inhibitory/modulatory compound as disclosed, one or more other molecules of therapeutic use.

In this way, a substance according to the present invention, such as an inhibitor of tau-tau aggregation or other such Alzheimer's disease-like protein aggregation, may be provided for use in a method of treatment of the human or animal body of a condition in which Alzheimer's disease-like protein aggregation occurs.

The present invention thus extends, in various aspects, to a pharmaceutical composition, medicament, drug or other composition comprising a substance of the invention as described above, a method comprising administration of such a composition to a patient, e.g. for treatment or prophylaxis of Alzheimer's disease or an Alzheimer's disease-like condition, use of such a substance in the manufacture of a composition for administration, e.g. for treating Alzheimer's disease or similar treatment, and a method of making a pharmaceutical composition comprising admixing such a substance with a pharmaceutically acceptable excipient etc. as discussed below.

In particular the invention provides a method of modulating Alzheimer's disease-like protein aggregation in a cell, comprising administering an agent which inhibits or otherwise modulates such aggregation, the method therefore being useful in the treatment of Alzheimer's disease or other diseases or disorders in which Alzheimer's disease-like protein aggregation is implicated. The invention further provides a method of treating an Alzheimer's disease-like condition, which includes administering to a patient an agent which interferes with or otherwise modulates Alzheimer's disease-like aggregation of proteins.

Whether it is a polypeptide, antibody, peptide, nucleic acid molecule, small molecule, mimetic or other pharmaceutically-useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Examples of techniques and protocols mentioned above can be found in Remington's Pharmaceutical Sciences, 16$^{th}$ edition, Osol, A. (ed), 1980.

The agent may be administered in a localised manner to the brain or other desired site, or it may be delivered systemically in a manner such that it targets the brain or other cells. For instance, targeting therapies may be used to deliver the active agent more specifically to certain types of cell, by the use of targeting systems such as antibody or cell-specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be administered in a precursor form, for conversion to the active form by an activating agent produced in, or targeted to, the cells to be treated.

An agent which is able to interfere with Alzheimer's disease-like protein aggregation may be provided in a kit, e.g. sealed in a suitable container which protects its contents from the external environment. Such a kit may include instructions for use.

Animals

Although much of the forgoing discussion has been concerned with cell-line or in vitro-based assays, the invention disclosed herein has particular utility in animal-based assays.

Thus host cells according to the present invention may be comprised in a transgenic animal, and the present invention further provides a transgenic animal, comprising cells which express a fusion polypeptide according to a preceding aspect, such as a membrane-localised form of the tau core fragment. Such animals may be prepared and\or used in analogous manner to those discussed in U.S. Pat. Nos. 5,912,410 and 5,898,094 which disclosures are incorporated herein by cross-reference.

The transgenic organisms of the invention all include within a plurality of their cells a cloned recombinant or synthetic DNA sequence which is believed to relate to the pathogenesis of a disease of protein aggregation. More specifically, the transgenic organisms contain specific sequences of exogenous genetic material, such as the sequences described above in detail which are comprised of a tissue specific promoter sequence and a sequence which encodes for production of a membrane targeted protein. Since it is possible to produce transgenic organisms of the invention utilizing one or more of the above-described sequences, a general description will be given of the production of transgenic organisms by referring generally to exogenous genetic material. This general description can be adapted by those skilled in the art in order to incorporate the above-described specific DNA sequences into organisms and obtain expression of those sequences utilizing the methods and materials described below. For more details regarding the production of transgenic organisms, and specifically transgenic mice, refer to U.S. Pat. No. 4,873,191, issued Oct. 10, 1989 (incorporated herein by reference to disclose methods producing transgenic mice), and to the numerous scientific publications referred to and cited therein.

The exogenous genetic material may be placed in either the male or female pronucleus of the zygote. More preferably, it is placed in the male pronucleus as soon as possible after the sperm enters the egg. In other words, right after the formation of the male pronucleus when the pronuclei are clearly defined and are well separated, each being located near the zygote membrane. The male pronucleus of a fertilized mouse egg is the preferred site for addition of the exogenous genetic material of the present invention.

It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material could then be added to the ovum or the decondensed sperm could be added to the ovum with the exogenous genetic material being added as soon as possible thereafter.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the DNA sequences which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of a gene, in order to insure that one copy is functional. As regards the present invention, there is generally an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Thus the present invention provides methods in which cloned recombinant DNA sequences encoding appropriate membrane targeting sequences may be injected into fertilized mammalian eggs (preferably mouse eggs). The injected eggs are implanted in pseudo pregnant females and are grown to term to provide transgenic mice whose cells express proteins related to the pathology of the relevant disease. The injected sequences are constructed having promoter sequences connected so as to express the desired protein in specific tissues of the transgenic mammal (most notably in nerve tissue). Suitably, the vector is adapted for neurone-specific expression to produce Alzheimer's Disease-like aggregation such as is now known to occur in the human brain. Examples may include the prion specific promoter of Lewis et al (2000) or the neurospecific enolase promoter e.g. of Thunecke et al (2000).

Non-human animals of the invention may be homozygous or heterozygous for the fusion polypeptide. Mammalian animals include non-human primates, rodents, rabbits, sheep, cattle, goats, pigs. Rodents include mice, rats, and guinea pigs. Specifically provided are:

Methods of preparing a transgenic animal model with enhanced or accelerated pathology for a disease of protein aggregation and the transgenic animal made by such methods.

Methods of producing an $F_1$ generation by crossing a founder animal of either sex ($F_0$ generation) with an animal which is non-transgenic in respect of the proteins discussed herein, and is preferably wild-type). The offspring ($F_1$ generation) may then be screened and those which carry a transgene resulting in an enhanced pathology for the disease, are selected.

Methods of producing an $F_2$ generation by crossing 2 $F_1$ animals of appropriate sex. The offspring ($F_2$ generation) may then be screened and those which carry a transgene in the appropriate dosage (i.e. hetero or homozygous) resulting in an enhanced pathology for the disease, are selected.

A method of modulating the disease phenotype of a transgenic animal model, and the transgenic organism with the modulated phenotype, as described above.

Transgenic non-human mammals of the invention may thus be used for experimental purposes in studying Alzheimer's-like diseases, and in the development of therapies designed to alleviate the symptoms or progression of such conditions. By "experimental" it is meant permissible for use in animal experimentation or testing purposes under prevailing legislation applicable to the research facility where such experimentation occurs.

The animal may be used to screen for or test potential diagnostic, therapeutic or prognostic agents of Alzheimer's disease-like protein aggregation (see below for further discussion). This aspect of the invention thus provides an animal model which can aid in the investigation of Alzheimer's disease and Alzheimer's disease-like conditions. In the in vivo model system, the Alzheimer's disease-like condition is induced in the animal by causing or allowing a membrane-localised Alzheimer's disease-like protein aggregate to be synthesised in the cells. Using this model system, a compound suspected of having a therapeutic effect in relation to Alzheimer's disease or an Alzheimer's disease-like condition can be administered to the animal, and any effects on the condition (e.g. improvements in symptoms, or any other suitable indicator) can be studied. In particular, the transgenic mammals of the present invention are useful in determining the effectiveness of pharmaceutical drugs with respect to their ability to decrease the amount of aggregates which form within the brain of the animal. These aggregates may be measured by biochemical and\or histological techniques used in measurements of AD in humans (see e.g. Mukaetova-Ladinska, E. B. et al. (2000) loc cit.).

Most preferably the aggregation (or inhibition thereof) is assessed by the production (or inhibition, or abolition, of production) of truncated fragments of tau resulting from proteolytic processing e.g. of endogenous, full length, tau. In preferred embodiments the aggregation of tau is evidenced by proteolytic processing to a truncated core fragment corresponding to that found in the actual AD PHF core. However the production of any one or more other fragments which are diagnostic products or bi-products of this process may also be used.

The mammals are thus useful in testing the efficacy of such drugs, in a pharmacokinetic context, in preventing the formation or reducing the amount of aggregation formed as well as eliminating or reducing aggregation already formed.

Generally speaking, a drug to be tested is administered to a control animal or group of animals which are not the transgenic animals of the invention and simultaneously to transgenic animals of the invention. The drug is preferably continuously administered over a period of time which is normally sufficient to effect the formation of aggregates in the brain of the animal. After administering the drug for a sufficient period of time the control animal(s) along with the transgenic animal(s) are sacrificed. Examination of the brain of the animals is made as described above.

In such a system, the effect of a potential inhibitor or modulator of protein aggregation can be determined or detected as described above e.g. by immunoassay, for instance to observe the inhibition of the formation of tau, or tau-like aggregates such as those detected in human brain tissue by the methods of e.g. Wischik et al. (1995; loc. cit.), Lai et al. (1995; loc. cit.), or Mukaetova (2000; loc. cit.) in which measurement of aggregated forms of tau protein is undertaken in brain tissues.

For instance, the production of aggregates within cells may be visualized histologically and by electron microscopy, and the prevention of these aggregates similarly assessed.

By comparing the amount of aggregate deposit within the control animal(s) to the amount of deposit within the transgenic mammal(s) of the invention a determination can be made with respect to the effectiveness of the drug. Comparative drug testing protocols known to those skilled in the art can be used in connection with the transgenic mammals of the invention in order to test drugs. The final intracellular concentration of the drug may be selected to be appropriate to the precise disease protein and drug in question, but may be in a range which will ultimately be appropriate for clinincal usage in terms of toxicity, uptake etc. (e.g. 1 µM-1 mM more preferably 4-600 µM).

The in vivo screening assay of the invention need not directly measure the degree of inhibition of, or modulation of, Alzheimer's disease-like protein aggregation caused by the compound being tested. Instead the downstream effect on the pathological condition itself, e.g. Alzheimer's disease, may be measured. For instance, it would be anticipated that there would be behavioral effects in the animals, such as defects of movement, power or tone, abnormal reflexes, evidence of defective memory or response to environmental cues.

In that the transgenic animals of the invention can be used to test the efficacy of drugs with respect to preventing disease-associated protein aggregation, the animals are valuable research tools with respect to allowing researchers to test the efficacy of such drugs in treating diseases such as Alzheimer's disease. If preferred, in all cases, the transgenic animal assay may be run in parallel with, or subsequent to, an in vitro or cell-based assay, e.g. according to preceding aspects of the present invention, in order to confirm that any effect on the condition itself is as a result of the inhibition of Alzheimer's disease-like protein aggregation and not merely a general toxic effect.

Thus, as is described in detail above, the present invention relates inter alia to the use of a nucleic acid molecule, polypeptide or derivative thereof, a host cell, a transgenic animal or an in vitro membrane-localized model system, all as provided herein, in methods of screening for test substances having an inhibitory or modulatory effect on Alzheimer's disease-like protein aggregation. In further aspects, the present invention extends to inhibitory or modulatory compounds obtainable using a screening method of a preceding aspect.

Various further aspects and embodiments of the present invention will be apparent to those skilled in the art in view of the present disclosure. Certain aspects and embodiments of the invention will now be illustrated by way of example only, and with reference to the following Figures and Examples.

FIGURES

FIG. 1 shows a diagrammatic illustration of an assay according to the invention as described in Example 1 (cell based) and Example 3 (animal model).

(A) (1:) Assay based on constitutive expression of membrane-targeted sequence alone, in this case a Signal Sequence plus truncated tau (Sstau190-441). The membrane associated molecules combine leading to formation of a 25 kD fragment. As shown in FIG. 17(A) the 25 kD fragment contains immunoreactivity associated with the repeat domain and the C-terminus, but not an epitope located between residues 208-238. The fragment length is ~175 residues and the likely N-terminal cleavage site is at residue ~266, the phase-shifted N-terminus of the first repeat found in tau protein isolated from the PHF-core.

(A) (2:) Assay based on second protein (T40—full-length tau), the proteolytic cleavage of which is "seeded" by the presence of low background levels of SStau190-441 which is targeted to the endoplasmic reticulum by the signal sequence. T40 induced by IPTG is bound to the SStau190-441 species either at the membrane or after release of the SStau190-441-derived aggregate into the cytosol. This captured T40 is now further processed first to give rise to increased levels of a species with gel mobility and immunoreactivity identical to that of the SStau190-441-derived species. It is then further processed through the same pathway to generate increased levels of the 25 kD degradation product. Tau aggregation inhibitors block T40-derived production of the 25 kD fragment in the presence of IPTG.

(B) Assay based on second cleavage pattern of SStau190-441. In this case the membrane-associated molecules combine in a slightly different manner through the repeat region to give rise to three further truncation products (seen in FIG. 17(A)) with gel mobilities 30 kD ~200 residues), 18 kD ~125 residues) and 12/14 kD 95 residues).

(C) Assay based on constitutive expression and aggregation of SStaul 90-390. In this case, proteolytic processing gives rise to a single predominant species with gel mobility of 18 kD (~125 residues). This arises by aggregation of SStau190-390 molecules through the repeat domain, giving rise to a proteolytically protected fragment derived entirely from the repeat domain (ie ~266-~390). In a variant of the repeat domain binding pattern, illustrated in FIG. 17(B)), a slightly different 18 kD species could arise by association of SStau190-390 with low background levels of T40, to give rise to a fragment equivalent to 4-repeats in length (ie ~125 residues), but extending by the equivalent of 1 repeat beyond 390 within the C-terminal tail of the molecule (ie ~295-~422). In a different scheme illustrated in FIG. 16D, small quantities of a fragment consisting of only 3 repeats (ie ~95 residues) are able to form minority dimeric forms with a typical gel mobility corresponding to ~19/22 kD.

(D) Assay based on constitutive expression of SStau296-390 in the presence of background T40. In this case, two predominant species are formed, one of 12/14 kD corresponding to the Sstau296-390 fragment itself, and a further species with gel mobility of 18 kD. The latter cannot be a degradation product of SStau296-390. It is also unlikely to be a major form of the dimer (see FIG. 16D) which has a predominant gel mobility corresponding to 24 kD. Therefore, the 18 kD is most likely to arise by truncation of T40which has been captured by an SStau296-390 aggregate. This species again corresponds to the equivalent of 4 repeats (ie ~125 residues), and could arise through two possible binding interactions between T40and the SStau296-390 aggregate as shown. In this model the rate limiting step for the formation of the 18 kD species from T40may be the determined by the amount of aggregating, truncated, tau in the system.

(E) Assay based on constitutive expression of SSttau296-390 within the transgenic mouse brain. As in the system described in (D), the predominant product is not the SStau296-390 itself, but a higher molecular weight species of 18 kD. For the reasons discussed above, this is unlikely to be a dimer or a degradation product of the SStau296-390 species introduced into the animal transgenically. Rather, it is most likely to arise by the capture and proteolytic processing of endogenous mouse tau. In this case, the mouse brain is known to express only the 3-repeat isoform. The 18 kD fragment generated in this case is most likely to be the form with the C-terminal extension giving rise to a species the equivalent of 4 repeats in length (~125 residues, or the fragment between residues ~266 and ~422 in the 3-repeat isoform). However, a slightly different binding pattern is also possible, in which the extension is into the N-terminus (ie the fragment between residues ~235 and ~390 in the 3-repeat isoform)

Figure 2:
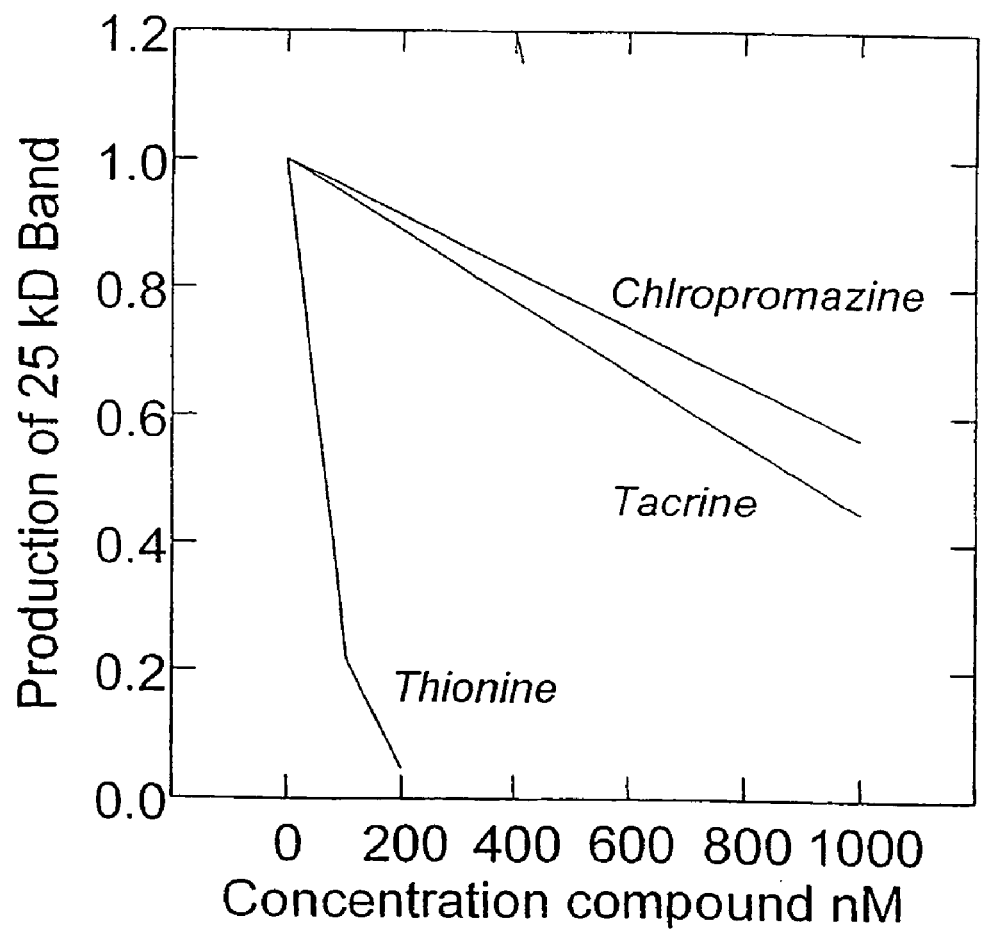

FIG. 2. The inhibitory activities of thionine, chlorpromazine and tacrine were compared in the membrane-targeted cell model (production of 25 kD species). There is a clear distinction between active and inactive compounds (see Example 2).

Figure 3:
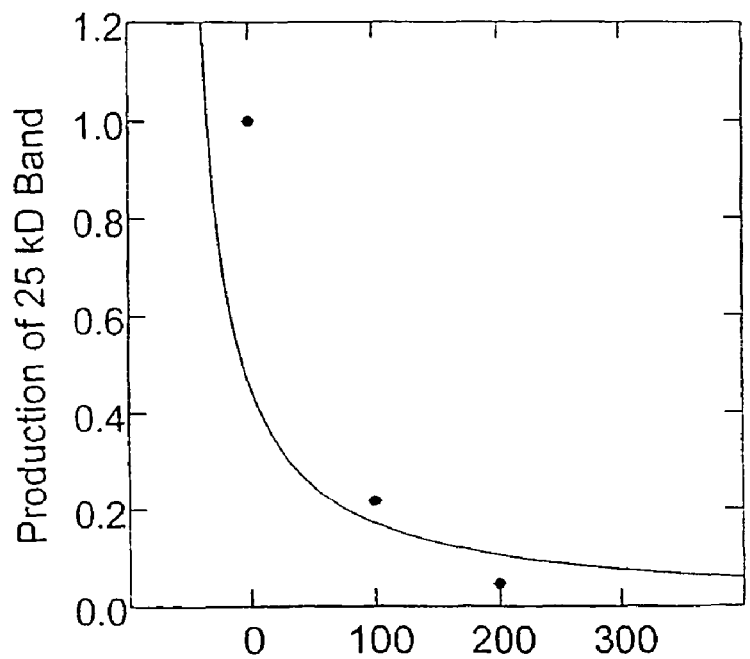

FIG. 3. The data from FIG. 2 was analysed in greater detail mathematically using a standard inhibitory model, and a numerical procedure (Gauss-Newton method) to solve for KI. The data could be approximated very closely by assuming a Kd value for tau-tau binding within the cell of ~500 nM, and a corresponding KI value of ~33 nM. The significance of these values can be understood by comparing with what is known of the influence of phosphorylation on tau-tau binding in vitro (see Wischik, C. M., et al. (1997) loc cit).

Figure 4B:
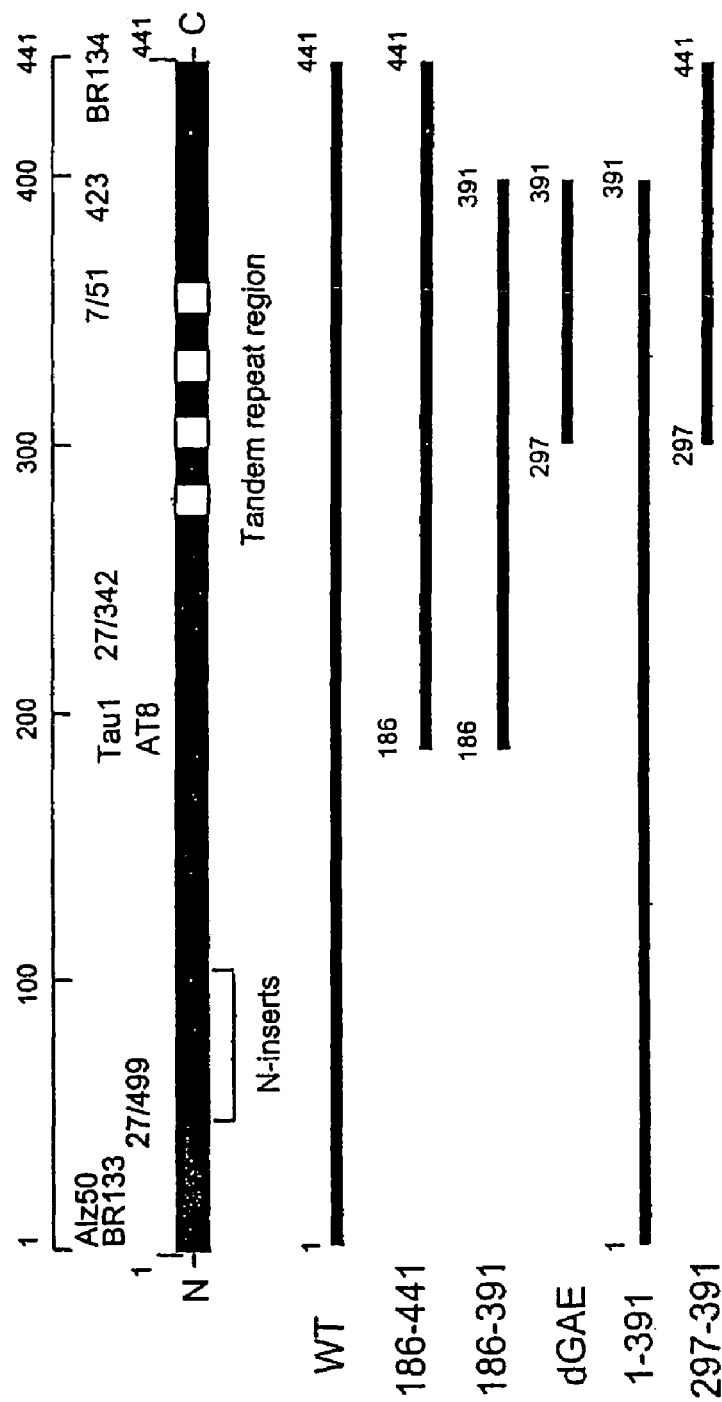

FIG. (4A) shows a schematic illustration of the structure of a paired helical filament (top) and the immunochemistry of neurofibrillary tangles during progression of Alzheimer's disease (bottom). FIG. 4(B) shows a schematic illustration of the binding sites of various monoclonal antibodies to different forms of N- and C-truncated tau.

FIG. 5(A) shows the nucleotide sequence (SEQ ID NO: 1) and predicted amino acid sequence (SEQ ID NO: 2) of a human tau protein isoform. The sequence was deduced from cDNA clone htau40. FIG. 5(B) shows the sequences of some of the constructs of the present invention.

Figure 6A:
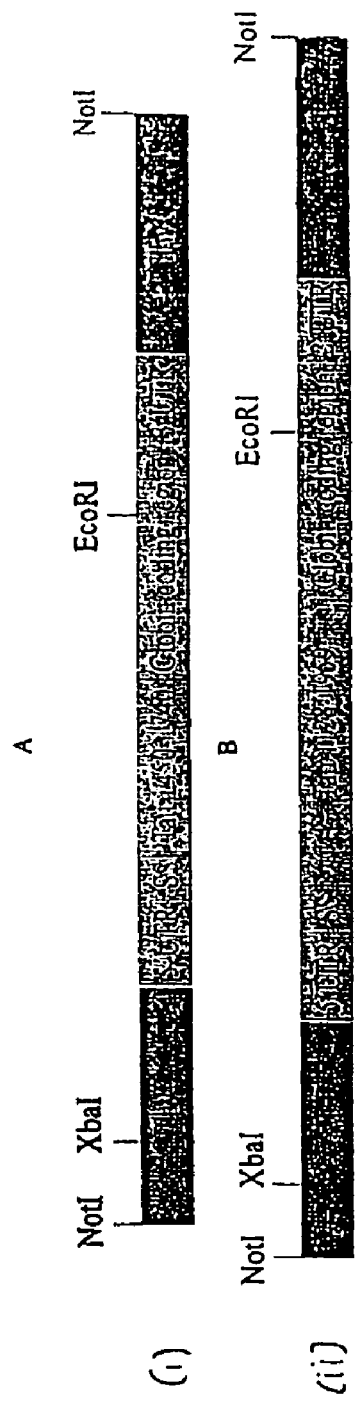
Figure 6B:
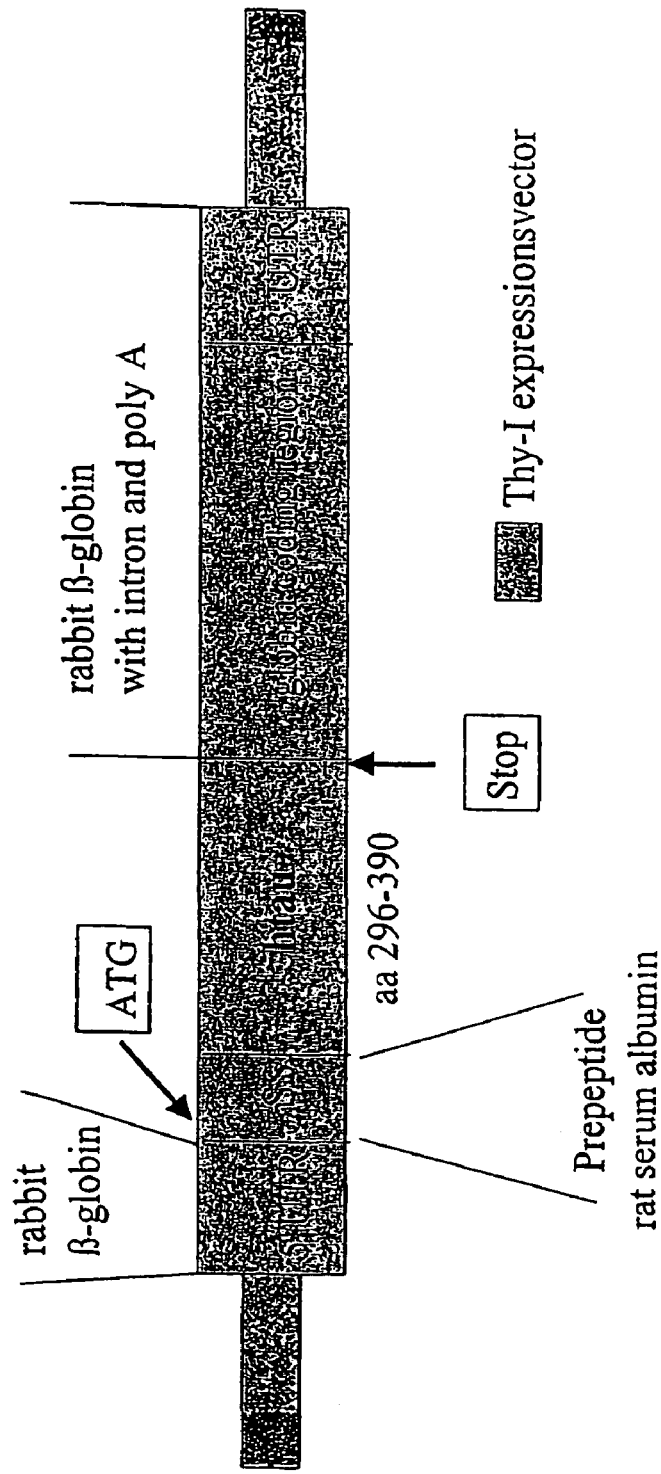

FIG. 6(A) shows constructs used for microinjection to prepare transgenic mice. These are (i) Thy1-sstau296-390, and (ii)
Thy1 -sstau1 86-441. FIG. 6(B) shows construct Thy1-Stau296-390 in more detail. This was cloned into the Thy-1 expression vector and was then microinjected into fertilized oocytes of NMRI mice using methods from: "Manipulating the mouse embryo", a laboratory manual, second edition, Cold Spring Harbour Press, CSH, N.Y. Hogan, B., Beddington, R., Costantini, F., Lacy, E., editors, 1994).

Figure 7:
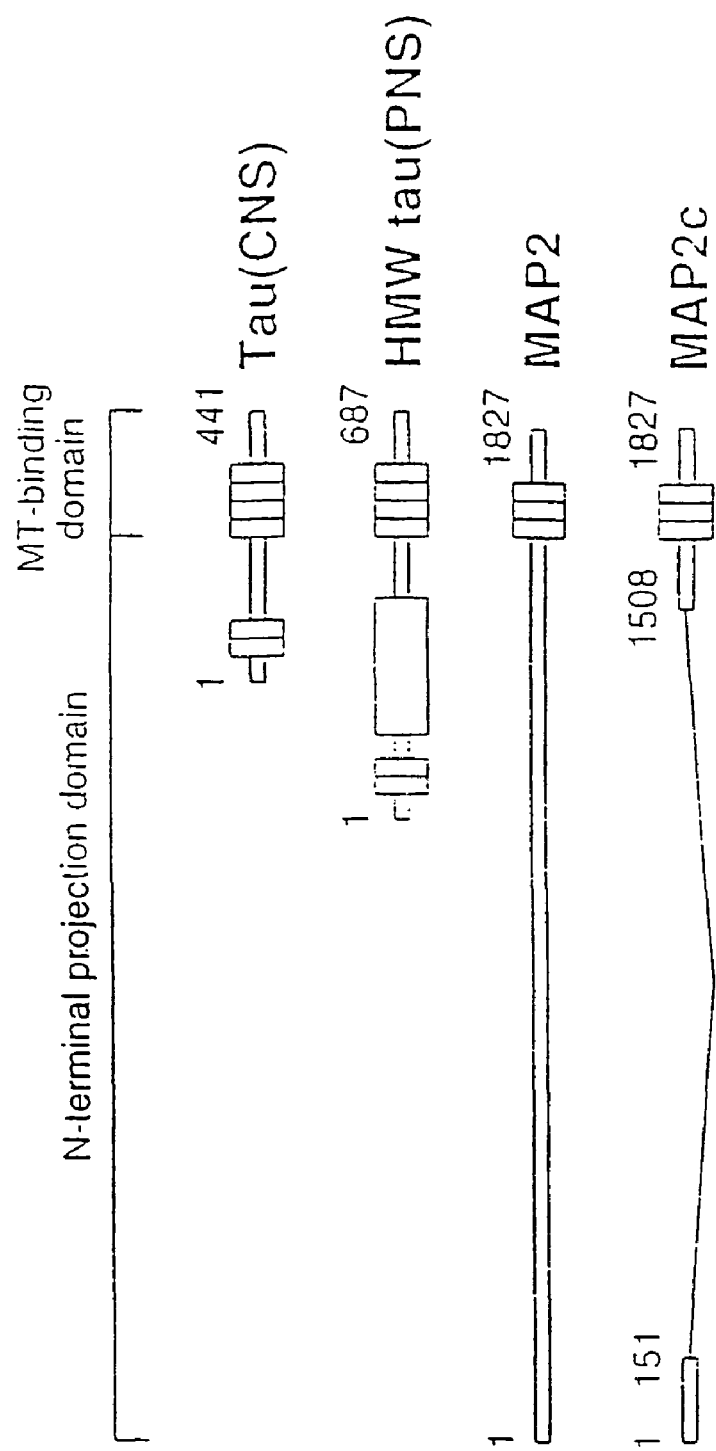

FIG. 7 shows a schematic representation of tau, MAP2 (adult form), MAP2C (juvenile form) and high molecular weight tau (found in the PNS and neuroblastoma cell lines). These proteins share similar microtubule-binding domains, but differ substantially in sequence and extent of the N-terminal projection domain. The juvenile forms of tau and MAP2 have only 3 of the tandem repeats. A 4-repeat form of MAP2 also exists.

Fig. 8 shows sequence differences in the tandem repeat region of human tau (upper line(Seq ID No. 6)) and human MAP2 (lower line(Seq ID No. 7)). Vertical arrows show the limits of the truncated PHF-core fragment terminating at Glu-391, and the tubulin-binding segments are shown underlined.

Figure 9:
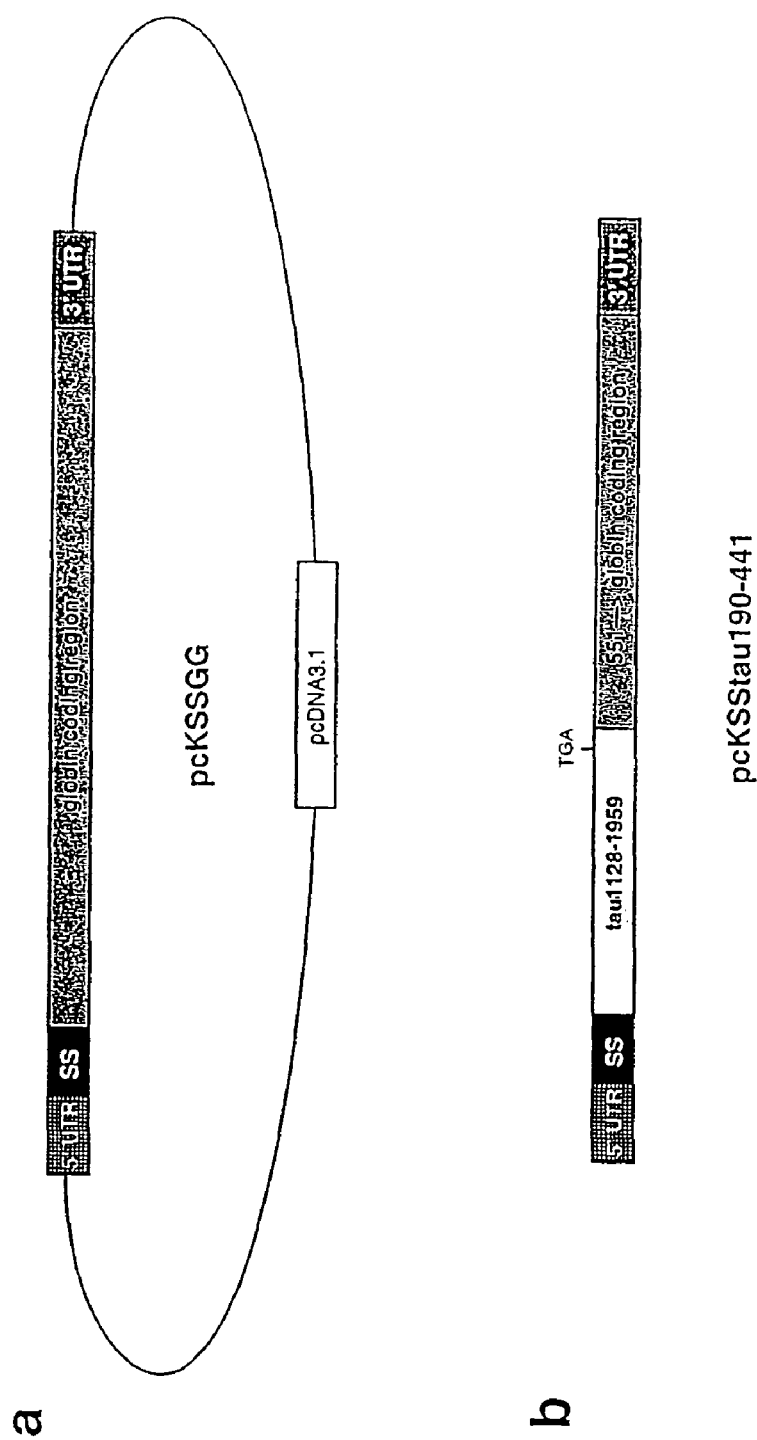

FIG. 9 shows a construct according to one embodiment of the present invention. (A) The signal sequence of rat albumin was inserted in front of the start codon of the cDNA encoding rabbit globin to achieve membrane targeting of the globin mRNA. FIG. 9(B) shows a fragment of the human tau cDNA encoding amino acids 190-441 was inserted to replace part of the globin sequence, to effect expression of a tau fragment with an N-terminal signal sequence. The globin 5' and 3' UTRs were retained in the construct.

FIG. 10 shows a summary of tau fragments of the present invention which were expressed in host cells. Three fragments of tau, all containing the core aggregation domain, were expressed with N-terminal signal sequences. For comparison, soluble forms of two of the fragments were also expressed, as well as full-length tau.

Figure 11:
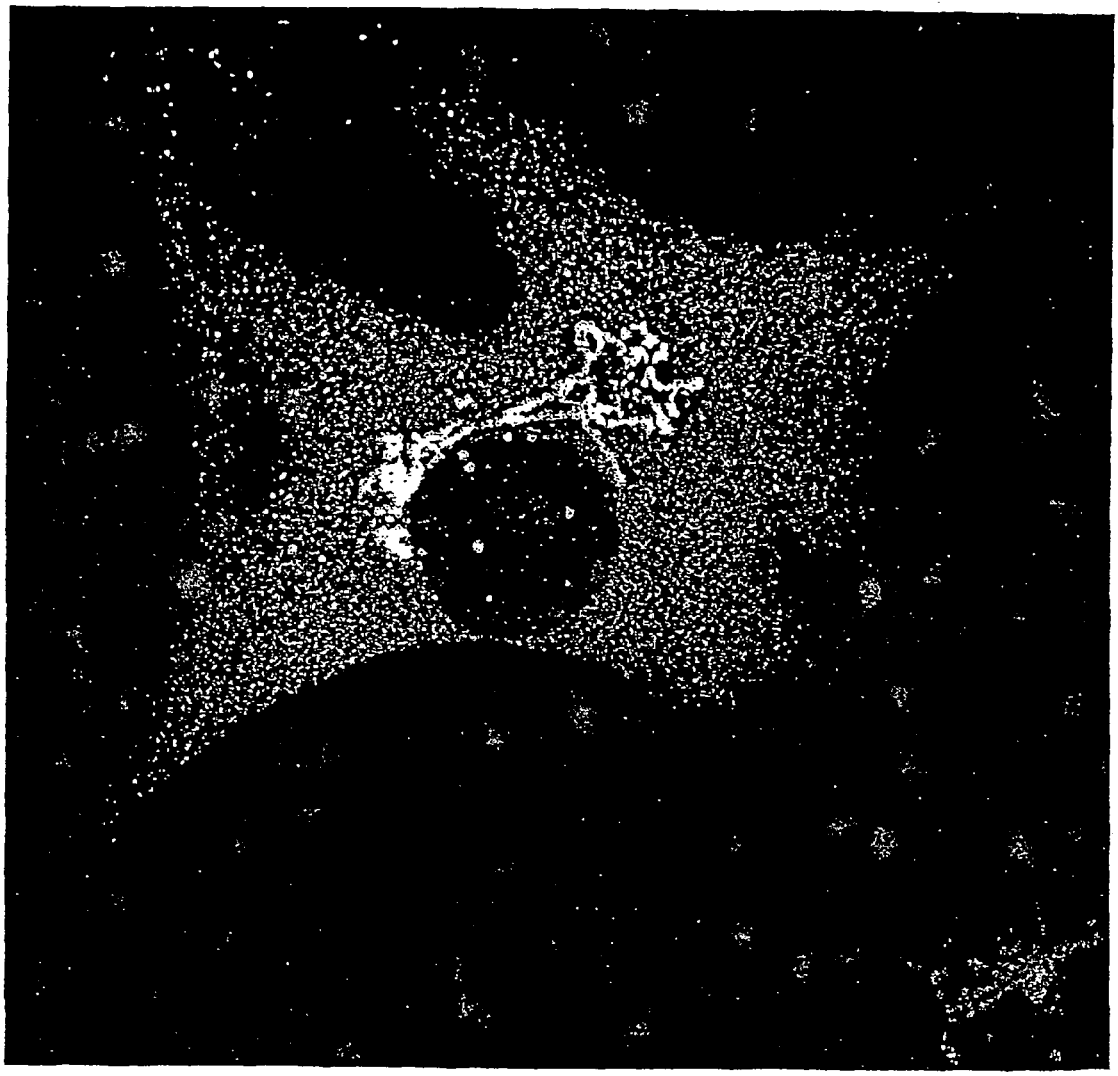

FIG. 11 shows the localization of SStau190-390 after stable transfection of 3T6 cells. 3T6 cells isolated as stable clones after transfection with a cDNA encoding amino acids 190-390 of the longest isoform of human tau linked to an N-terminal signal sequence were incubated with 5 mM sodium butyrate for 20 h to increase protein expression, fixed with parafomaldehyde and labeled with mAb 7.51 directed against the repeat domain of tau. These cells show similar tau morphology to cells expressing SStau190-441, but cells isolated after stable transfection with SStau190-390 consistently showed higher levels of expression of the tau fragment, with a higher proportion showing large tau aggregates (see Example 1)

Figure 12:
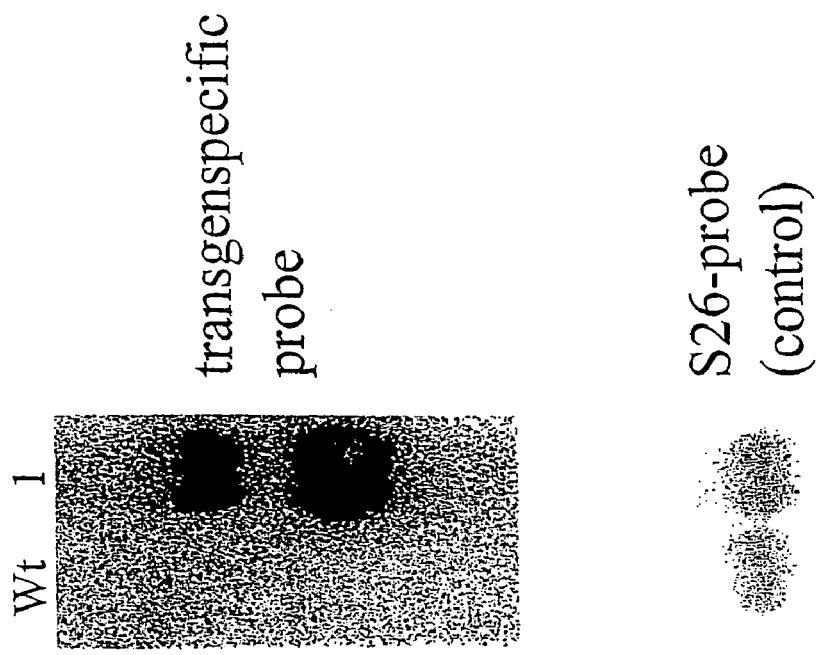

FIG. 12 shows a Northern blot analysis of wild-type ("Wt") and transgenic mouse line 1 ("1") RNA with a specific probe showing a high expression level of transgenic RNA in transgenic mouse line 1. S26 control shows same loading amounts (see Example 3).

Figure 13:
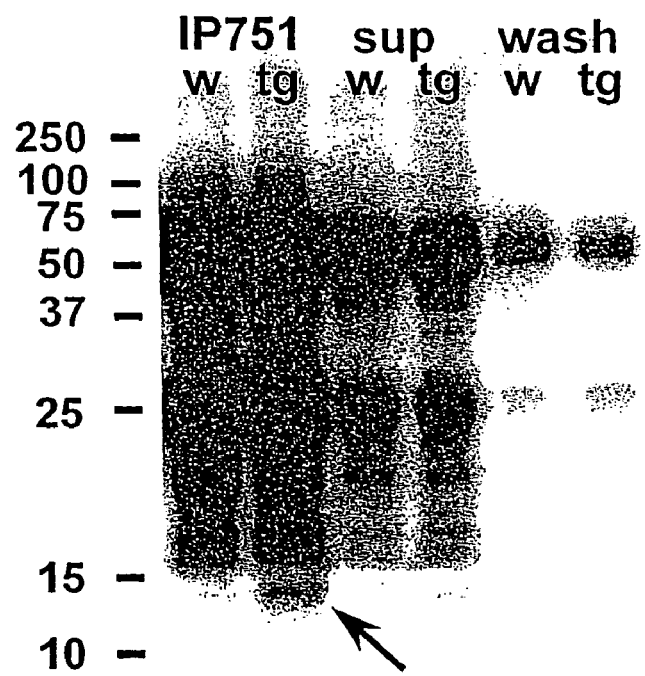

FIG. 13 shows purification of the SStau290-391 by immunoprecipitation using mAb 7.51. 0.1 g mouse brain was homogenized using 500 µl lysis buffer (150 mM NaCl, 0.01% SDS, 0.1% NP40, 50 mM Tris, 100 µg/ml PMSF, 1 mM DTT, 1 µg/ml Leupeptin). The suspension was then sonicated on ice for 1 min and spun down with a benchtop (Eppendorf) centrifuge at 14,000 rpm for 4 min. This leads to the "S1" supernatant fraction. The first immunoprecipitation was undertaken using mAb 342 to deplete the preparation of endogenous mouse tau. The S1 fraction was incubated with 1/10 volume of antibody 342 (1:10), incubated for 2 h at 4° C. with rocking, then 100 µl of ProteinA sepharose beads (10% v/v in lysis buffer) were added, incubated for 1 h at 4° C., centrifuged with a benchtop centrifuge at 14,000 rpm for 30 sec. Supernatant was taken for further immunoprecipitation using mAb 7.51. 1/10 v/v of 7.51 was added, incubated for 2 h at 4° C. with rocking. 40 µl of ProteinA sepharose beads were added, incubated for 1 h at 4° C., centrifuged for 15 sec at 14000 rpm, washed 3 times with the above mentioned lysis buffer. Then, 30 μl of laemmli sample buffer was added, heated to 85° C. for 5 min, centrifuged for 30 sec. Supernatant was then loaded onto 15% SDS-Page gel. The IP751 lanes indicate a difference at ~12-14 kD corresponding to presence of the SStau290-391 protein product in a transgenic animal from line 1. The dark background at higher molecular weight is due to presence of endogenous mouse immunoglobulins detected in the course of development of the immunoblot (see Example 3).

Figure 14:
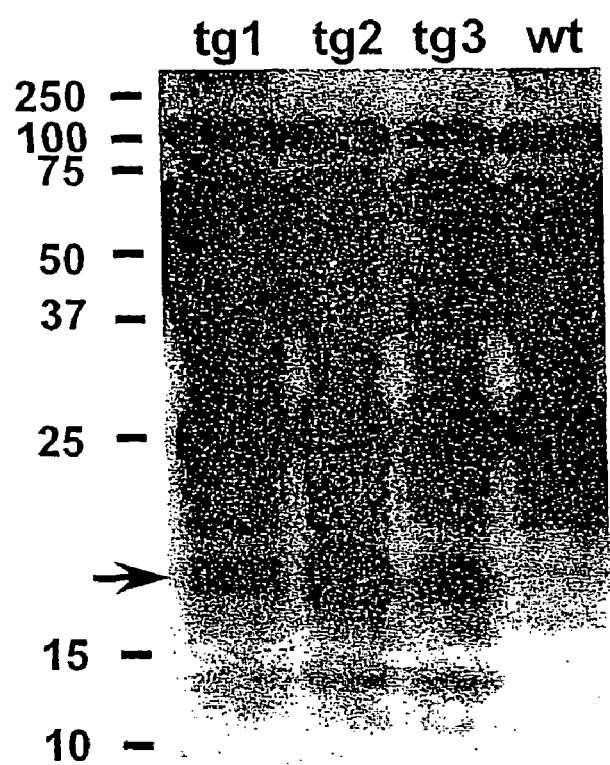

FIG. 14 shows the S1 fraction prepared in lysis buffer as indicated above without immunoprecipitation. Immunoblotting using mAb 7.51 revealed in addition to the ~12-14 kD band corresponding to the transgene a new more prominent species with gel mobility ~18 kD. This was seen in all line 1 individuals to varying degrees according to the age of the animal up to 15 months. Three are shown of ages 5 months, 4 months and 4 months respectively. Epitope mapping (not shown) demonstrated that the 18 kD species was recognised recognised by mAb 7.51 (epitope in the repeat domain) and a polyclonal antiserum K9JA ("DAKO A/S", also recognising epitopes located in the repeat domain of tau). The 18 kD species was not recognised by the C-terminal polyclonal antiserum T46.1 or mAb 342, which recognises an epitope located between residues 208-238. The 18 kD species cannot arise as a degradation of product of the transgene product, nor can it arise as a dimer of SStau296-390. The 18 kD species is therefore likely to be generated by aggregation-dependent proteolytic processing of endogenous mouse brain tau as shown in FIG. 1.

Figure 15:
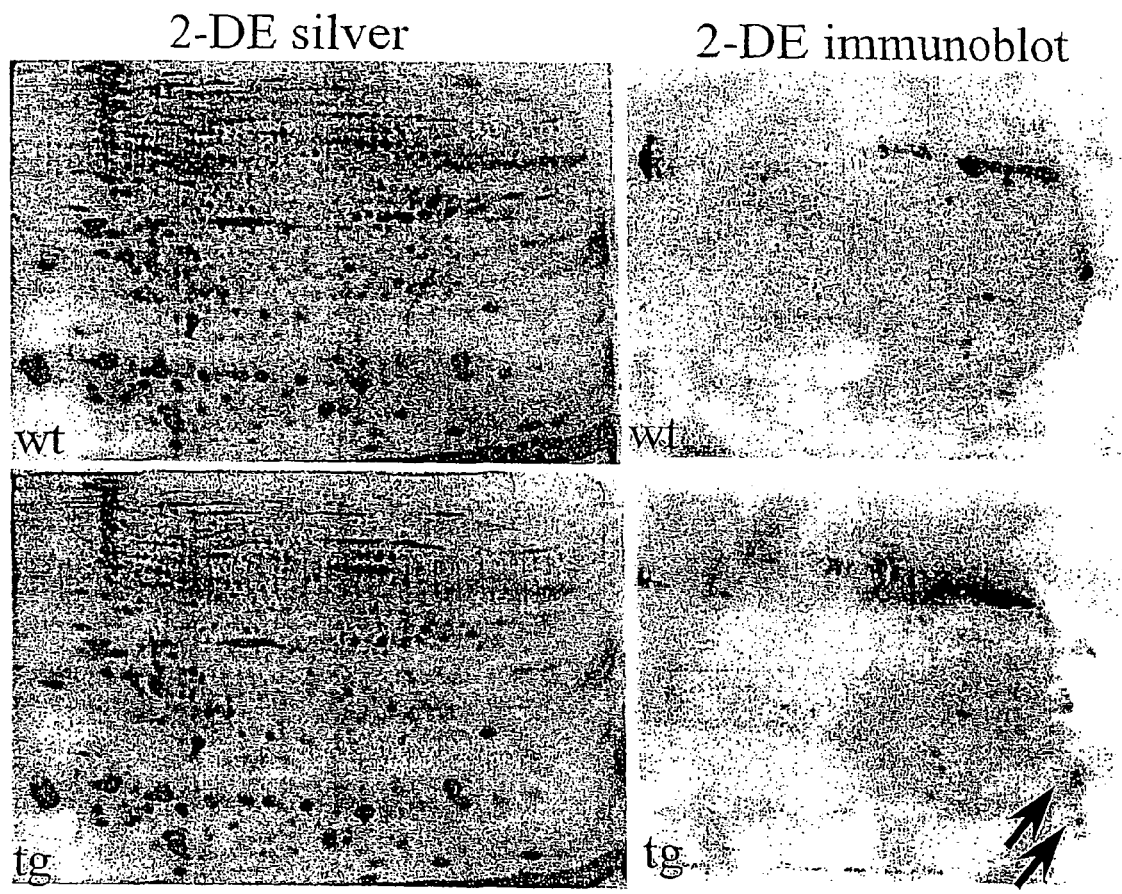

FIG. 15 shows two dimensional gel electrophoresis (2DE), silver stain and immunoblotting. 500 mg of mouse brain was homogenized in 2 ml of lysis buffer (see above), sonicated on ice, centriguged at 14000 rpm. The S1 fraction was taken and boiled for 5 min at 95° C., centrifuged at 14000 rpm for 5 min, supernatant was taken and concentrated 10-fold using a centricon3000. 20% of this protein suspension was loaded onto a 2-DE gel. $1^{st}$ dimension isoelectric focusing, $2^{nd}$ dimension 15% SDS-PAGE. Gels were silver stained and in parallel gels were run under same conditions and blotted, then incubated with 7.51 antibody (see above). The black arrows show the 12-14 kD gene product and a doublet corresponding to the 18 kD species. In addition there is an as yet uncharacterised smear of lower gel mobility which also distinguished the transgenic animal from the wild-type. This smear is likely to contain several higher molecular weight tau products also derived from endogenous mouse tau. Other isolated higher molecular weight tau-immunoreactive spots are also variably observed, depending preparative protocol used (see Example 3).

FIG. 16 shows the results obtained with the various cell lines of Example 1.

Figures 16A, 16B:
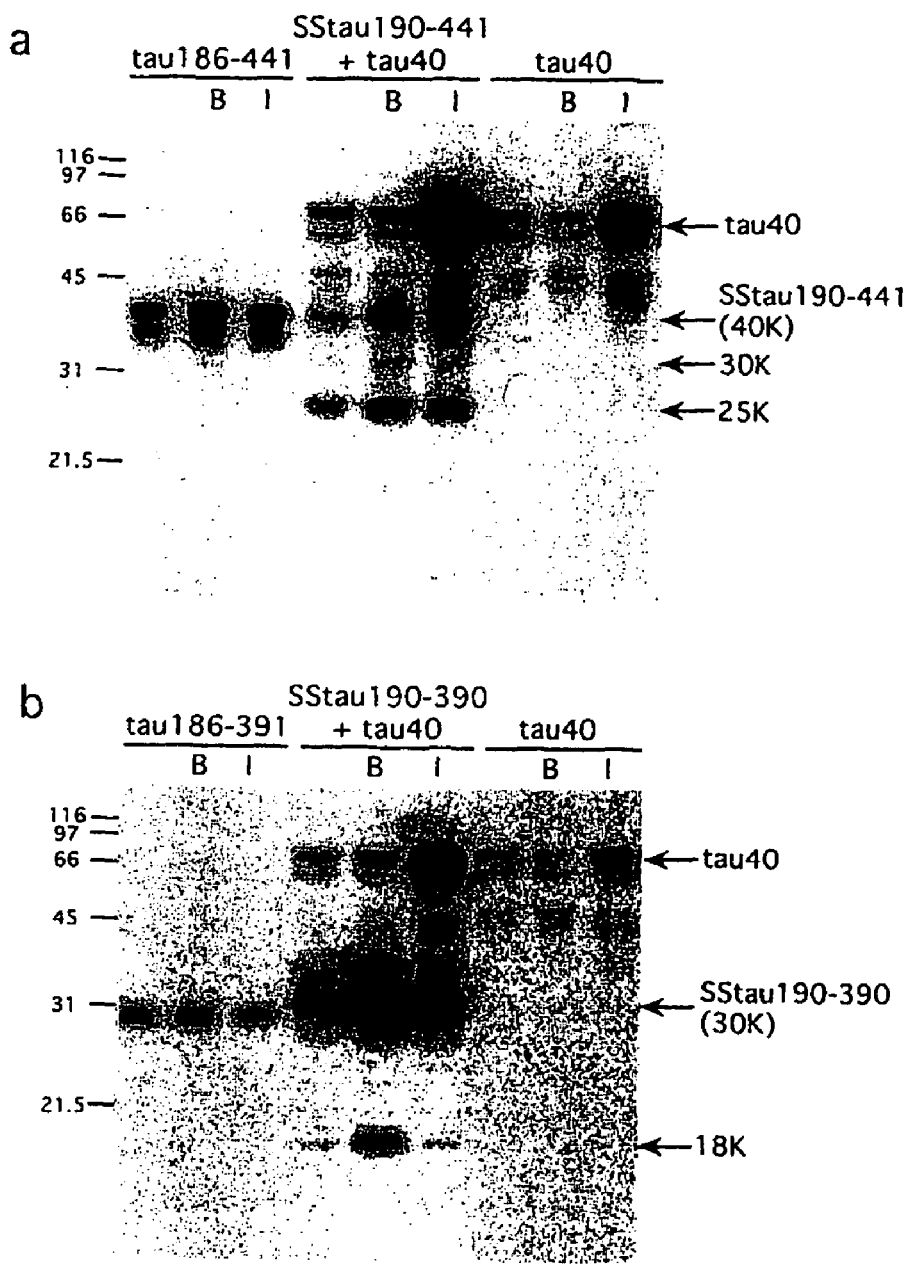

FIG. 16(A) shows an analysis of cells expressing tau fragments by immunoblotting. Cells stably expressing tau fragments, and also expressing full-length tau under the control of an IPTG-inducible promoter, were incubated with 5 mM IPTG or 5 mM sodium butyrate for 24 h before analysis on 15% SDS gels followed by immunoblotting with the mAb 7.51, which binds to an epitope in the repeat domain of tau. The Sstau190-441 protein has an apparent RMM of ~40K on gels, and is degraded to a fragment of ~25K. In contrast the soluble tau186-441 fragment and soluble T40show different degradation profiles. Induction of full-length tau (I) in cells expressing Sstau190-441 causes increased appearance of the 40K, 25K proteins, and possibly a small amount of a 30K fragment. Increasing expression of the transfected protein by addition of sodium butyrate (B) also increases the amount of both fragments, and induces the appearance of the 30K fragment.

In FIG. 16(B) the The SStau190-390 protein has an apparent RMM of ~30K, with a small amount of a degradation product at ~18K. Induction of full-length tau causes a slight increase in the amount of the 30K protein. Butyrate treatment causes a larger increase in the amount of the 30K fragment, and also increases the amount of the 18 kD fragment. This pattern of degradation is not seen for the soluble 186-391 fragment or the full length T40.

Figure 16C:
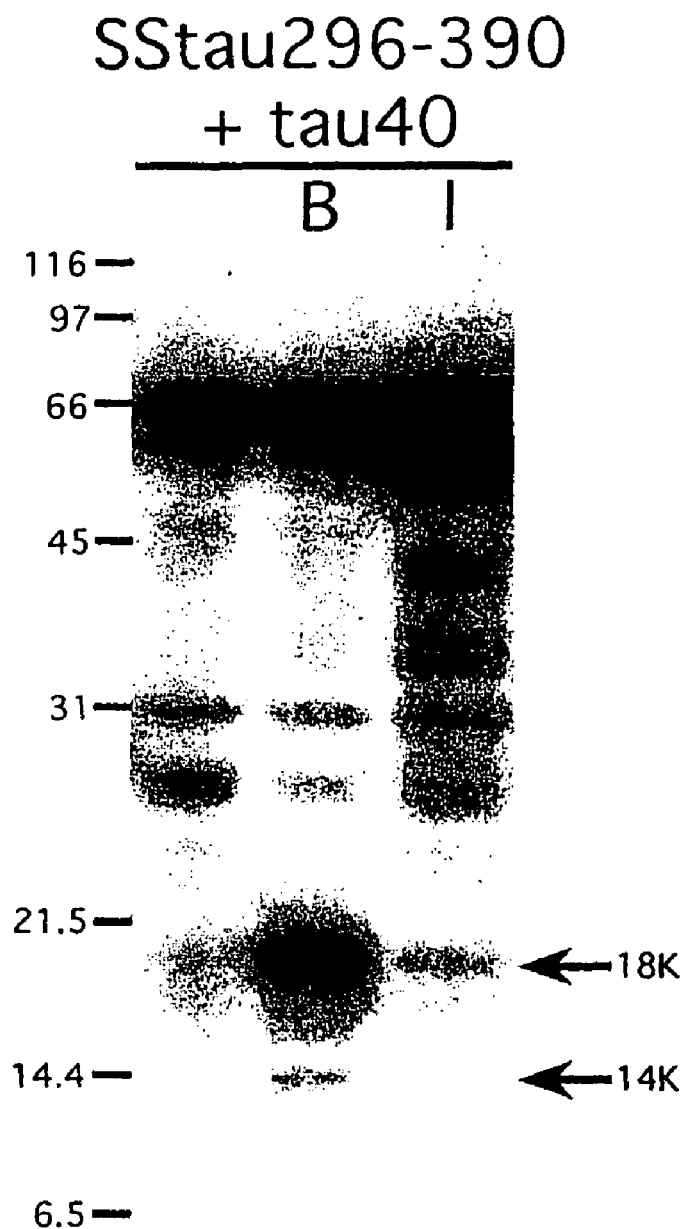

FIG. 16(C) shows an analysis of cells expressing tau fragments by immunoblotting. Cells stably expressing the tau fragment SStau296-390 and also expressing full-length tau under the control of an IPTG-inducible promotor, were incubated with 5 mM IPTG ("I") or 5 mM sodium butyrate ("B") for 24 h before analysis on 15% SDS gels followed by immunoblotting with mAb 7.51, which binds an epitope in the repeat domain of tau. The unlabelled lane shows only a minor band with gel mobility corresponding to 18 kD. The lane designated "B" shows a prominent gel band with mobility corresponding to 18 kD and a minor band corresponding to 14 kD. The lane designated "I" shows a minor band with gel mobility corresponding to 18 kD. The derivation of the 18 kD band in this cell system is explained in FIG. 1(D). As the tau fragment SStau296-390 has gel mobility of ~14 kD, the 18 kD species cannot arise as a degradation of product of the introduced tau fragment, nor is there evidence of formation of the 24 kD dimer seen e.g. in FIG. 16(D).

Figure 16D:
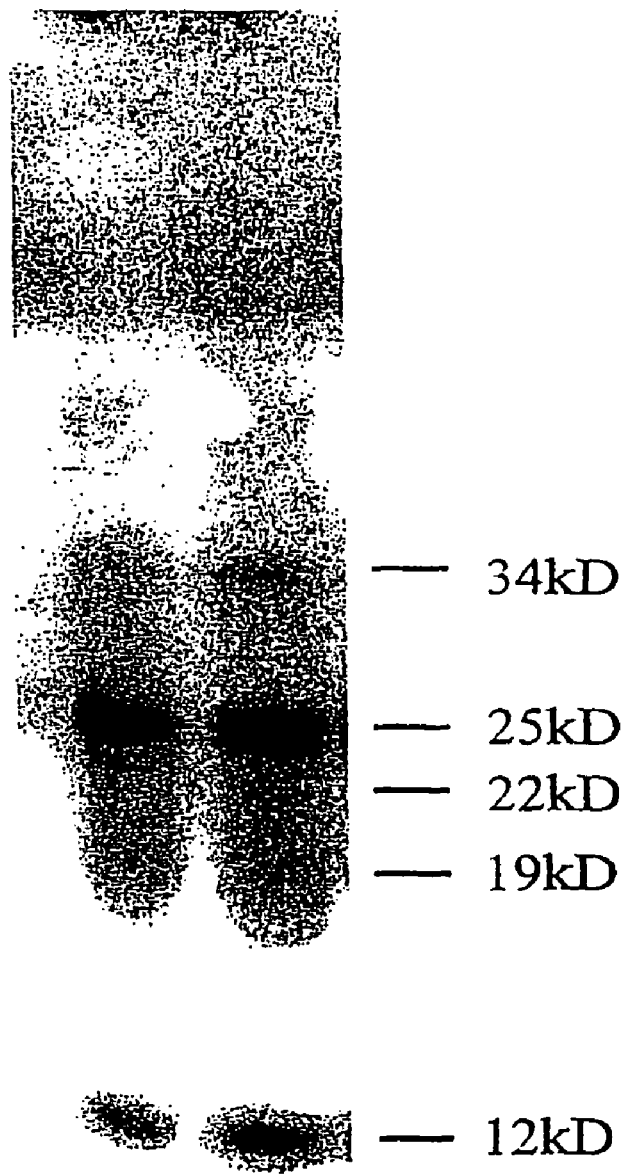

FIG. 16(D) shows how the tau dGAE fragment (residues 297-391) expressed bacterially in vitro aggregates spontaneously to form a series of higher order oligomers, of which the major form has gel mobility ~24 kD. There are minor atypical oligomers with gel mobility ~19/22 kD, which are most likely to be partially degraded forms of the dimer.

Figure 16E:
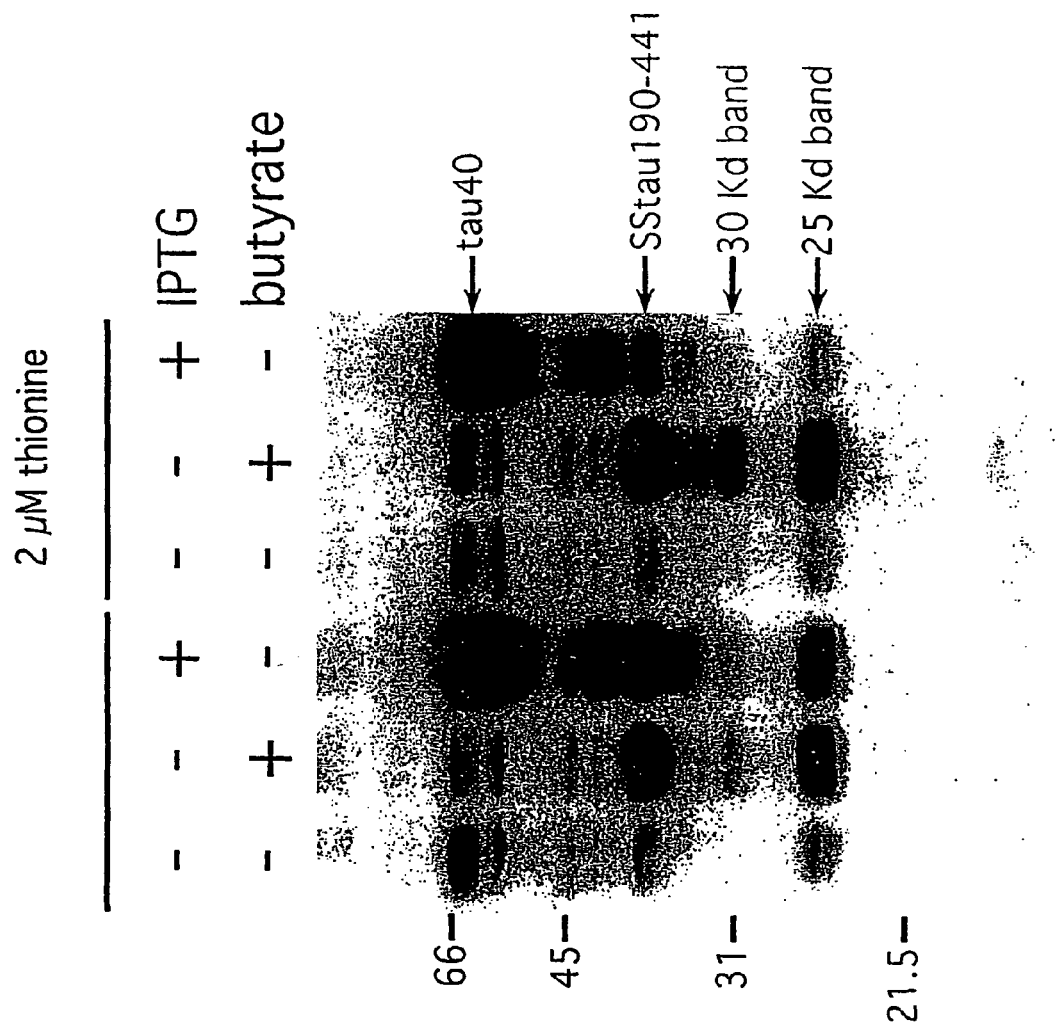

FIG. 16(E) left hand panel replicates the effect shown in (A), wherein IPTG gives rise to increased levels of 25K, 30K and 40K proteins, for comparison. The same experiment conducted in the presence of thionine blocks production of the 25K protein, and also reduces production of the 30K protein. Thionine does not, however, reduce detected levels of the 25K and 30K bands seen with butyrate. Therefore thionine is shown to block the capture and processing of full length tau that gives rise to the 25K band.

FIG. 17(A) shows the proteolytic processing of Sstau190-441. Cells expressing Sstau190-441 and induced to express full-length tau by treatment with IPTG (right-hand lane) were analysed with four antibodies recognising epitopes located along the length of tau. The gel shows analysis using mAb 7.51, which recognises the repeat domain of tau, reveal all of the tau fragments which contain the core aggregation domain. The remaining columns show a summary of the reactivity of the mAb 7.51positive fragments with three other antibodies. The results are also shown in a schematic representation of the fragments produced by processing of full-length tau and SStaul 190-441. Only full-length tau is recognised by all four antibodies. A fragment slightly larger than the SStau190-441 is produced by N-terminal truncation of full-length tau. Two fragments smaller than SStau190-441 are produced by either N-terminal or C-terminal processing. The two smallest fragments only react with the antibody to the core domain, demonstrating proteolytic stability of this domain. FIG. 17(B) shows the proteolytic processing of SStau190-390. Cells expressing SStaul 190-390 and treated with sodium butyrate (right-hand lane) produce SStaul 190-390 and a single proteolytic product of ~18 kD. As shown on the table and schematically at the right, the 18 kD species is immunoreactive only with mAb 7.51. The probable boundaries of the fragment are shown on the right, with reasons described in FIG. 1.

Figure 18:
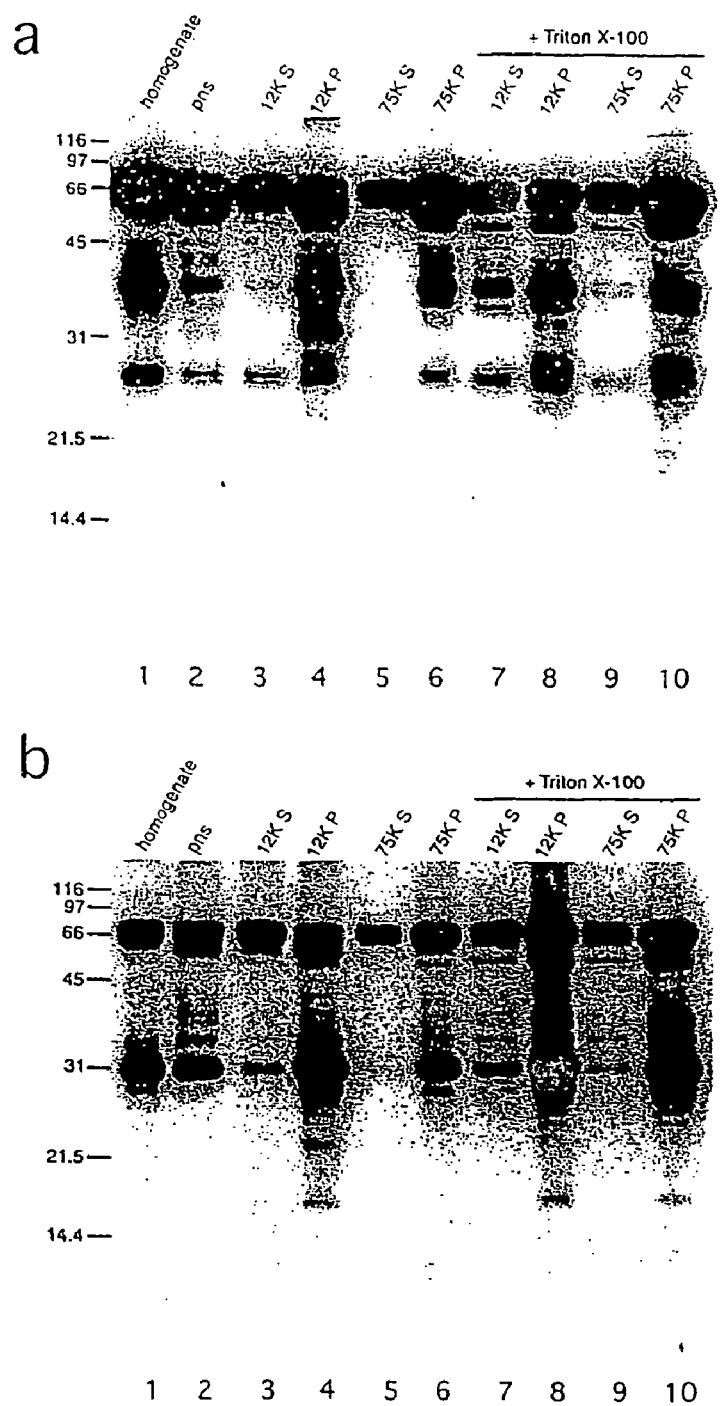

FIG. 18 shows the sedimentation of tau aggregates from cell extracts. Cells expressing (a) SStau190-441 or (b) SStau 190-390, and induced to express full-length tau, were homogenised and spun at 720 g for 3 min to produce a post-nuclear supernatant (pns). The pns was spun at 12,000 g for 2 min to sediment membranes and large aggregates, and the supernatant from this spin was spun at 200,000 g for 22 min. The same analysis was performed on pns that had been treated with 0.1% Triton X-100 to solubilise membrane proteins. Comparison of the 12K supernatants without and with detergent (lanes 3, 7) shows that more protein is present in the supernatant after detergent extraction. In both cases, a significant amount of protein also appears in the pellet (lanes 4, 8). Centrifugation of the 12K supernatants at 200 Kg sediments the remaining protein (lanes 6, 10).

Figure 19A:
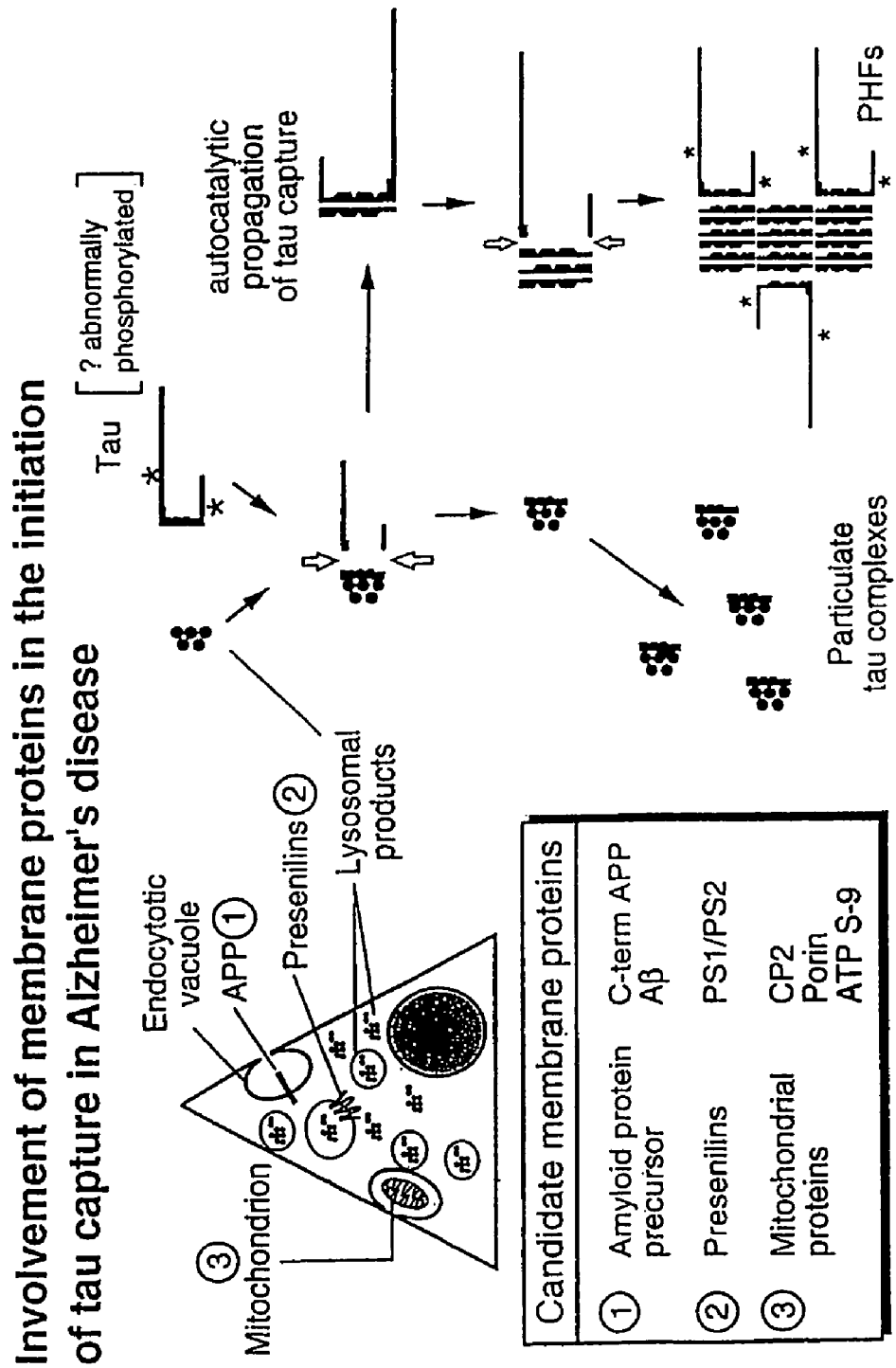
Figure 19B:
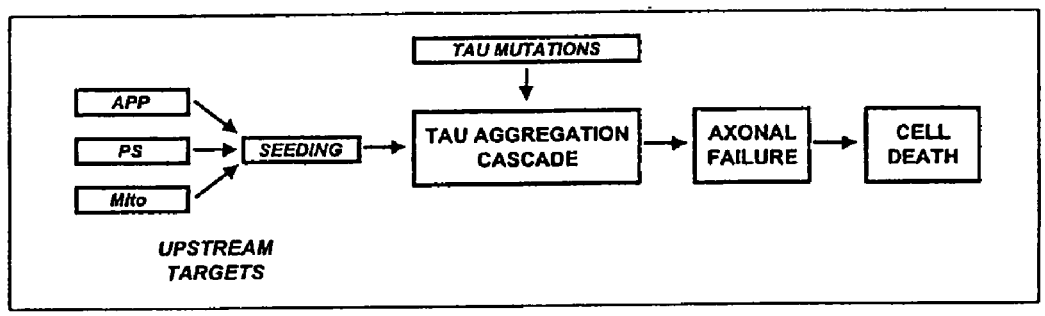

FIG. 19(A) shows a conceptual scheme wherein critical nucleating factors provide a 'seed' which initiates tau capture, which then becomes autocatalytic. FIG. 19(B) shows a putative pathogenic model of Alzheimer's disease. Tau aggregation is a proximal process prior to failure of axonal transport and consequent neuronal death. The tau aggregation cascade can be triggered either by a seeding/nucleation event arising from upstream changes or from primary mutations in the tau gene.

FIG. 20 shows a table listing proteins which play a role in diseases of protein aggregation. Also listed are the diseases themselves, the aggregating domain and/or mutation believed to be involved, and the putative (maximum) fibril subunit size. One or more literature references for each protein is given.

F*ig*. 21 Sequence analysis of proteins in the PH F-core preparation after removal of acid-soluble PHF-tau. The residue was solubilised according to the scrapie-fibril protocol of Stahl et al (1990, Biochemistry 29, 8879-8884). Yields are given for a typical preparation from a single AD brain. The protein fragments and corresponding residues identified as copurifying with PHF-core tau protein in bands of apparent gel mobility are shown in kD. The non-tau proteins copurifying in the form of SDS- and electrophoresis-resistant complexes are: ubiquitin, porin and core-protein-2 of mitochondrial complex III ("core-2"). ATP-synthase subunit 9 ("ATP-9") was found in a form which Co-purified with the Aβ protein of plaques. Porin sequences were also identified from Asp-N * and CNBr digests of the 34 kD species. The following sequences are identified in FIG. 21**: (a) is Seq ID No. 20 which is from $Q^{269}$ to Y; (b) is Seq ID No. 21 which is from $Q^{269}$ to V; (c) is Seq ID No. 22 which is from $D^{29}$ to K; (d) is Seq ID No. 23 which is from $Q^{269}$ to $P^{281}$; (e) is Seq ID No. 24 which is from $G^{16}$ to P: (f) is Seq ID No. 25 which is from $H^{268}$ to $V^{287}$; (g) is Seq ID No. 26 which is from $R^5$ to A: (h) is Seq ID No. 27 which is from $H^6$ to V; (i) is Seq ID No. 28 which is from $Y^{10}$ to H; (j) is Seq ID No. 29 which is from F to A; (k) is Seq ID No. 30 which is from V to $D^{283}$; (l) is Seq ID No. 31 which is from $1^2$ to V16.

EXAMPLES

Example 1

Production of Membrane Bound Protein

Introduction

An mRNA for a protein that is normally translated on free ribosomes can be targeted to membrane-bound ribosomes by inclusion of a signal sequence (SS) of a secreted protein; the nature of the 3'UTR also influences the efficiency of the targeting (Partridge, K. A., et al. (1999) *Cytotechnology* 30, 37-47). A protein that is normally soluble can therefore become inserted into the membrane of the endoplasmic reticulum. The present inventors have used this approach to construct a menbrane-associated form of tau that creates the localised concentration of tau needed to promote aggregation.

Cell lines stably expressing these membrane-associated forms of tau show evidence of tau aggregation and proteolytic processing by the criteria of histology, sedimentation of insoluble forms of tau protein from cell extracts and analysis of proteolytic products by immunoblotting.

Overview of Expression System

The expression system used for production of membrane associated tau fragments is summarised in FIG. 9. The system is based on the observation that rabbit globin mRNA is translated on membrane-bound ribosomes if the signal sequence of rat albumin is inserted at the 5' end of the cDNA (Partridge, K. A., et al., loc. cit.). The vector previously described for expression of globin (FIG. 9(A)) was modified to incorporate fragments of the tau sequence downstream of the signal sequence, while at the same time maintaining the globin 3'UTR (FIG. 9(B)).

Three truncation mutants of tau (amino acids 296-390, 190-441 and 190-390), referred to as Sstau296-390(Seq ID No. 5), Sstau190-441(Seq ID No. 3) and Sstau190-390(Seq ID No. 4), respectively, were expressed using this system. The structures of these mutants, together with full-length tau and the equivalent soluble tau fragments used as controls, are summarized in FIGS. 5 and 10. The proteins were expressed constitutively in 3T6 cells that also express the full-length tau sequence under the control of an IPTG-inducible promoter.

Construction of SStau Constructs.

pcKSSGG as shown in FIG. 9(A) and described by Partridge et al (1999) loc cit.

PCR-based mutagenesis on pcKSSGG to introduce an AgeI site at the globin start codon to make pcKSSGGAgeI.

forward primer: 5'-gccttttcaccggtgcatctgtcca-3' (Seq ID No. 8)

reverse primer: 5'-tggacagatgcaccggtgaaaaggc-3' Seq ID No. 9)

htau40 cDNA (see Goedert et al, 1989 Neurone 3, 519-526).

pcKSStau190-441

PCR-based mutagenesis on htau40to introduce an AgeI site at nucleotide 1128 of Htau40 (amino acid 186). Fragment cut with EcoRl (cuts the tau sequence beyond the stop codon), blunted, then with AgeI, ligated into pcKSSGGAgeI cut with BamHl, blunted, then AgeI to make pcKSStau190-441. The ligation destroys the tau sequence between amino acids 186-189, so amino acid 190 is the start of the tau sequence.

forward primer: 5'-tctggtgaaccggtaaaatacgggg-3' (Seq ID No. 10)

reverse primer: 5'-ccccgtattttaccggaacaccaga-3' (Seq ID No. 11)

pcKSStau190-390

PCR-based mutagensis on pcKSStau190-441 to introduce a BamHI site and stop codon at nucleotide 1740 (terminates the tau sequence at amino acid 390). Fragment cut with AgeI and BamHl and ligated into pcKSSGGAgeI at the same sites to make pcKSStau190-390.

forward primer: 5'-cttgtactcgagctacgccccgtgg-3' (Seq ID No. 12)

reverse primer: 5'-cggggcgtaggataagtacaagtcg-3' (Seq ID No. 13)

pcKSStau296-390

PCR-based mutagenesis on pcKSStau190-390 to introduce an AgeI site at nucleotide 1450 (amino acid 293) of pcKSStau190-390. Fragment cut with AgeI and BamHI and ligated into pcKSSGGAgeI at the same sites to make pcKSStau290-390.

forward primer: 5'-ggctcaccggttaatatcaaac-3' (Seq ID No. 14)
reverse primer: 5'-gtttgatattaaccggtgagcc-3' (Seq ID No. 15)

These constructs are in the expression vector pcDNA3.1, which contains the G418 resistance marker. All were subcloned in the pcDNA3.1zeo vector, which contains the zeocin resistance marker, for transfection into the T40 inducible cell line.

Construction of T40 Inducible Construct

This was based on the Stratagene system (Catalog No. 217450) in which a p3'SS vector (constitutively expressing the lac I gene, and selected for using hygromycin) is used in conjunction with pOPRSVICAT (which includes the strong RSV promoter with operator sequences from the Lac operon, and is selected for with neomycin). Briefly, the two vectors are incorporated into cells, such as 3T3 or 3T6 fibroblasts. The repression of the operon by lac I is relieved by the addition of IPTG. To prepare the T40 construct, the tau protein fragment was cloned into the pOPRSVICAT vector (which contains a NotI site) according to the manufacturer's instructions.

Results

The cells were analyzed by immunofluorescence labeling using an antibody directed against the core aggregation domain, mAb 7.51 (Novak, M., et al. (1991) *Proc. Natl. Acad. Sci. USA* 88, 5837-5841). By way of control, stably transfected 3T3 cells expressing the soluble tau fragment 186-441 were fixed with two different fixation conditions (a) paraformaldehyde or (b) glutaraldehyde and Triton X-100 and labeled with mAb 7.51 directed against the repeat domain of tau. After paraformaldehyde fixation, labeling for tau was diffuse throughout the cytoplasm (s previously reported by Schliwa et al., 1981, PNAS USA 78:1037-1041), whereas cells fixed in glutaraldehyde and Triton X-100 show labeling of the tau along microtubules. This labeling pattern was typical for soluble fragments of tau; evidence of tau aggregation is, however, not observed.

3T6 Cells stably transfected and expressing the membrane-targeted minimum aggregation domain, SStau296-390, were incubated with 5 mM sodium butyrate for 20 h to increase protein expression and fixed in paraformaldehyde. These became labeled by mAb 7.51 throughout the cytoplasm in a reticular pattern consistent with association with the endoplasmic reticulum (not shown). However, this protein was only expressed to detectable levels in a small proportion of the cells and aggregation of the protein was rarely seen.

In contrast, labeling of cells stably transfected with and expressing SStau190-441 or SStau190-390 reveals large aggregates, some of which have a linear appearance. These aggregates were often clustered in the perinuclear area, and sometimes have a filamentous form (FIG. 11).

The proportion of cells expressing these aggregates is increased by addition of sodium butyrate, which increases the expression level of the protein (Gorman, C. M., et al. (1983) *Nuc. Acids Res.* 11, 7631-7648; Kruh, J. (1982) *Mol. Cell. Biochem.* 42, 65-82), but aggregates can also be found in cells expressing the protein constitutively.

Cells stably transfected with and expressing SStau190-390 were also fixed in glutaraldehyde in the presence of 0.2% Triton X-100 before labeling with 7.51. This fixation protocol allows visualization of microtubule-bound tau protein, but aggregates of tau are also seen, demonstrating that they are stable to detergent extraction i.e. their stability per se is not dependent on membrane association (not shown).

Proteins expressed in these cell lines have been analyzed by immunoblotting with mAb 7.51, and the effect of tau induction and butyrate treatment examined, compared to cell lines expressing full-length tau and soluble fragments of tau.

The SStau190-441 protein analyzed by immunoblotting with the mAb 7.51 has an apparent RMM of ~40K and shows a characteristic degradation product at ~25K, and a less prominent product at ~30K. The expression level of the protein can be increased by treatment with sodium butyrate, which increases the amount of all three products (FIG. 16). Butyrate also occasionally induces the appearance of two smaller products at ~18 and ~14K (see FIG. 17).

Induction of full-length tau protein in the presence of Sstau190-441 increases the amount of products at 30K, and 25K, but there is no appearance of smaller products (FIG. 16(A)).

Thus, considering FIG. 16(A), when the effects of butyrate and IPTG induction are compared, butyrate is seen to act non-specifically to increase production of constitutively expressed incorporated gene products (by a mechanism which is not well understood). This serves as a control for IPTG induction, which specifically induces only full-length tau. In the first panel, the effects on expression of the non-membrane targeted 186-441 fragment after treatment with butyrate or IPTG are compared. Butyrate ("B") produces more of the 186-441 fragment, and a closely related presumed truncation product, but IPTG ("I") does not.

In the third panel, the same conditions are examined in cells simply expressing inducible T40 under IPTG control as described previously. Here, only IPTG ("I") produces increased levels of T40, and approx. 45 kD spontaneous degradation products. Butyrate has no effect.

The middle panel shows the effect of both induction methods in cells which express both SS 190-441 constitutively and T 40 under an IPTG-inducible promoter. Without induction, there are low levels of T40 and the characteristic 40 kD and 25 kD bands derived from SS190-441. Butyrate ("B") induces a higher level of the 40, 30 kD and 25 kD bands. Induction of T40 by IPTG ("I"), which has no effect on constitutive expression of the 40 kD band, generates higher levels of both the 40 kD and 25 kD species through an aggregation dependent mechanism (see FIG. 1). Therefore, induced T40 is being processed through the 40 kD pathway to give rise to the 25 kD truncation product, provided there are pre-existing low levels of SS 190-441.

Considering FIG. 16(B), the SStau190-390 protein analyzed by immunoblotting with the mAb 7.51has an apparent RMM of 30K and shows a degradation product at ~18K, which approximately corresponds to the size of the minimum aggregation domain of PHFs. Expression level of the protein and its characteristic 18 kD degradation product is substantially increased by treatment with sodium butyrate. Once again, the equivalent soluble tau fragment is not degraded in the same way and does not cause production of the 18 kD degradation product i.e. induction of full-length tau protein in the presence of SStau1 190-390 slightly increases the amount of 30K protein, but there is no increased appearance of the smaller product (FIG. 16(B)).

In both cases, the degradation pattern seen for the membrane-targeted tau fragments is different from that seen for the equivalent soluble protein. The membrane-targeted proteins can be degraded to a ~12\14 K fragment equivalent to the core domain of PHFs (see e.g. FIG. 17(A)). The aggregation of the tau fragments induced by membrane association is therefore conferring proteolytic stability to the core domain, as seen in PHFs.

Full-length tau protein which is induced in the absence of a membrane-localised tau fragment shows some degradation to a fragment of ~45K, but there is no production of smaller fragments. The enhanced production of smaller tau fragments seen when full-length tau is expressed with the SStau1 190-441(FIG. 16(A)) demonstrates processing of tau induced by interaction with the SStau190-441 aggregates.

The degradation products produced in cells expressing SStau190-441 have been analyzed using antibodies specific for epitopes which are both NB and C-terminal to the aggregation domain. This analysis shows that the protein undergoes both N- and C-terminal truncations (FIG. 17). The smallest fragment produced only reacts with the antibody against the core domain of PHFs and is of a similar size (~12-14K). The tau protein in these cells, therefore, appears to be undergoing PHF-like processing to the core fragment.

Both of the SStau proteins, together with their degradation products, can be sedimented from cell extracts even in the presence of the detergent Triton X-100, suggesting that the protein is aggregated rather than being associated with membranes (FIG. 18). A fraction of the protein sediments at relatively low speed (12,000 g), and the remainder behaves as particles with an S value of at least SOS, but does not sediment at 300 S, consistent with aggregation to a complex of MW ~1-2×10$^6$.

These results indicate the following pathway of events: aggregation, which is initially seeded by the membrane-localised protein, occurs at the cytosolic surface of the ER. The protein is cleaved at its N-terminus to remove the signal sequence, and this form is then free to appear as aggregates in the cytosol or as a microtubule-bound protein if aggregation has not occurred. Membrane-targeting of the tau-like protein, as taught herein, facilitates the capture of full-length tau which is, for instance, produced under the control of an inducible promoter. Further full-length tau is then channeled into the same proteolytic processing pathway, as indicated by production of the 25 kD unit after induction of full-length tau (FIG. 1).

Conclusion

Expressing a fragment of tau as a membrane-localised protein has overcome the barrier to aggregation in cells which is found using soluble proteins. The SS190-390 fragment, for example, is efficiently processed to shorter fragments including the 12-14K fragment, which is similar to that found in the core of PHFs.

The inventors have thus discovered that a signal sequence can be used to create a membrane-localised form of tau, that tau fragments thus expressed as membrane-localised proteins will form aggregates and that these tau aggregates have a proteolytically-stable core which is comparable to that in PHFs, both in relation to its size and to the presence of the 7.51 epitope. The inventors have also identified that the appearance of processed fragments is increased after induction of full-length tau protein, proving that there is capture of soluble tau into aggregates.

Thus, tau aggregation and processing have been achieved in cells, and the aggregates can be analyzed in assays to test for compounds which inhibit or modulate the aggregation.

Example 2

Screening Inhibitors

Cells expressing the SS190-441 fragment as well as inducible T40 under IPTG control were plated in 6 well dishes. One day after plating experimental drugs were added at indicated concentrations and 9 h later, IPTG was added at 5 mM. 15 h after IPTG addition, cells were washed with PBS then solubilised in gel buffer. Samples were separated by SDS-PAGE and immunoblotted using antibody 7.51. T40 induction in these cells leads to an increase in degradation products (as shown in FIG. 1, and FIG. 16(C)). The effect of the experimental drugs on this increase was analysed by quantification of the immunoblots.

FIG. 2 shows how the inhibitory activities of thionine, chlorpromazine and tacrine were compared in the membrane-targeted cell model. There is a clear distinction between active and inactive compounds. The data was analysed in greater detail mathematically using a standard inhibitory model (FIG. 3).

The values which the model yields are consistent with those which would be expected for an in vivo system in which the tau was phosphorylated, giving a resulting reduction in its binding affinity, and a concomitant increase in the apparent inhibitory potency of tau aggregation inhibitors.

This demonstrates the utility of the present invention in screening for inhibitors of the aggregation phenomena of proteins which undergo an induced conformation polymerisation in neuropathological disease. In particular the aggregation can be modified by aggregation inhibitors and their activity can be monitored by production of characteristic degradation products.

Example 3

Preparation and Use of Transgenic Animal

Transgenic animals were prepared as follows.

Animals:

To obtain a great number of fertilized oozytes, 4 week old NMRI mice are treated with gonadotrophins to induce superovulation. Pregnant mare's serum (PMS) is used to mimic follicle-stimulating hormone (FSH) and human chorionic gonadotropin (hCG) is used to mimic luteinizing hormone (LH). PMS is administered intraperitoneally 2 days before mating and hCG is administered 46 hours later. After administration of hCG the female mice are mated with stud males. On the same day 10 week old NMRI mice are mated with vasectomized males, to obtain foster mothers for the reimplantation of the injected oocytes. Fertilized oocytes are collected from mice with copulation plug the following morning.

Collection of Oozytes:

The mice are sacrificed by cervical dislocation and the oviduct is dissected. Newly ovulated oozytes, surrounded by cumulus cells, are found in the upper pan of the oviduct (ampulla). One oviduct at a time is transfered into a petridish containing M2 medium and hyaloronidase. With a pair of watchmakers forceps the oocytes can be released from the oviduct. The hyaloronidase separates the eggs from the cumulus cells. The oocytes are then separated from any other cells and material in two successive cleaning steps through M2 medium. Until needed the oocytes are stored in M16 medium at 37° C. in a 5% $CO_2$ incubator.

When collected the oozytes are in an early pronuclear stage wherein the male and female pronuclei are separated and distinguishable from the cytoplasm.

Preparation of the DNA construct for microinjection (see FIG. 6):

The constructs contain an appropriate cDNA under the regulation of the Thy1-promoter which directs transgene expression to the brain. The plasmids were extracted from the host bacteria and purified by Qiagen Plasmid Purification Kit (sold by Qiagen, Hilden, Germany). The constructs were linearized with an appropriate endonuclease (NotI). The desired fragment was isolated from agarose gel by using Qiaquick™ Gel Extraction Kit (sold by Qiagen, Hilden, Germany). The constructs were diluted to 2 ng/µl in microinjection buffer.

Microinjection:

One micromanipulator is mounted on each side of an inverted microscope stage; one micromanipulator controls the holding pipette and the other the injection pipette. The eggs are placed in a depression slide injection chamber with M2 medium covered with paraffin oil. One egg is positioned on the holding pipette and the male pronucleus is injected with the injection pipette containing the DNA solution. After injection the oocytes are again cultured in MI6 medium at 37° C. in a 5% $CO_2$ incubator until retransfer.

Retransfer:

Pseudopregnant mice are anesthetized and the intact injected oocytes are retransferred into the oviduct of the mouse (10-15 oocytes into one oviduct). These foster mothers carried the implantated embryos to term.

Identification of Transgenic Mice:

Two different approaches to identify transgenic animals were used.

PCR:

Transgenic mice were detected with PCR using transgene specific primers. Thy 1F2: gCA ggA ggT gCT CAg ggA CAg c (Seq ID No. 16) TautxR: CAC TgC CgC CTC CCg ggA CgT g (Seq ID No. 17)

This primer combination yields a 415 bp PCR fragment only in mice carrying the Thy1-sstau296-390 transgene and a 711 bp PCR fragment in the mice carrying the Thy1-sstau186-441 transgene.

Genomic DNA was prepared from 0.5 cm mouse tail using DNeasy™ Tissue Kit (Qiagen. Hilden. Germany)

Southern Blot

10 µg genomic DNA of PCR positive tested animals were digested with EcoR1 and electrophoresed on an 1% agarose gel. Southern blots were prepared and hybridized with 2 $^{32}$P-labeled fragments from the promoter. These were obtained by digestion with XbaI and NcoI. The endogenous signal can be compared with the transgene signal to estimate the copy number.

In order to test the mode of integration the genomic DNA was digested with XbaI. Founder 1 and F1 animals showed single integration. Founder 86 and F1 animals showed double integration and could be split into two independent lines.

Blots were hybridized at 65° C. for 20 hours and washed at 65° C. 2×1 hour.

RNA Expression

To study RNA expression Northern blot anaylsis has been done. RNA was prepared of whole brain using TrixolTM (Gibco BRL, Paisley, Scotland). 20 µg RNA was electrophoresed and blotted. Hybridisation was performed against a 247bp PCR fragment. Primers were transgene specific: glob578-597 (AAg AAC AAT CAA ggg T CC CC (Seq ID No. 18)), oligo20 (ATT Agg CAA CAT CCA TCA TAA ACC (Seq ID No. 19)).

Blots were hybridized at 65° C. for 20 hours and washed at 65° C. 2×1 hour.

Figure 1E:
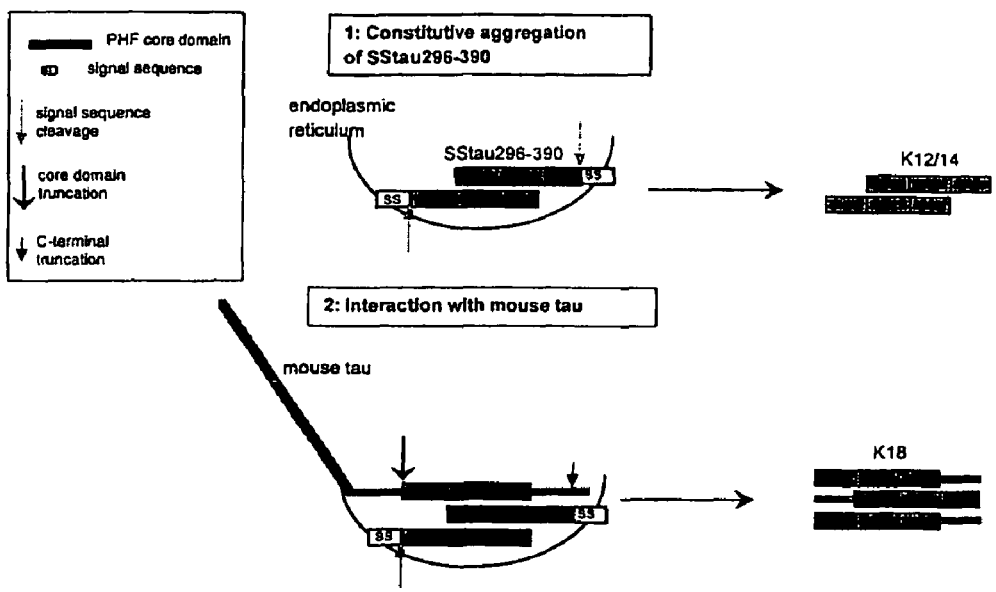

FIGS. 12-15 show the results obtained with the mouse model and describe how an 18 kD species is generated by aggregation-dependent proteolytic processing of endogenous mouse brain tau through a pathway believed to correspond to that given in FIG. 1(E).

REFERENCES

Arendt et al. (1995) Neuroscience 69, 691-698.
Braak et al. (1994) Neuroscience letters 171, 1-4.
Brion et al. (1999) American Journal of Pathology 154, 255.270.
Cork et al. (1988) Journal of Neuropathology and Experimental Neurology 49, 629-641.
Duff et al. (2000) Neurobiology of Disease 7, 87.98.
Geula et al. (1998) Nature Medicine 4, 827-834.
Gotz et al. (1995) EMBO Journal 14, 1304-1313.
Harada et al. (1994) Nature 369, 488-491.
Ikegami et al. (2000) Neuroscience letters 279, 129-132.
Ishihara et al. (1999) Neuron 24, 751-762.
Janus et al. (2000) Biochimica et Biophysica Acta 1502, 63-75.
Lewis et al. (2000) Nature Genetics 25, 402-405.
Nelson et al. (1995) Neurobiologyof Aging 16.315.323.
Roertgen et al. Neurobiology of Aging 17, 243-247.
Schultz et al. (2000) Journal of Neuropathology and Experimental Neurology 59, 39-52.
Spittaels et al. (1999) American Journal of Pathology 155 21532165.
Sturchler-Pierrat et al. (1997) Proceedings of the National Academy of Sciences, USA 93, 13287-13292.
Thunecke et al. (2000) unpublished.

Additional References

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. Human Genetics 89, 377-380.

Booth, D. R., Sunde, M., Bellotti, V., Robinson, C. V., Hutchinson, W. L., Fraser, P. E., Hawkins, P. N., Dobson, C. M., Radford, S. E., Blake, C. C. F. & Pepys, M. B. (1997) Instability, unfolding and aggregation of human lysozyme variants underlying amyloid fibrillogenesis. *Nature* 385, 787-793.

Carrell, R. W. & Gooptu, B. (1998) Conformational changes and disease—serpins, prions and Alzheimer's. *Current Opinion in Structural Biology* 8, 799-809.

Chiti, F., Webster, P., Taddei, N., Clark, A., Stafani, M., Ramponi, G. & Dobson, C. (1999) Designing conditions for in vitro formation of amyloid protofilaments and fibrils. *Proceedings of the National Academy of Sciences, USA* 96, 3590-3594.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C. -M., Gooptu, B., Elliott, P. R., Finch, J. T., Carrell, R. W. & Lomas, D. A. (1999) Familial dementia caused by polymerization of mutant neuroserpin. *Nature* 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. *Science* 277, 1990-1993.

Dische, F. E., Wernstedt, C., Westermark, G. T., Westermark, P., Pepys, M. B., Rennie, J. A., Gilbey, S. G. & Watkins, P. J. (1988) Insulin as an amyloid-fibril protein at sites of repeated insulin injections in a diabetic patient. *Diabetologia* 31, 158-161.

Gasset, M., Bladwin, M. A., Lloyd, D. H., abriel, J. -M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M. -C., Mullan, M., Brown, J., Crawford, F., Fidani, L., Giuffra, L., Haynes, A., Irving, N., James, L., Mant, R., Newton, P., Rooke, K., Roques, P., Talbot, C., Pericak-Vance, M., Roses, A., Williamson, R., Rossor, M., Owen, M. & Hardy, J. (1991) Segregation of a missense mutation in the amyloid precursor protein gene with familial Alzheimer's disease. *Nature* 349, 704-706.

Gorevic, P. D., Casey, T. T., Stone, W. J., DiRaimondo, C. R., Prelli, F. C. & Frangione, B. (1985) b-2 Microglobulin is an amyloidogenic protein in man. *Journal of Clinical Investigation* 76, 2425-2429.

Gustavsson, A., Engström, U. & Westermark, P. (1991) Normal transthyretin and synthetic transthyretin fragments form amyloid-like fibrils in vitro. *Biochemical and Biophysical Research Communications* 175, 1159-1164.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, B. A., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Johansson, B., Wernstedt, C. & Westermark, P. (1987) Atrial natriuretic peptide deposited as atrial amyloid fibrils. *Biochemical and Biophysical Research Communications* 148, 1087-1092.

Lomas, D. A., Evans, D. L., Finch, J. T. & Carrell, R. W. (1992) The mechanism of Z al-antitrypsin accumulation in the liver. *Nature* 357, 605-607.

Maury, C. P. & Baumann, M. (1990) Isolation and characterization of cardiac amyloid in familial amyloid polyneuropathy type IV (Finnish): relation of the amyloid protein to variant gelsolin. *Biochirnica et Biophysica Acta* 1096, 84-86.

Paulson, H. L. (1999) Human genetics '99: trinucleotide repeats. *American Journal of Human Genetics* 64, 339-345.

Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. & Hsuan, J. J. (1993) Human lysozyme gene mutations cause hereditary systemic amyloidosis. *Nature* 362, 553-557.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin, R. C., Di Iorio, G., Golbe, L. I. & Nussbaum, R. L. (1997) Mutation in the a-synuclein gene identified in families with Parkinson's disease. *Science* 276, 2045-2047.

Prusiner, S. B., Scott, M. R., DeArmond, S. J. & Cohen, F. E. (1998) Prion protein biology. *Cell* 93, 337-348.

Shibata, N., Hirano, A., Kobayashi, M., Siddique, T., Deng, H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. *Journal of Neuropathology and Experimental Neurology* 55, 481-490.

Sletten, K., Westermark, P. & Natvig, J. B. (1976) Characterization of amyloid fibril proteins from medullary carcinoma of the thyroid. *Journal of Experimental Medicine* 143, 993-998.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. *Proceedings of the National Academy of Sciences, USA* 95, 6469-6473.

Uemichi, T., Liuepnicks, J. j. & Benson, M. D. (1994) Hereditary renal amyloidosis with a novel variant fibrinogen. *Journal of Clinical Investigation* 93, 731-736.

Westermark, P., Engstrom, U., Johnson, K. H., Westermark, G. T. & Betsholtz, C. (1990) Islet amyloid polypeptide: pinpointing amino acid residues linked to amyloid fibril formation. *Proceedings of the National Academy of Sciences, USA* 87, 5036-5040.

Westermark, P., Johnson, K. H., O'Brien, T. D. & Betsholtz, C. (1992) Islet amyloid polypeptide—a novel controversy in diabetes research. *Diabetologia* 35, 297-303.

Westermark, P., Johnson, K. H. & Pitkanen, P. (1985) Systemic amyloidosis: A review with emphasis on pathogenesis. *Applied Physiology* 3, 55-68.

Wischik, C. M., Novak, M., Thøgersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences, USA* 85, 4506-4510.

The invention claimed is:

1. A transgenic rodent whose genome comprises a nucleic acid sequence operably linked to a promoter, wherein the nucleic acid encodes a cell membrane-localizable fusion protein comprising (i) a full-length tau protein or a tau core fragment, and (ii) a heterologous membrane-localizing polypeptide, wherein expression of the nucleic acid results in formation of tau protein aggregates at the cell membrane.

2. A cell or tissue sample of the transgenic rodent of claim 1 comprising a promoter operably linked to a nucleotide sequence encoding the membrane-localizable fusion protein.

3. The transgenic rodent of claim 1, wherein the membrane-localizing sequence includes a membrane anchor sequence and\or a stop-transfer sequence.

4. The transgenic rodent of claim 1, wherein the tau core fragment extends from an amino acid within the sequence comprising amino acids 186-296 to an amino acid within the sequence comprising amino acids 390-441 of the full-length tau protein.

5. The transgenic rodent of claim 4, wherein the tau core fragment consists of amino acid residues 296-390, 190-441 or 190-390 of the full-length protein.

6. The transgenic rodent of claim 1, wherein the tau protein is full length, soluble tau which is native to the cell.

7. The transgenic rodent of claim 1, wherein the tau protein or core fragment thereof is heterologous to the rodent.

8. The transgenic rodent of claim 7, wherein the fusion protein is expressed under the transcriptional control of a constitutive promoter.

9. The transgenic rodent of claim 7, wherein the tau protein or core fragment thereof is (i) a fragment of the tau protein, (ii) a mutant of the tau protein or core fragment thereof, or (iii) full length, soluble tau protein.

10. The transgenic rodent of claim 9, wherein the tau protein or core fragment thereof incorporates mutations into the tau protein of core fragment thereof corresponding to those known or suspected to be associated with a neurodegenerative disease.

11. A method of making a transgenic rodent, the method comprising the step of
  (a) introducing into a fertilized oocyte of a rodent a nucleotide sequence encoding a cell membrane-localizable fusion protein comprising (i) a full-length tau protein or a tau core fragment, and (ii) a heterologous membrane-localizing sequence, wherein the nucleotide sequence is operably linked to a promoter;
  (b) transplanting the fertilized oocyte into a pseudopregnant rodent of the same species as the fertilized oocyte;
  (c) allowing the fertilized oocyte to develop to term to produce a chimeric transgenic rodent:
  (d) mating the chimeric transgenic rodent and selecting for transgenic rodent offspring whose genome comprises the nucleic acid operably linked to the promoter;
  wherein the nucleic acid is expressed and results in formation of tau aggregates at the cell membrane of the rodent.

12. The method as claimed in claim 11 wherein the membrane localizing sequence includes a membrane anchor sequence and\or a stop-transfer sequence.

13. The method as claimed in claim 11 wherein the tau core fragment extends from an amino acid within the sequence comprising amino acids 186-296 to an amino acid within the sequence comprising amino acids 390-441 of the full-length tau protein.

14. The method as claimed in claim 13 wherein the tau core fragment consists of amino acid residues 296-390, 190-441 or 190-390 of the full-length protein.

15. The method as claimed in claim 11 further comprising the step of: monitoring the extent of aggregation of the tau protein or core fragment thereof.

16. The method as claimed in claim 15 wherein the tau protein is full length, soluble tau which is native to the cell.

17. The method as claimed in claim 15 wherein the tau protein or core fragment thereof is heterologous to the rodent.

18. The method as claimed in claim 17 wherein the fusion protein is expressed under the transcriptional control of a constitutive promoter.

19. The method as claimed in claim 17 wherein the tau protein or core fragment thereof is (i) a core fragment of the tau protein, (ii) a mutant of the tau protein or core fragment thereof, or (iii) full length, soluble tau protein.

20. The method as claimed in claim 19 wherein the tau protein or core fragment thereof incorporates mutations into the tau protein or core fragment thereof corresponding to those known or suspected to be associated with a neurodegenerative disease.

21. The method as claimed in claim 15 wherein the aggregation is monitored by monitoring the concentration or level of any one or more of the following species: (i) non-aggregated fusion protein and\or tau protein or core fragment thereof, (ii) an aggregate of the fusion protein and\or tau protein or core fragment thereof, (iii) a proteolytic fragment of the fusion protein and\or tau protein or core fragment thereof resulting from aggregation thereof.

22. The method as claimed in claim 21 wherein the aggregation is monitored on the basis of increasing levels of an approximately 18 or 25 kDa fragment of tau.

23. The method as claimed in claim 21 wherein the monitoring step comprises use of an antibody specific for any of (i) the fusion protein (ii) the tau protein or core fragment thereof (iii) a proteolytic fragment of the fusion protein and\or tau protein or core fragment thereof resulting from aggregation thereof.

24. The method as claimed in claim 23 wherein the fusion protein is immunologically distinct from the tau protein or core fragment thereof, and the antibody is selected from a monoclonal antibody which (i) is specific for a human-specific epitope located in the region between Gly-16 and Gln-26 of tau; (ii) is specific for the core tau fragment truncated at Glu-391; (iii) is specific for a generic tau epitope in the repeat domain; or (iv) is specific for a non-species specific generic tau epitope located between Ser-208 and Ser-238.

25. The method of claim 11,
wherein the promoter drives neuron-specific expression of the membrane-localizable fusion protein to produce tau protein aggregation.

26. The method of claim 25 wherein the promoter is selected from a tissue specific promoter; the prion specific promoter, or the neurospecific enolase promoter.

27. A transgenic mouse produced by the method of claim 11.

28. A method for identifying a modulator of tau protein aggregation comprising:
   (a) administering an agent to a first transgenic rodent whose genome comprises a, nucleic acid sequence operably linked to a promoter, wherein said nucleic acid sequence encodes a cell membrane-localized fusion protein comprising a full-length tau or tau core fragment and a heterologous membrane localizing polypeptide, wherein expression of said nucleic acid results in formation of tau aggregates at the cell membrane,
   (b) monitoring tau aggregation in said rodent,
   (c) comparing tau aggregation with a second, control transgenic rodent that was not administered the agent, wherein a difference in tau aggregation between the first transgenic rodent that received the agent and the second transgenic rodent that was not administered the agent identifies the agent as a modulator of tau aggregation.

29. The method as claimed in claim 28 wherein the agent is capable of crossing the blood-brain barrier.

30. The method as claimed in claim 28 wherein any of the following is determined within the brain of the transgenic rodent:
   (i) the extent of proteolytic processing of tau,
   (ii) the ability of the agent to decrease the amount of tau aggregates which form,
   (iii) the ability of the agent to eliminate or reduce the level of tau aggregate already formed.

* * * * *

SEQUENCE LISTING

```
<160> NUMBER OF SEQ ID NOS: 31

<210> SEQ ID NO 1
<211> LENGTH: 1326
<212> TYPE: DNA
<213> ORGANISM: Homo sapiens
<220> FEATURE:
<221> NAME/KEY: CDS
```

<222> LOCATION: (1)..(1326)

<400> SEQUENCE: 1

| | | | | | | | | | | | | | | | | |
|---|---|---|---|---|---|---|---|---|---|---|---|---|---|---|---|---|
| atg | gct | gag | ccc | cgc | cag | gag | ttc | gaa | gtg | atg | gaa | gat | cac | gct | ggg | 48 |
| Met | Ala | Glu | Pro | Arg | Gln | Glu | Phe | Glu | Val | Met | Glu | Asp | His | Ala | Gly | |
| 1 | | | | 5 | | | | | 10 | | | | | 15 | | |
| acg | tac | ggg | ttg | ggg | gac | agg | aaa | gat | cag | ggg | ggc | tac | acc | atg | cac | 96 |
| Thr | Tyr | Gly | Leu | Gly | Asp | Arg | Lys | Asp | Gln | Gly | Gly | Tyr | Thr | Met | His | |
| | | | 20 | | | | | 25 | | | | | 30 | | | |
| caa | gac | caa | gag | ggt | gac | acg | gac | gct | ggc | ctg | aaa | gaa | tct | ccc | ctg | 144 |
| Gln | Asp | Gln | Glu | Gly | Asp | Thr | Asp | Ala | Gly | Leu | Lys | Glu | Ser | Pro | Leu | |
| | 35 | | | | | 40 | | | | | 45 | | | | | |
| cag | acc | ccc | act | gag | gac | gga | tct | gag | gaa | ccg | ggc | tct | gaa | acc | tct | 192 |
| Gln | Thr | Pro | Thr | Glu | Asp | Gly | Ser | Glu | Glu | Pro | Gly | Ser | Glu | Thr | Ser | |
| 50 | | | | | 55 | | | | | 60 | | | | | | |
| gat | gct | aag | agc | act | cca | aca | gcg | gaa | gat | gtg | aca | gca | ccc | tta | gtg | 240 |
| Asp | Ala | Lys | Ser | Thr | Pro | Thr | Ala | Glu | Asp | Val | Thr | Ala | Pro | Leu | Val | |
| 65 | | | | 70 | | | | | 75 | | | | | 80 | | |
| gat | gag | gga | gct | ccc | ggc | aag | cag | gct | gcc | gcg | cag | ccc | cac | acg | gag | 288 |
| Asp | Glu | Gly | Ala | Pro | Gly | Lys | Gln | Ala | Ala | Ala | Gln | Pro | His | Thr | Glu | |
| | | | | 85 | | | | | 90 | | | | | 95 | | |
| atc | cca | gaa | gga | acc | aca | gct | gaa | gaa | gca | ggc | att | gga | gac | acc | ccc | 336 |
| Ile | Pro | Glu | Gly | Thr | Thr | Ala | Glu | Glu | Ala | Gly | Ile | Gly | Asp | Thr | Pro | |
| | | | 100 | | | | | 105 | | | | | 110 | | | |
| agc | ctg | gaa | gac | gaa | gct | gct | ggt | cac | gtg | acc | caa | gct | cgc | atg | gtc | 384 |
| Ser | Leu | Glu | Asp | Glu | Ala | Ala | Gly | His | Val | Thr | Gln | Ala | Arg | Met | Val | |
| | 115 | | | | | 120 | | | | | 125 | | | | | |
| agt | aaa | agc | aaa | gac | ggg | act | gga | agc | gat | gac | aaa | aaa | gcc | aag | ggg | 432 |
| Ser | Lys | Ser | Lys | Asp | Gly | Thr | Gly | Ser | Asp | Asp | Lys | Lys | Ala | Lys | Gly | |
| 130 | | | | | 135 | | | | | 140 | | | | | | |
| gct | gat | ggt | aaa | acg | aag | atc | gcc | aca | ccg | cgg | gga | gca | gcc | cct | cca | 480 |
| Ala | Asp | Gly | Lys | Thr | Lys | Ile | Ala | Thr | Pro | Arg | Gly | Ala | Ala | Pro | Pro | |
| 145 | | | | 150 | | | | | 155 | | | | | 160 | | |
| ggc | cag | aag | ggc | cag | gcc | aac | gcc | acc | agg | att | cca | gca | aaa | acc | ccg | 528 |
| Gly | Gln | Lys | Gly | Gln | Ala | Asn | Ala | Thr | Arg | Ile | Pro | Ala | Lys | Thr | Pro | |
| | | | | 165 | | | | | 170 | | | | | 175 | | |
| ccc | gct | cca | aag | aca | cca | ccc | agc | tct | ggt | gaa | cct | cca | aaa | tca | ggg | 576 |
| Pro | Ala | Pro | Lys | Thr | Pro | Pro | Ser | Ser | Gly | Glu | Pro | Pro | Lys | Ser | Gly | |
| | | | 180 | | | | | 185 | | | | | 190 | | | |
| gat | cgc | agc | ggc | tac | agc | agc | ccc | ggc | tcc | cca | ggc | act | ccc | ggc | agc | 624 |
| Asp | Arg | Ser | Gly | Tyr | Ser | Ser | Pro | Gly | Ser | Pro | Gly | Thr | Pro | Gly | Ser | |
| | 195 | | | | | 200 | | | | | 205 | | | | | |
| cgc | tcc | cgc | acc | ccg | tcc | ctt | cca | acc | cca | ccc | acc | cgg | gag | ccc | aag | 672 |
| Arg | Ser | Arg | Thr | Pro | Ser | Leu | Pro | Thr | Pro | Pro | Thr | Arg | Glu | Pro | Lys | |
| 210 | | | | | 215 | | | | | 220 | | | | | | |
| aag | gtg | gca | gtg | gtc | cgt | act | cca | ccc | aag | tcg | ccg | tct | tcc | gcc | aag | 720 |
| Lys | Val | Ala | Val | Val | Arg | Thr | Pro | Pro | Lys | Ser | Pro | Ser | Ser | Ala | Lys | |
| 225 | | | | 230 | | | | | 235 | | | | | 240 | | |
| agc | cgc | ctg | cag | aca | gcc | ccc | gtg | ccc | atg | cca | gac | ctg | aag | aat | gtc | 768 |
| Ser | Arg | Leu | Gln | Thr | Ala | Pro | Val | Pro | Met | Pro | Asp | Leu | Lys | Asn | Val | |
| | | | | 245 | | | | | 250 | | | | | 255 | | |
| aag | tcc | aag | atc | ggc | tcc | act | gag | aac | ctg | aag | cac | cag | ccg | gga | ggc | 816 |
| Lys | Ser | Lys | Ile | Gly | Ser | Thr | Glu | Asn | Leu | Lys | His | Gln | Pro | Gly | Gly | |
| | | | 260 | | | | | 265 | | | | | 270 | | | |
| ggg | aag | gtg | cag | ata | att | aat | aag | aag | ctg | gat | ctt | agc | aac | gtc | cag | 864 |
| Gly | Lys | Val | Gln | Ile | Ile | Asn | Lys | Lys | Leu | Asp | Leu | Ser | Asn | Val | Gln | |
| | 275 | | | | | 280 | | | | | 285 | | | | | |
| tcc | aag | tgt | ggc | tca | aag | gat | aat | atc | aaa | cac | gtc | ccg | gga | ggc | ggc | 912 |
| Ser | Lys | Cys | Gly | Ser | Lys | Asp | Asn | Ile | Lys | His | Val | Pro | Gly | Gly | Gly | |
| 290 | | | | | 295 | | | | | 300 | | | | | | |

```
agt gtg caa ata gtc tac aaa cca gtt gac ctg agc aag gtg acc tcc        960
Ser Val Gln Ile Val Tyr Lys Pro Val Asp Leu Ser Lys Val Thr Ser
305             310                 315                 320 aag tgt ggc tca tta ggc aac atc cat cat aaa cca gga ggt ggc cag       1008
Lys Cys Gly Ser Leu Gly Asn Ile His His Lys Pro Gly Gly Gly Gln
                325                 330                 335 gtg gaa gta aaa tct gag aag ctt gac ttc aag gac aga gtc cag tcg       1056
Val Glu Val Lys Ser Glu Lys Leu Asp Phe Lys Asp Arg Val Gln Ser
            340                 345                 350 aag att ggg tcc ctg gac aat atc acc cac gtc cct ggc gga gga aat       1104
Lys Ile Gly Ser Leu Asp Asn Ile Thr His Val Pro Gly Gly Gly Asn
        355                 360                 365 aaa aag att gaa acc cac aag ctg acc ttc cgc gag aac gcc aaa gcc       1152
Lys Lys Ile Glu Thr His Lys Leu Thr Phe Arg Glu Asn Ala Lys Ala
370                 375                 380 aag aca gac cac ggg gcg gag atc gtg tac aag tcg cca gtg gtg tct       1200
Lys Thr Asp His Gly Ala Glu Ile Val Tyr Lys Ser Pro Val Val Ser
385                 390                 395                 400 ggg gac acg tct cca cgg cat ctc agc aat gtc tcc tcc acc ggc agc       1248
Gly Asp Thr Ser Pro Arg His Leu Ser Asn Val Ser Ser Thr Gly Ser
                405                 410                 415 atc gac atg gta gac tcg ccc cag ctc gcc acg cta gct gac gag gtg       1296
Ile Asp Met Val Asp Ser Pro Gln Leu Ala Thr Leu Ala Asp Glu Val
            420                 425                 430 tct gcc tcc ctg gcc aag cag ggt ttg tga                               1326
Ser Ala Ser Leu Ala Lys Gln Gly Leu
                435                 440

<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
```

-continued

```
            180                 185                 190
Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
        260                 265                 270

Gly Lys Val Gln Ile Ile Asn Lys Lys Leu Asp Leu Ser Asn Val Gln
    275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
        340                 345                 350

Lys Ile Gly Ser Leu Asp Asn Ile Thr His Val Pro Gly Gly Gly Asn
    355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
        420                 425                 430

Ser Ala Ser Leu Ala Lys Gln Gly Leu
            435                 440

<210> SEQ ID NO 3
<211> LENGTH: 272
<212> TYPE: PRT
<213> ORGANISM: Artificial Sequence
<220> FEATURE:
<223> OTHER INFORMATION: Description of Artificial Sequence: SStau
      186-441

<400> SEQUENCE: 3

Met Lys Trp Val Thr Phe Leu Leu Leu Leu Phe Ile Ser Gly Ser Ala
  1               5                  10                  15

Phe Ser Pro Val Lys Ser Gly Asp Arg Ser Gly Tyr Ser Ser Pro Gly
             20                  25                  30

Ser Pro Gly Thr Pro Gly Ser Arg Ser Arg Thr Pro Ser Leu Pro Thr
         35                  40                  45

Pro Pro Thr Arg Glu Pro Lys Lys Val Ala Val Val Arg Thr Pro Pro
     50                  55                  60

Lys Ser Pro Ser Ser Ala Lys Ser Arg Leu Gln Thr Ala Pro Val Pro
 65                  70                  75                  80

Met Pro Asp Leu Lys Asn Val Lys Ser Lys Ile Gly Ser Thr Glu Asn
                 85                  90                  95
```

```
Leu Lys His Gln Pro Gly Gly Gly Lys Val Gln Ile Ile Asn Lys Lys
                100                 105                 110

Leu Asp Leu Ser Asn Val Gln Ser Lys Cys Gly Ser Lys Asp Asn Ile
            115                 120                 125

Lys His Val Pro Gly Gly Gly Ser Val Gln Ile Val Tyr Lys Pro Val
        130                 135                 140

Asp Leu Ser Lys Val Thr Ser Lys Cys Gly Ser Leu Gly Asn Ile His
145                 150                 155                 160

His Lys Pro Gly Gly Gly Gln Val Glu Val Lys Ser Glu Lys Leu Asp
                165                 170                 175

Phe Lys Asp Arg Val Gln Ser Lys Ile Gly Ser Leu Asp Asn Ile Thr
            180                 185                 190

His Val Pro Gly Gly Gly Asn Lys Lys Ile Glu Thr His Lys Leu Thr
        195                 200                 205

Phe Arg Glu Asn Ala Lys Ala Lys Thr Asp His Gly Ala Glu Ile Val
    210                 215                 220

Tyr Lys Ser Pro Val Val Ser Gly Asp Thr Ser Pro Arg His Leu Ser
225                 230                 235                 240

Asn Val Ser Ser Thr Gly Ser Ile Asp Met Val Asp Ser Pro Gln Leu
                245                 250                 255

Ala Thr Leu Ala Asp Glu Val Ser Ala Ser Leu Ala Lys Gln Gly Leu
            260                 265                 270

<210> SEQ ID NO 4
<211> LENGTH: 221
<212> TYPE: PRT
<213> ORGANISM: Artificial Sequence
<220> FEATURE:
<223> OTHER INFORMATION: Description of Artificial Sequence: SStau
      186-390

<400> SEQUENCE: 4

Met Lys Trp Val Thr Phe Leu Leu Leu Leu Phe Ile Ser Gly Ser Ala
1               5                   10                  15

Phe Ser Pro Val Lys Ser Gly Asp Arg Ser Gly Tyr Ser Ser Pro Gly
            20                  25                  30

Ser Pro Gly Thr Pro Gly Ser Arg Ser Arg Thr Pro Ser Leu Pro Thr
        35                  40                  45

Pro Pro Thr Arg Glu Pro Lys Lys Val Ala Val Val Arg Thr Pro Pro
    50                  55                  60

Lys Ser Pro Ser Ser Ala Lys Ser Arg Leu Gln Thr Ala Pro Val Pro
65                  70                  75                  80

Met Pro Asp Leu Lys Asn Val Lys Ser Lys Ile Gly Ser Thr Glu Asn
                85                  90                  95

Leu Lys His Gln Pro Gly Gly Gly Lys Val Gln Ile Ile Asn Lys Lys
                100                 105                 110

Leu Asp Leu Ser Asn Val Gln Ser Lys Cys Gly Ser Lys Asp Asn Ile
            115                 120                 125

Lys His Val Pro Gly Gly Gly Ser Val Gln Ile Val Tyr Lys Pro Val
        130                 135                 140

Asp Leu Ser Lys Val Thr Ser Lys Cys Gly Ser Leu Gly Asn Ile His
145                 150                 155                 160

His Lys Pro Gly Gly Gly Gln Val Glu Val Lys Ser Glu Lys Leu Asp
                165                 170                 175

Phe Lys Asp Arg Val Gln Ser Lys Ile Gly Ser Leu Asp Asn Ile Thr
            180                 185                 190
```

```
His Val Pro Gly Gly Gly Asn Lys Lys Ile Glu Thr His Lys Leu Thr
            195                 200                 205

Phe Arg Glu Asn Ala Lys Ala Lys Thr Asp His Gly Ala
        210                 215                 220

<210> SEQ ID NO 5
<211> LENGTH: 115
<212> TYPE: PRT
<213> ORGANISM: Artificial Sequence
<220> FEATURE:
<223> OTHER INFORMATION: Description of Artificial Sequence: SStau
      296-390

<400> SEQUENCE: 5

Met Lys Trp Val Thr Phe Leu Leu Leu Leu Phe Ile Ser Gly Ser Ala
  1               5                  10                  15

Phe Ser Pro Val Asn Ile Lys His Val Pro Gly Gly Gly Ser Val Gln
             20                  25                  30

Ile Val Tyr Lys Pro Val Asp Leu Ser Lys Val Thr Ser Lys Cys Gly
         35                  40                  45

Ser Leu Gly Asn Ile His His Lys Pro Gly Gly Gly Gln Val Glu Val
 50                  55                  60

Lys Ser Glu Lys Leu Asp Phe Lys Asp Arg Val Gln Ser Lys Ile Gly
 65                  70                  75                  80

Ser Leu Asp Asn Ile Thr His Val Pro Gly Gly Gly Asn Lys Lys Ile
                 85                  90                  95

Glu Thr His Lys Leu Thr Phe Arg Glu Asn Ala Lys Ala Lys Thr Asp
            100                 105                 110

His Gly Ala
        115

<210> SEQ ID NO 6
<211> LENGTH: 140
<212> TYPE: PRT
<213> ORGANISM: Homo sapiens

<400> SEQUENCE: 6

Asp Leu Lys Asn Val Lys Ser Lys Ile Gly Ser Thr Glu Asn Leu Lys
  1               5                  10                  15

His Gln Pro Gly Gly Gly Lys Val Gln Ile Ile Asn Lys Lys Leu Asp
             20                  25                  30

Leu Ser Asn Val Gln Ser Lys Cys Gly Ser Lys Asp Asn Ile Lys His
         35                  40                  45

Val Pro Gly Gly Gly Ser Val Gln Ile Val Tyr Lys Pro Val Asp Leu
 50                  55                  60

Ser Lys Val Thr Ser Lys Cys Gly Ser Leu Gly Asn Ile His His Lys
 65                  70                  75                  80

Pro Gly Gly Gly Gln Val Glu Val Lys Ser Glu Lys Leu Asp Phe Lys
                 85                  90                  95

Asp Arg Val Gln Ser Lys Ile Gly Ser Leu Asp Asn Ile Thr His Val
            100                 105                 110

Pro Gly Gly Gly Asn Lys Lys Ile Glu Thr His Lys Leu Thr Phe Arg
            115                 120                 125

Glu Asn Ala Lys Ala Lys Thr Asp His Gly Ala Glu
        130                 135                 140

<210> SEQ ID NO 7
```

```
<211> LENGTH: 140
<212> TYPE: PRT
<213> ORGANISM: Homo sapiens

<400> SEQUENCE: 7

Asp Leu Lys Asn Val Lys Ser Lys Ile Gly Ser Thr Asp Asn Ile Lys
 1               5                  10                  15

Tyr Gln Pro Lys Gly Gly Gln Val Arg Ile Leu Asn Lys Lys Ile Asp
            20                  25                  30

Phe Ser Lys Val Gln Ser Arg Cys Gly Ser Lys Asp Asn Ile Lys His
        35                  40                  45

Ser Ala Gly Gly Asn Val Gln Ile Val Thr Lys Lys Ile Asp Leu
    50                  55                  60

Ser His Val Thr Ser Lys Cys Gly Ser Leu Lys Asn Ile Arg His Arg
65                  70                  75                  80

Pro Gly Gly Gly Arg Val Lys Ile Glu Ser Val Lys Leu Asp Phe Lys
                85                  90                  95

Glu Lys Val Gln Ala Lys Val Gly Ser Leu Asp Asn Ala His His Val
            100                 105                 110

Pro Gly Gly Gly Asn Val Lys Ile Asp Ser Gln Lys Leu Asn Phe Arg
        115                 120                 125

Glu His Ala Lys Ala Arg Val Asp His Gly Ala Glu
    130                 135                 140

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8 gcctttcac cggtgcatct gtcca                                      25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
tggacagatg caccggtgaa aaggc                                     25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 10
tctggtgaac cggtaaaata cgggg                                     25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
```

-continued ccccgtattt taccggaaca ccaga                                              25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 12
cttgtactcg agctacgccc cgtgg                                              25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 13
cggggcgtag gataagtaca agtcg                                              25

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 14
ggctcaccgg ttaatatcaa ac                                                 22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 15
gtttgatatt aaccggtgag cc                                                 22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
gcaggaggtg ctcagggaca gc                                                 22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 17
cactgccgcc tcccgggacg tg                                                 22

<210> SEQ ID NO 18
<211> LENGTH: 20
<212> TYPE: DNA
<213> ORGANISM: Artificial Sequence -continued

```
<220> FEATURE:
<223> OTHER INFORMATION: Description of Artificial Sequence: Primer

<400> SEQUENCE: 18
aagaacaatc aagggtcccc                                              20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
attaggcaac atccatcata aacc                                         24

<210> SEQ ID NO 20
<211> LENGTH: 11
<212> TYPE: PRT
<213> ORGANISM: Homo sapiens

<400> SEQUENCE: 20

Gln Pro Gly Gly Gly Lys Val Gln Ile Val Tyr
  1               5                  10

<210> SEQ ID NO 21
<211> LENGTH: 7
<212> TYPE: PRT
<213> ORGANISM: Homo sapiens

<400> SEQUENCE: 21

Gln Pro Gly Gly Gly Lys Val
  1               5

<210> SEQ ID NO 22
<211> LENGTH: 5
<212> TYPE: PRT
<213> ORGANISM: Homo sapiens

<400> SEQUENCE: 22

Asp Leu Lys Thr Lys
  1               5

<210> SEQ ID NO 23
<211> LENGTH: 13
<212> TYPE: PRT
<213> ORGANISM: Homo sapiens

<400> SEQUENCE: 23

Gln Pro Gly Gly Gly Lys Val Gln Ile Val Tyr Lys Pro
  1               5                  10

<210> SEQ ID NO 24
<211> LENGTH: 15
<212> TYPE: PRT
<213> ORGANISM: Homo sapiens

<400> SEQUENCE: 24

Gly Ala Pro Pro Gln Pro Gln Asp Leu Glu Phe Thr Lys Leu Pro
  1               5                  10                  15

<210> SEQ ID NO 25
<211> LENGTH: 20
<212> TYPE: PRT
<213> ORGANISM: Homo sapiens
```

```
<220> FEATURE:
<221> NAME/KEY: SITE
<222> LOCATION: (2)
<223> OTHER INFORMATION: Xaa is Gln or Val
<220> FEATURE:
<221> NAME/KEY: SITE
<222> LOCATION: (7)
<223> OTHER INFORMATION: Xaa is Lys or Ser
<220> FEATURE:
<221> NAME/KEY: SITE
<222> LOCATION: (11)
<223> OTHER INFORMATION: Xaa is Val or Ile

<400> SEQUENCE: 25

His Xaa Pro Gly Gly Gly Xaa Val Gln Ile Xaa Tyr Lys Pro Val Asp
  1               5                  10                  15

Leu Ser Lys Val
            20

<210> SEQ ID NO 26
<211> LENGTH: 17
<212> TYPE: PRT
<213> ORGANISM: Homo sapiens

<400> SEQUENCE: 26

Arg His Asp Ser Gly Tyr Glu Val His His Gln Lys Leu Val Phe Phe
  1               5                  10                  15

Ala

<210> SEQ ID NO 27
<211> LENGTH: 7
<212> TYPE: PRT
<213> ORGANISM: Homo sapiens

<400> SEQUENCE: 27

His Asp Ser Gly Tyr Glu Val
  1               5

<210> SEQ ID NO 28
<211> LENGTH: 4
<212> TYPE: PRT
<213> ORGANISM: Homo sapiens

<400> SEQUENCE: 28

Tyr Glu Val His
  1

<210> SEQ ID NO 29
<211> LENGTH: 7
<212> TYPE: PRT
<213> ORGANISM: Homo sapiens

<400> SEQUENCE: 29

Phe Ile Gly Ala Gly Ala Ala
  1               5

<210> SEQ ID NO 30
<211> LENGTH: 6
<212> TYPE: PRT
<213> ORGANISM: Homo sapiens

<400> SEQUENCE: 30

Val Tyr Lys Pro Val Asp
  1               5
```

```
<210> SEQ ID NO 31
<211> LENGTH: 15
<212> TYPE: PRT
<213> ORGANISM: Homo sapiens

<400> SEQUENCE: 31

Ile Asp Thr Ala Ala Lys Phe Ile Gly Ala Gly Ala Ala Thr Val
1               5                   10                  15
```